United States Patent
Park et al.

(10) Patent No.: US 10,023,591 B2
(45) Date of Patent: Jul. 17, 2018

(54) HETEROCYCLIC DERIVATIVES AND USE THEREOF

(71) Applicant: C&C RESEARCH LABORATORIES, Suwon-si, Gyeonggi-do (KR)

(72) Inventors: Chan Hee Park, Suwon-si (KR); Sang Hwi Lee, Suwon-si (KR); Junhwan Im, Suwon-si (KR); Soon Ok Lee, Suwon-si (KR); Jongmin Kim, Suwon-si (KR); Kwang Seok Ko, Suwon-si (KR); Byungho Kim, Suwon-si (KR); Minjung Kong, Suwon-si (KR); Mi Sun Kim, Suwon-si (KR); Hyung Jo Moon, Suwon-si (KR)

(73) Assignee: C&C RESEARCH LABORATORIES, Suwon-si (KR)

( * ) Notice: Subject to any disclaimer, the term of this patent is extended or adjusted under 35 U.S.C. 154(b) by 0 days.

(21) Appl. No.: 15/526,415

(22) PCT Filed: Nov. 30, 2015

(86) PCT No.: PCT/KR2015/012920
§ 371 (c)(1),
(2) Date: May 12, 2017

(87) PCT Pub. No.: WO2016/089060
PCT Pub. Date: Jun. 9, 2016

(65) Prior Publication Data
US 2017/0320889 A1    Nov. 9, 2017

(30) Foreign Application Priority Data
Dec. 2, 2014 (KR) .................... 10-2014-0170860

(51) Int. Cl.
*C07D 495/04* (2006.01)
*C07D 333/70* (2006.01)
*C07D 409/12* (2006.01)
*C07D 409/04* (2006.01)
*C07D 409/14* (2006.01)
*C07D 413/06* (2006.01)
*C07D 413/14* (2006.01)

(52) U.S. Cl.
CPC ......... *C07D 495/04* (2013.01); *C07D 333/70* (2013.01); *C07D 409/04* (2013.01); *C07D 409/12* (2013.01); *C07D 409/14* (2013.01); *C07D 413/06* (2013.01); *C07D 413/14* (2013.01)

(58) Field of Classification Search
CPC .................................................... C07D 495/04
USPC .......................................................... 549/49
See application file for complete search history.

(56) References Cited

U.S. PATENT DOCUMENTS

| 5,210,090 A | 5/1993 | Desai et al. |
| 2005/0143422 A1 | 6/2005 | Levin et al. |
| 2014/0072630 A1 | 3/2014 | Tao et al. |

FOREIGN PATENT DOCUMENTS

| WO | 2004/018461 A2 | 3/2004 |
| WO | 2008/124000 A2 | 10/2008 |
| WO | 2010/144404 A1 | 12/2010 |
| WO | 2014/196793 A1 | 12/2014 |

OTHER PUBLICATIONS

Chemical Abstract compounds, STN Express (RN 1223805-43-3 (Entered STN: May 16, 2010), RN 1223767-12-1 (Entered STN: May 16, 2010), RN 928747-36-8 (Entered STN: Mar. 30, 2007), and RN 928737-85-3 (Entered STN: Mar. 30, 2007).
International Search Report of PCT/KR2015/012920 dated Jun. 29, 2016.

*Primary Examiner* — Taofiq A Solola
(74) *Attorney, Agent, or Firm* — Sughrue Mion, PLLC

(57) ABSTRACT

A heterocyclic derivative represented by formula (I), or a pharmaceutically acceptable salt or a stereoisomer thereof, which has an inhibitory effect on the activation of STAT3 protein, and is useful for the prevention or treatment of diseases associated with the activation of STAT3 protein.

12 Claims, No Drawings

HETEROCYCLIC DERIVATIVES AND USE THEREOF

CROSS REFERENCE TO RELATED APPLICATIONS

This application is a National Stage of International Application No. PCT/KR2015/012920 filed Nov. 30, 2015, claiming priority based on Korean Patent Application No. 10-2014-0170860 filed Dec. 2, 2014, the contents of all of which are incorporated herein by reference in their entirety.

FIELD OF THE INVENTION

The present invention relates to novel heterocyclic compounds, uses thereof for the prevention or treatment of diseases associated with the activation of STAT proteins, particularly, STAT3 protein and pharmaceutical compositions comprising same.

BACKGROUND OF THE INVENTION

Signal transducer and activator of transcription (STAT) proteins are transcription factors which transduce signals from various extracellular cytokines and growth factors to a nucleus. Seven (7) subtypes of STAT proteins (i.e., STAT1, STAT2, STAT3, STAT4, STAT5a, STAT5b and STAT6) are currently known, and generally they consist of about 750-850 amino acids. In addition, each subtype of STAT proteins contains several conserved domains which play an important role in exhibiting the function of STAT proteins. Specifically, five (5) domains from N-terminus to C-terminus of STAT proteins have been reported including coiled-coiled domain, DNA binding domain, linker domain, SH2 domain and transactivation domain (TAD)). Further, X-ray crystalline structures of STAT1, STAT3, STAT4 and STAT5 have been reported since 1998 (Becker S et al., *Nature*, 1998, 394; Vinkemeier U et al., *Science*, 1998, 279; Chen X et al., *Cell*, 1998, 93; D. Neculai et al., *J. Biol. Chem.*, 2005, 280). In general, receptors to which cytokines and growth factors bind are categorized into Class I and Class II. IL-2, IL-3, IL-5, IL-6, IL-12, G-CSF, GM-CSF, LIF, thrombopoietin, etc., bind to Class I receptors, while INF-α, INF-γ, IL-10, etc., bind to Class II receptors (Schindler C et al., *Annu. Rev. Biochem.*, 1995, 64; Novick D et al., *Cell*, 1994, 77; Ho A S et al., *Proc. Natl. Acad. Sci.*, 1993, 90). Among them, the cytokine receptors involved in the activation of STAT proteins can be classified depending on their structural forms of extracellular domains into a gp-130 family, an IL-2 family, a growth factor family, an interferon family and a receptor tyrosine kinase family. Interleukin-6 family cytokines are representative multifunctional cytokines which mediate various physiological activities. When interleukin-6 cytokine binds to IL-6 receptor which is present on the cell membrane surface, it attracts gp-130 receptor to form an IL-6-gp-130 receptor complex. At the same time, JAK kinases (JAK1, JAK2, JAK3 and Tyk2) in the cytoplasm are recruited to a cytoplasmic region of gp130 to be phosphorylated and activated. Subsequently, latent cytoplasmic STAT proteins are attracted to a receptor, phosphorylated by JAK kinases and activated. Tyrosine-705 adjacent to the SH2 domain located in the C-terminus of STAT proteins is phosphorylated, and the activated tyrosine-705 of each STAT protein monomer binds to the SH2 domain of another monomer in a reciprocal manner, thereby forming a homo- or heterodimer. The dimers are translocalized into a nucleus and bind to a specific DNA binding promoter to promote the transcription. Through its transcription process, various proteins (Myc, Cyclin D1/D2, Bcl-xL, Mcl, survivin, VEGF, HIF-1, immune suppressors, etc.) associated with cell proliferation, survival, angiogenesis and immune evasion are produced (Stark et al., *Annu. Rev. Biochem.*, 1997, 67; Levy et al., *Nat. Rev. Mol. Cell* Biol., 2002, 3).

In particular, STAT3 protein is known to play a crucial role in the acute inflammatory response and the signal transduction pathway of IL-6 and EGF (Akira et al., *Cell*, 1994, 76; Zhong et al., *Science*, 1994, 264). According to the recent clinical report, STAT3 protein is constantly activated in patients with solid cancers occurring in prostate, stomach, breast, lung, pancreas, kidney, uterine, ovary, head and neck, etc., and also in patients with blood cancer such as acute and chronic leukemia, multiple myeloma, etc. Further, it has been reported that the survival rate of a patient group with activated STAT3 is remarkably lower than that of a patient group with inactivated STAT3 (Masuda et al., *Cancer Res.*, 2002, 62; Benekli et al., *Blood*, 2002, 99; Yuichi et al., *Int. J. Oncology*, 2007, 30). Meanwhile, STAT3 was identified to be an essential factor for the growth and maintenance of murine embryonic stem cells in a study employing a STAT3 knockout mouse model. Also, a study with a tissue-specific STAT3-deficient mouse model reveals that STAT3 plays an important role in cell growth, apoptosis, and cell motility in a tissue-specific manner (Akira et al., *Oncogene* 2000, 19). Moreover, since apoptosis induced by anti-sensing STAT3 was observed in various cancer cell lines, STAT3 is considered as a promising new anticancer target. STAT3 is also considered as a potential target in the treatment of patients with diabetes, immune-related diseases, hepatitis C, macular degeneration, human papillomavirus infection, non-Hodgkin's lymphoma, tuberculosis, etc. Meanwhile, newly identified Th17 cells have been reported through a number of recent articles to be associated with various autoimmune diseases (Jacek Tabarkiewicz et al., Arch. Immunol. Ther. Exp., 2015, 11). Based on these reports, a control of the differentiation and function of Th17 cells is considered as a good target in the treatment of related diseases. In particular, since STAT3-dependent IL-6 and IL-23 signal transductions are known as important factors in the differentiation of Th17 cells (Xuexian O. Yang et al., J. Biol. Chem., 2007, 282; Harris T J et al., J. Immunol., 2007, 179), an inhibition of the function of STAT3 is expected to be effective in the treatment of diseases associated with Th17 cells such as systemic lupus erythematosus, uveitis, rheumatoid arthritis, autoimmune thyroid disease, inflammatory bowel disease, psoriasis and psoriatic arthritis (Jacek Tabarkiewicz et al., Arch. Immunol. Ther. Exp., 2015, 11).

Recently, IL-6 and IL-23 antibodies are under clinical studies on the treatment of arthritis and psoriasis associated with Th17 cells and exhibit a clinical efficacy (Nishimoto N. et al., Arthritis Rheum., 2004, 50; Gerald G. et al., N. Engl. J. Med., 2007, 356). This also confirms that the inhibition of STAT3 signal transduction is an effective therapeutic method for such diseases.

In contrast, while having intracellular response pathways of identical cytokines and growth factors to those of STAT3, STAT1 increases inflammation and congenital and acquired immunities to inhibit the proliferation of cancer cells or cause pro-apoptotic responses, unlike STAT3 (Valeria Poli et al., *Review, Landes Bioscience*, 2009).

In order to develop STAT3 inhibitors, the following methods can be considered: i) inhibition of the phosphorylation of STAT3 protein by IL-6/gp-130/JAK kinase, ii) inhibition of the dimerization of activated STAT3 proteins, and iii) inhibition of the binding of STAT3 dimer to nuclear DNA. Small molecular STAT3 inhibitors are currently under development. Specifically, OPB-31121 and OPB-51602 are under clinical studies on patients with solid cancers or blood cancers by Otsuka Pharmaceutical Co., Ltd. Further, S3I-201 (Siddiquee et al., *Proc. Natl. Acad. Sci.*, 2007, 104), S3I-M2001 (Siddiquee et al., *Chem. Biol.*, 2007, 2), LLL-12 (Lin et al., *Neoplasia*, 2010, 12), Stattic (Schust et al., *Chem. Biol.* 2006, 13), STA-21 (Song et al., *Proc. Natl. Acad. Sci.*, 2005, 102), SF-1-066 (Zhang et al., *Biochem. Pharm.*, 2010, 79) and STX-0119 (Matsuno et al., *ACS Med. Chem. Lett.*, 2010, 1), etc. have been reported to be effective in a cancer cell growth inhibition experiment and in animal model (in vivo Xenograft model). Furthermore, although peptide compounds mimicking the sequence of amino acid of pY-705 (STAT3) adjacent to the binding site to SH2 domain or the amino acid sequence of gp-130 receptor in which JAK kinases bind were studied (Coleman et al., *J. Med. Chem.*, 2005, 48), the development of the peptide compounds has not been successful due to the problems such as solubility and membrane permeability.

SUMMARY OF THE INVENTION

Accordingly, it is an object of the present invention to provide novel heterocyclic derivatives for the inhibition of the activation of STAT3 protein.

It is another object of the present invention to provide uses of the heterocyclic derivatives for the prevention or treatment of diseases associated with the activation of STAT3 protein.

In accordance with one aspect of the present invention, there is provided a compound selected from the group consisting of a heterocyclic derivative represented by formula (I), and a pharmaceutically acceptable salt and a stereoisomer thereof:

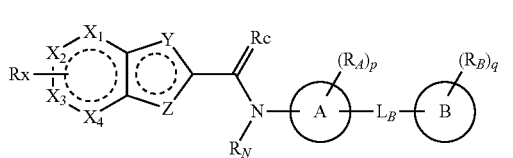

(I)

wherein one of $X_1$, $X_2$, $X_3$ and $X_4$ is —C(-Rx)=, and the others are each independently —C(-Rx')= or —N=;

one of Y and Z is —S— or —NH—, and the other is —CH= or —N=;

Rx is

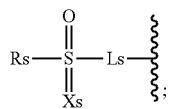

Xs is =O or =NH;

Ls is —C(-Rs')(-Rs")— or —N(-Rs')—;

Rs is $C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, amino$C_{1-6}$alkyl or 5- to 10-membered heterocyclyl, or Rs is linked to Rs' to form a chain;

Rs' and Rs" are each independently hydrogen, halogen, $C_{1-6}$alkyl, carbamoyl-$C_{1-6}$alkyl, $C_{1-6}$alkylamino-$C_{1-6}$alkyl or di$C_{1-6}$alkylamino-$C_{1-6}$alkyl, or Rs' and Rs" are linked together to form a chain, or Rs' is linked to Rs to form a chain;

Rx' is each independently hydrogen, halogen, nitro, amino, $C_{1-6}$alkoxy, halo$C_{1-6}$alkoxy, or $C_{1-6}$alkylsulfonyl;

A and B are each independently a monocyclic- or bicyclic-saturated or unsaturated $C_{3-10}$carbocycle or 5- to 12-membered heterocycle;

Rc is =O, =NH, =N(—$C_{1-6}$alkyl), or =N(—OH);

$R_N$ is hydrogen or $C_{1-6}$alkyl, or $R_N$ is linked to $R_A$ to form a chain;

$L_B$ is —[C(—$R_L$)(—$R_L'$)]$_m$—, —[C(—$R_L$)(—$R_L'$)]$_n$—O—, —O—, —NH—, —N($C_{1-6}$alkyl)-, —S(=O)$_2$—, —C(=O)—, or —C(=CH$_2$)—, wherein m is an integer of 0 to 3, n is an integer of 1 to 3, $R_L$ and $R_L'$ are each independently hydrogen, hydroxy, halogen or $C_{1-6}$alkyl, or $R_L$ and $R_L'$ are linked together to form a chain;

$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$alkoxy, cyano$C_{1-6}$alkoxy, $C_{1-6}$alkylamino, di$C_{1-6}$alkylamino, $C_{1-6}$alkylaminocarbonyl, di$C_{1-6}$alkylaminocarbonyl, $C_{2-8}$alkynyl, $C_{1-6}$alkoxycarbonylamino-$C_{1-6}$alkoxy, amino$C_{1-6}$alkoxy or 3- to 6-membered heterocyclyl, or $R_A$ is linked to $R_N$ to form a chain;

$R_B$ is hydrogen, halogen, hydroxy, cyano, nitro, amino, oxo, aminosulfonyl, sulfonylamido, $C_{1-6}$alkylamino, $C_{1-6}$alkyl, cyano$C_{1-6}$alkyl, $C_{1-6}$alkoxy, halo$C_{1-6}$alkoxy, cyano$C_{1-6}$alkoxy, $C_{3-8}$cyclcoalkyloxy, $C_{2-8}$alkenyl, $C_{2-8}$alkenyloxy, $C_{2-8}$alkynyl, $C_{2-8}$alkynyloxy, $C_{1-6}$alkylamino-$C_{1-6}$alkoxy, di$C_{1-6}$alkyl amino-$C_{1-6}$alkoxy, $C_{1-6}$alkoxycarbonyl, carbamoyl, carbamoyl-$C_{1-6}$alkoxy, $C_{1-6}$alkylthio, $C_{1-6}$alkylsulfinyl, $C_{1-6}$alkylsulfonyl, 5- to 10-membered heterocyclyl, 5- to 10-membered heterocyclyl-$C_{1-6}$alkyl, 5- to 10-membered heterocyclyl-$C_{1-6}$alkoxy, or 5- to 10-membered heterocyclyl-oxy;

p is an integer of 0 to 4, and, when p is 2 or higher, $R_A$ moieties are the same as or different from each other;

q is an integer of 0 to 4, and, when q is 2 or higher, $R_B$ moieties are the same as or different from each other; and each of said chains is independently a saturated or unsaturated $C_{2-10}$ hydrocarbon chain not containing or containing at least one heterogroup selected from the group consisting of —O—, —NH—, —N=, —S—, —S(=O)— and —S(=O)$_2$— in the chain, and unsubstituted or substituted with at least one selected from the group consisting of halogen, $C_{1-6}$alkyl and $C_{1-6}$alkoxy; and each of said heterocycle and heterocyclyl moieties independently contains at least one heterogroup selected from the group consisting of —O—, —NH—, —N=, —S—, —S(=O)— and —S(=O)$_2$—.

In accordance with another aspect of the present invention, there is provided a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

In accordance with a further aspect of the present invention, there is provided a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

In accordance with a still further aspect of the present invention, there is provided a method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

The heterocyclic derivative represented by formula (I) above, or a pharmaceutically acceptable salt or a stereoisomer thereof has an excellent inhibitory effect on the activation of STAT3 protein, and thus it can be used for the prevention or treatment of diseases associated with the activation of STAT3 protein.

DETAILED DESCRIPTION OF THE INVENTION

The present invention will be further described in detail herein below.

In the specification of the present invention, the term "halogen" refers to fluoro, chloro, bromo or iodo, unless specified otherwise.

The term "alkyl" refers to a linear or branched hydrocarbon moiety, unless specified otherwise.

The terms "haloalkyl", "haloalkoxy", "halophenyl", etc., respectively refer to alkyl, alkoxy, and phenyl substituted with at least one halogen.

The term "carbocycle" refers to an aromatic or non-aromatic hydrocarbon ring, which may be saturated or unsaturated, and a monocyclic or polycyclic radical. The term "carbocyclyl" refers to a radical of "carbocycle", and is used as a term inclusive of "cycloalkyl" and "aryl". The term "cycloalkyl" refers to a saturated hydrocarbon radical, which may be monocyclic or polycyclic. The term "aryl" refers to an aromatic hydrocarbon ring, which may be monocyclic or polycyclic.

The terms "carbocycle", "carbocyclyl", "cycloalkyl" and "aryl" may refer to, for example, a monocycle or polycycle having 3 to 20 carbon atoms, and will be indicated as "$C_{3-20}$ carbocycle", "$C_{3-20}$ carbocyclyl", "$C_{3-20}$ cycloalkyl", and "$C_{3-20}$ aryl", respectively.

The term "heterocycle" refers to an aromatic or non-aromatic ring having at least one heteroatom, which may be saturated or unsaturated, and a monocycle or polycycle. The term "heterocyclyl" refers to a radical of "heterocycle", which is used as a term inclusive of "heterocycloalkyl" and "heteroaryl". The term "heterocycloalkyl" refers to a saturated ring radical having at least one heteroatom, which may be monocyclic or polycyclic. The term "heteroaryl" refers to an aromatic ring radical having at least one heteroatom, which may be monocyclic or polycyclic.

The term "heteroatom" may be selected from N, O and S.

The terms "heterocycle", "heterocyclyl", "heterocycloalkyl" and "heteroaryl" may refer to, for example, a mono- or polycycle having 3 to 20 heteroatoms and/or carbon atoms, and will be indicated as "3- to 20-membered heterocycle", "3- to 20-membered heterocyclyl", "3- to 20-membered heterocycloalkyl", and "3- to 20-membered heteroaryl".

The term "chain" refers to a saturated or unsaturated $C_{2-10}$ hydrocarbon chain not containing any heteroatoms in the chain, for example, ethylene, propylene, butylene and —$CH_2$—CH=CH—; or a saturated or unsaturated $C_{2-10}$ hydrocarbon chain containing at least one heterogroup selected from the group consisting of —O—, —NH—, —N=, —S—, —S(=O)— and —S(=O)$_2$— in the chain, for example, —$CH_2$—O—$CH_2$—, —$CH_2$—O—$CH_2$—O—$CH_2$—, —$CH_2$—CH=CH—NH— and —$CH_2$—$CH_2$—S(=O)$_2$—$CH_2$—O—, unless specified otherwise. The chain may be substituted with at least one selected from the group consisting of halogen, $C_{1-6}$alkyl and $C_{1-6}$alkoxy.

In accordance with one aspect of the present invention, there is provided a compound selected from the group consisting of a heterocyclic derivative represented by formula (I), and a pharmaceutically acceptable salt and a stereoisomer thereof:

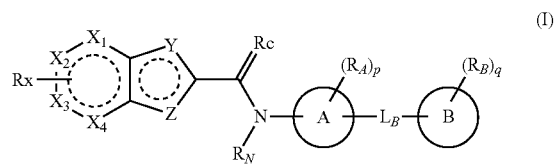

(I)

wherein one of $X_1$, $X_2$, $X_3$ and $X_4$ is —C(-Rx)=, and the others are each independently —C(-Rx')= or —N=;

one of Y and Z is —S— or —NH—, and the other is —CH= or —N=;

Rx is

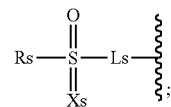

$Xs$ is =O or =NH;

$Ls$ is —C(—Rs')(-Rs")- or —N(-Rs')-;

Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, amino $C_{1-6}$alkyl or 5- to 10-membered heterocyclyl, or Rs is linked to Rs' to form a chain;

Rs' and Rs" are each independently hydrogen, halogen, $C_{1-6}$alkyl, carbamoyl-$C_{1-6}$alkyl, $C_{1-6}$alkylamino-$C_{1-6}$alkyl or di$C_{1-6}$alkylamino-$C_{1-6}$alkyl, or Rs' and Rs" are linked together to form a chain, or Rs' is linked to Rs to form a chain;

Rx' is each independently hydrogen, halogen, nitro, amino, $C_{1-6}$alkoxy, halo$C_{1-6}$alkoxy, or $C_{1-6}$alkylsulfonyl;

A and B are each independently a monocyclic- or bicyclic-saturated or unsaturated $C_{3-10}$carbocycle or 5- to 12-membered heterocycle;

Rc is =O, =NH, =N(—$C_{1-6}$alkyl), or =N(—OH);

$R_N$ is hydrogen or $C_{1-6}$alkyl, or $R_N$ is linked to $R_A$ to form a chain;

$L_B$ is —[C(—$R_L$)(—$R_L$')]$_m$—, —[C(—$R_L$)(—$R_L$')]$_n$—O—, —O—, —NH—, —N($C_{1-6}$alkyl)-, —S(=O)$_2$—, —C(=O)—, or —C(=CH$_2$)—, wherein m is an integer of 0 to 3, n is an integer of 1 to 3, $R_L$ and $R_L$' are each independently hydrogen, hydroxy, halogen or $C_{1-6}$alkyl, or $R_L$ and $R_L$' are linked together to form a chain;

$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$alkoxy, cyano$C_{1-6}$alkoxy, $C_{1-6}$alkylamino, di$C_{1-6}$alkylamino, $C_{1-6}$alkylthio, $C_{1-6}$alkylaminocarbonyl, di$C_{1-6}$alkylaminocarbonyl, $C_{2-8}$alkynyl, $C_{1-6}$ alkoxycarbonylamino-$C_{1-6}$alkoxy, amino$C_{1-6}$alkoxy or 3- to 6-membered heterocyclyl, or $R_A$ is linked to $R_N$ to form a chain;

$R_B$ is hydrogen, halogen, hydroxy, cyano, nitro, amino, oxo, aminosulfonyl, sulfonylamido, $C_{1-6}$alkylamino, $C_{1-6}$alkyl, halo$C_{1-6}$alkyl, cyano$C_{1-6}$alkyl, $C_{1-6}$alkoxy, halo $C_{1-6}$alkoxy, cyano$C_{1-6}$alkoxy, $C_{3-8}$cyclcoalkyloxy, $C_{2-8}$alkenyl, $C_{2-8}$alkenyloxy, $C_{2-8}$alkynyl, $C_{2-8}$alkynyloxy, $C_{1-6}$alkylamino-$C_{1-6}$alkoxy, di$C_{1-6}$alkylamino-$C_{1-6}$alkoxy, $C_{1-6}$alkoxycarbonyl, carbamoyl, carbamoyl-$C_{1-6}$alkoxy, $C_{1-6}$alkylthio, $C_{1-6}$alkylsulfinyl, $C_{1-6}$alkylsulfonyl, 5- to 10-membered heterocyclyl, 5- to 10-membered heterocyclyl-$C_{1-6}$alkyl, 5- to 10-membered heterocyclyl-$C_{1-6}$alkoxy, or 5- to 10-membered heterocyclyl-oxy;

p is an integer of 0 to 4, and, when p is 2 or higher, $R_A$ moieties are the same as or different from each other;

q is an integer of 0 to 4, and, when q is 2 or higher, $R_B$ moieties are the same as or different from each other; and each of said chains is independently a saturated or unsaturated $C_{2-10}$ hydrocarbon chain not containing or containing at least one heterogroup selected from the group consisting of —O—, —NH—, —N=, —S—, —S(=O)— and —S(=O)$_2$— in the chain, and unsubstituted or substituted with at least one selected from the group consisting of halogen, $C_{1-6}$alkyl and $C_{1-6}$alkoxy; and each of said heterocycle and heterocyclyl moieties independently contains at least one heterogroup selected from the group consisting of —O—, —NH—, —N=, —S—, —S(=O)— and —S(=O)$_2$—.

In a preferred embodiment of the compound of formula (I), one of $X_2$ and $X_3$ is —C(-Rx)=, and the other is —C(-Rx')= or —N=;

$X_1$ and $X_4$ are each independently —C(-Rx')= or —N=;

one of Y and Z is —S— or —NH—, and the other is —CH=;

Rx and Rx' are the same as defined above in formula (I); and

Rc, $R_N$, A, B, $L_B$, $R_A$, $R_B$, p and q are the same as defined above in formula (I).

In a preferred embodiment of the compound of formula (I), one of $X_2$ and $X_3$ is —C(-Rx)=, and the other is —C(-Rx')= or —N=;

$X_1$ and $X_4$ are each independently —C(-Rx')= or —N=;

one of Y and Z is —S— or —NH—, and the other is —CH=;

Rx is

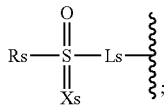

Xs is =O or =NH;

Ls is —C(—Rs')(-Rs")- or —N(-Rs')-;

Rs is $C_{1-6}$alkyl, halo$C_{1-6}$alkyl, $C_{1-6}$alkoxy-$C_{1-6}$alkyl or 5- to 6-membered heterocyclyl, or Rs is linked to Rs' to form a chain;

Rs' and Rs" are each independently hydrogen, halogen or $C_{1-6}$alkyl, or Rs' and Rs" are linked together to form a chain, or Rs' is linked to Rs to form a chain;

Rx' is each independently hydrogen or halogen;

each of said chains is independently a saturated or unsaturated $C_{2-7}$ hydrocarbon chain not containing or containing at least one heteroatom selected from the group consisting of O, N and S; and Rc, $R_N$, A, B, $L_B$, $R_A$, $R_B$, p and q are the same as defined above in formula (I).

In a preferred embodiment of the compound of formula (I), one of $X_2$ and $X_3$ is —C(-Rx)=, and the other is —C(-Rx')= or $X_1$ and $X_4$ are each independently —C(-Rx')= or —N=;

one of Y and Z is —S— or —NH—, and the other is —CH=;

Rx is

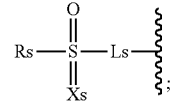

Xs is =O or =NH;

Ls is —C(—Rs')(-Rs")- or —N(-Rs')-;

Rs is $C_{1-6}$alkyl, halo$C_{1-6}$alkyl, $C_{1-6}$alkoxy-$C_{1-6}$alkyl or 5- to 6-membered heterocyclyl, or Rs is linked to Rs' to form a chain;

Rs' and Rs" are each independently hydrogen, halogen or $C_{1-6}$alkyl, or Rs' and Rs" are linked together to form a chain, or Rs' is linked to Rs to form a chain;

Rx' is each independently hydrogen or halogen;

each of said chains is independently a saturated or unsaturated $C_{2-7}$ hydrocarbon chain not containing or containing at least one heteroatom selected from the group consisting of O, N and S;

Rc and $R_N$ are the same as defined above in formula (I);

A is benzene or a 5- to 10-membered heteroaryl containing 1 to 3 nitrogen atoms;

B is a monocyclic- or bicyclic-saturated or unsaturated $C_{6-10}$carbocycle or 5- to 10-membered heterocycle;

$L_B$ is —[C(—$R_L$)(—$R_L$)]$_m$—, —O—, —NH—, or —N($C_{1-6}$alkyl)-, wherein m is 0 or 1, $R_L$ and $R_L$' are each independently hydrogen, hydroxy, halogen or $C_{1-6}$alkyl, or $R_L$ and $R_L$' are linked together to form $C_{2-5}$alkylene;

$R_A$ is halogen, $C_{1-6}$alkoxycarbonylamino-$C_{1-6}$alkoxy, amino$C_{1-6}$alkoxy, or 3- to 6-membered heterocyclyl;

$R_B$ is halogen, $C_{1-6}$alkyl, $C_{1-6}$alkoxy, halo$C_{1-6}$alkyloxy, $C_{2-6}$alkenyloxy, $C_{2-6}$alkynyloxy, $C_{1-6}$alkoxycarbonyl, $C_{3-10}$carbocyclyl-oxy, or 3- to 10-membered heterocyclyl-$C_{1-3}$alkoxy; and each of said heteroaryl, heterocycle and heterocyclyl moieties independently contains 1 to 3 heteroatoms selected from the group consisting of O, N and S.

In a preferred embodiment of the compound of formula (I), $X_1$ and $X_4$ are —CH=;

$X_2$ is —C(-Rx)=;

$X_3$ is —N= or —C(-Rx')-;

Y is —C;

Z is —S—;

Rx is

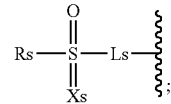

Ls is —C(—CH$_3$)(—CH$_3$)—;

Rs is $C_{1-6}$alkyl, halo$C_{1-6}$alkyl, $C_{1-6}$alkoxy$C_{1-6}$ alkyl, $C_{1-6}$alkylcarbonyl$C_{1-6}$alkyl, $C_{2-7}$alkenyl, amino, amino$C_{1-6}$alkyl, or a 5- to 10-membered heterocyclyl containing 1 to 3 heteroatoms selected from the group consisting of O, N and S;

Rx' is hydrogen, halogen, nitro, amino, $C_{1-6}$alkoxy, halo$C_{1-6}$alkoxy, or $C_{1-6}$alkylsulfonyl;

Rc is =O;

$R_N$ is hydrogen; and

A, B, $L_B$, $R_A$, $R_B$, p and q are the same as defined above in formula (I).

In a preferred embodiment of the compound of formula (I), $X_1$, $X_3$ and $X_4$ are —CH=;

$X_2$ is —C(-Rx)=;

Y is —C=;

Z is —S—;

Rx is

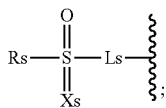

Ls is —C(—Rs')(-Rs")-;

Xs is =O or =NH;

Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, amino$C_{1-6}$alkyl, or a 5- to 10-membered heterocyclyl containing 1 to 3 heteroatoms selected from the group consisting of O, N and S;

Rs' and Rs" are each independently hydrogen, halogen, $C_{1-6}$alkyl, carbamoyl$C_{1-6}$alkyl, $C_{1-6}$alkylamino-$C_{1-6}$alkyl or di$C_{1-6}$alkylamino-$C_{1-6}$alkyl, or Rs' and Rs" are linked together to form a chain, wherein the chain is a saturated or unsaturated $C_{2-10}$ hydrocarbon chain not containing or containing at least one heterogroup selected from the group consisting of —O—, —NH—, —N=, —S—, —S(=O)— and —S(=O)$_2$— in the chain, and unsubstituted or substituted with at least one selected from the group consisting of halogen, $C_{1-6}$alkyl and $C_{1-6}$alkoxy;

Rc is =O;

$R_N$ is hydrogen; and

A, B, $L_B$, $R_A$, $R_B$, p and q are the same as defined above in formula (I).

In a preferred embodiment of the compound of formula (I), $X_1$, $X_3$ and $X_4$ are —CH=;

$X_2$ is —C(-Rx)=;

Y is —C=;

Z is —S—;

Rx is the same as defined above in formula (I);

Rc is =O;

$R_N$ is hydrogen; and

A, B, $L_B$, $R_A$, $R_B$, p and q are the same as defined above in formula (I).

In a preferred embodiment of the compound of formula (I), $X_1$, $X_2$ and $X_4$ are —CH=;

$X_3$ is —C(-Rx)=;

Y is —C=;

Z is —S— or —NH—;

Rx is

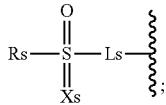

Xs is =O;

Ls is —C(—CH$_3$)(—CH$_3$)—;

Rs is methyl;

Rc is =O;

$R_N$ is hydrogen; and

A, B, $L_B$, $R_A$, $R_B$, p and q are the same as defined above in formula (I).

In a preferred embodiment of the compound of formula (I), if A is 5-membered heterocycle, m is an integer of 1 to 3. The 5-membered heterocycle is preferably a 5-membered aromatic ring unsubstituted or substituted with at least one selected from the group consisting of halogen, $C_{1-10}$alkyl and halo$C_{1-10}$alkyl. The 5-membered heterocycle contains at least one heteroatom selected from the group consisting of N, S and O.

Preferable examples of the compound according to the present invention are listed below, and a pharmaceutically acceptable salt and a stereoisomer thereof are also included in the scope of the present invention:

1) N-(3-chloro-5-(2-(3-ethoxy-5-(trifluoromethoxy)phenyl)propan-2-yl)phenyl)-5-(2-(methylsulfonyl)propan-2-yl)benzo[b]thiophene-2-carboxamide;

2) N-(3-chloro-5-(2-(3-propoxy-5-(trifluoromethoxy)phenyl)propan-2-yl)phenyl)-5-(2-(methylsulfonyl)propan-2-yl)benzo[b]thiophene-2-carboxamide;

3) N-(3-(2-(3-methoxy-5-(trifluoromethoxy)phenyl)propan-2-yl)phenyl)-5-(2-(methylsulfonyl)propan-2-yl)benzo[b]thiophene-2-carboxamide;

4) N-(3-bromo-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide;

5) N-(3-chloro-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide;

6) N-(3-methoxy-5-(2-(3-methoxy-5-(trifluoromethoxy)phenyl)propan-2-yl)phenyl)-5-(2-(methylsulfonyl)propan-2-yl)benzo[b]thiophene-2-carboxamide;

7) N-(3-chloro-5-(2-(3-methoxy-5-(trifluoromethoxy)phenyl)propan-2-yl)phenyl)-5-(2-(methylsulfonyl)propan-2-yl)benzo[b]thiophene-2-carboxamide;

8) N-(3-chloro-5-(2-(3-(2-morpholinoethoxy)-5-(trifluoromethoxy)phenyl)propan-2-yl)phenyl)-5-(2-(methylsulfonyl)propan-2-yl)benzo[b]thiophene-2-carboxamide;

9) N-(3-bromo-5-(2-(3-isopropoxy-5-(trifluoromethoxy)phenyl)propan-2-yl)phenyl)-5-(2-(methylsulfonyl)propan-2-yl)benzo[b]thiophene-2-carboxamide;

10) N-(3-(2-(3-(but-2-yn-1-yloxy)-5-(trifluoromethoxy)phenyl)propan-2-yl)-5-chlorophenyl)-5-(2-(methylsulfonyl)propan-2-yl)benzo[b]thiophene-2-carboxamide;

11) N-(3-chloro-5-(2-(3-isobutoxy-5-(trifluoromethoxy)phenyl)propan-2-yl)phenyl)-5-(2-(methylsulfonyl)propan-2-yl)benzo[b]thiophene-2-carboxamide;

12) N-(3-chloro-5-(2-(3-(2,2,2-trifluoroethoxy)-5-(trifluoromethoxy)phenyl)propan-2-yl)phenyl)-5-(2-(methylsulfonyl)propan-2-yl)benzo[b]thiophene-2-carboxamide;

13) N-(3-chloro-5-(2-(3-(2,2-difluoroethoxy)-5-(trifluoromethoxy)phenyl)propan-2-yl)phenyl)-5-(2-(methylsulfonyl)propan-2-yl)benzo[b]thiophene-2-carboxamide;

14) N-(3-(2-(3-(allyloxy)-5-(trifluoromethoxy)phenyl)propan-2-yl)-5-chlorophenyl)-5-(2-(methylsulfonyl)propan-2-yl)benzo[b]thiophene-2-carboxamide;

15) N-(3-chloro-5-(2-(3-cyclopropoxy-5-(trifluoromethoxy)phenyl)propan-2-yl)phenyl)-5-(2-(methylsulfonyl)propan-2-yl)benzo[b]thiophene-2-carboxamide;

16) N-(3-chloro-5-(2-(3-isopropoxy-5-(trifluoromethoxy)phenyl)propan-2-yl)phenyl)-5-((methylsulfonyl)methyl)benzo[b]thiophene-2-carboxamide;

17) N-(3-chloro-5-(2-(4-methoxyphenyl)propan-2-yl)phenyl)-5-(2-(methylsulfonyl)propan-2-yl)benzo[b]thiophene-2-carboxamide;
18) N-(3-chloro-5-(2-(4-fluorophenyl)propan-2-yl)phenyl)-5-(2-(methylsulfonyl)propan-2-yl)benzo[b]thiophene-2-carboxamide;
19) N-(3-chloro-5-(2-(4-fluorophenyl)propan-2-yl)phenyl)-6-fluoro-5-(2-(methylsulfonyl)propan-2-yl)benzo[b]thiophene-2-carboxamide;
20) N-(3-bromo-5-(2-(4-fluorophenyl)propan-2-yl)phenyl)-5-(2-(methylsulfonyl)propan-2-yl)benzo[b]thiophene-2-carboxamide;
21) N-(3-chloro-5-(2-(4-chlorophenyl)propan-2-yl)phenyl)-5-((methylsulfonyl)methyl)benzo[b]thiophene-2-carboxamide;
22) N-(3-chloro-5-(2-(4-chlorophenyl)propan-2-yl)phenyl)-5-(2-(methylsulfonyl)propan-2-yl)benzo[b]thiophene-2-carboxamide;
23) 6-chloro-N-(3-chloro-5-(2-(4-chlorophenyl)propan-2-yl)phenyl)-5-(2-(methylsulfonyl)propan-2-yl)benzo[b]thiophene-2-carboxamide;
24) N-(3-chloro-5-(2-(4-chlorophenyl)propan-2-yl)phenyl)-5-(((trifluoromethyl)sulfonyl)methyl)benzo[b]thiophene-2-carboxamide;
25) N-(3-chloro-5-(2-(4-chlorophenyl)propan-2-yl)phenyl)-5-(fluoro(methylsulfonyl)methyl)benzo[b]thiophene-2-carboxamide;
26) N-(3-chloro-5-(2-(4-chlorophenyl)propan-2-yl)phenyl)-5-(2-(methylsulfonyl)propan-2-yl)thieno[2,3-c]pyridine-2-carboxamide;
27) N-(3-chloro-5-(2-(5-chlorothiophen-2-yl)propan-2-yl)phenyl)-5-(2-(methylsulfonyl)propan-2-yl)benzo[b]thiophene-2-carboxamide;
28) N-(3-chloro-5-(2-(5-isopropylthiophen-2-yl)propan-2-yl)phenyl)-5-(2-(methylsulfonyl)propan-2-yl)benzo[b]thiophene-2-carboxamide;
29) N-(3-chloro-5-(2-(5-methoxythiophen-2-yl)propan-2-yl)phenyl)-5-(2-(methylsulfonyl)propan-2-yl)benzo[b]thiophene-2-carboxamide;
30) N-(3-chloro-5-(2-(2-methoxythiophen-3-yl)propan-2-yl)phenyl)-5-(2-(methylsulfonyl)propan-2-yl)benzo[b]thiophene-2-carboxamide;
31) N-(3-chloro-5-(2-(1-methyl-1H-pyrrol-2-yl)propan-2-yl)phenyl)-5-(2-(methylsulfonyl)propan-2-yl)benzo[b]thiophene-2-carboxamide;
32) N-(3-chloro-5-(2-(4-methylthiophen-2-yl)propan-2-yl)phenyl)-5-(2-(methylsulfonyl)propan-2-yl)benzo[b]thiophene-2-carboxamide;
33) N-(3-chloro-5-(2-(4-chlorophenyl)propan-2-yl)phenyl)-5-(1-(methylsulfonyl)cyclopropyl)benzo[b]thiophene-2-carboxamide;
34) N-(3-chloro-5-(2-(4-chlorophenyl)propan-2-yl)phenyl)-5-(4-(methylsulfonyl)tetrahydro-2H-pyran-4-yl)benzo[b]thiophene-2-carboxamide;
35) N-(3-chloro-5-(2-(4-chlorophenyl)propan-2-yl)phenyl)-6-(2-(methylsulfonyl)propan-2-yl)-1H-indole-2-carboxamide;
36) N-(3-chloro-5-(2-(4-chlorophenyl)propan-2-yl)phenyl)-5-((S-methylsulfonimidoyl)methyl)benzo[b]thiophene-2-carboxamide;
37) N-(3-chloro-5-(4-(trifluoromethoxy)phenoxy)phenyl)-5-(2-(methylsulfonyl)propan-2-yl)benzo[b]thiophene-2-carboxamide;
38) N-(3-chloro-5-(4-(trifluoromethyl)phenoxy)phenyl)-5-(2-(methylsulfonyl)propan-2-yl)benzo[b]thiophene-2-carboxamide;
39) N-(3-bromo-5-(4-chlorophenoxy)phenyl)-5-(2-(methylsulfonyl)propan-2-yl)benzo[b]thiophene-2-carboxamide;
40) N-(3-chloro-5-(4-chlorophenoxy)phenyl)-6-(2-(methylsulfonyl)propan-2-yl)-1H-indole-2-carboxamide;
41) N-(3-chloro-5-(4-chlorophenoxy)phenyl)-5-((methylsulfonyl)methyl)benzo[b]thiophene-2-carboxamide;
42) N-(3-chloro-5-(4-chlorophenoxy)phenyl)-5-(((trifluoromethyl)sulfonyl)methyl)benzo[b]thiophene-2-carboxamide;
43) N-(3-chloro-5-(4-fluorophenoxy)phenyl)-5-(2-(methylsulfonyl)propan-2-yl)benzo[b]thiophene-2-carboxamide;
44) N-(3-chloro-5-(4-chlorophenoxy)phenyl)-6-fluoro-5-(2-(methylsulfonyl)propan-2-yl)benzo[b]thiophene-2-carboxamide;
45) 6-chloro-N-(3-chloro-5-(4-chlorophenoxy)phenyl)-5-(2-(methylsulfonyl)propan-2-yl)benzo[b]thiophene-2-carboxamide;
46) N-(3-(4-chlorophenoxy)-5-methoxyphenyl)-5-(2-(methylsulfonyl)propan-2-yl)benzo[b]thiophene-2-carboxamide;
47) N-(3-chloro-5-(3-chloro-5-fluorophenoxy)phenyl)-5-(2-(methylsulfonyl)propan-2-yl)benzo[b]thiophene-2-carboxamide;
48) N-(3-chloro-5-(3-(trifluoromethoxy)phenoxy)phenyl)-5-(2-(methylsulfonyl)propan-2-yl)benzo[b]thiophene-2-carboxamide;
49) N-(3-chloro-5-(4-chlorophenoxy)phenyl)-5-(2-(methylsulfonyl)propan-2-yl)benzo[b]thiophene-2-carboxamide;
50) N-(3-chloro-5-(4-chlorophenoxy)phenyl)-5-(2-(methylsulfonyl)propan-2-yl)thieno[2,3-c]pyridine-2-carboxamide;
51) N-(3-chloro-5-(3-chloro-4-fluorophenoxy)phenyl)-5-(2-(methylsulfonyl)propan-2-yl)benzo[b]thiophene-2-carboxamide;
52) N-(3-chloro-5-(3,4-difluorophenoxy)phenyl)-5-(2-(methylsulfonyl)propan-2-yl)benzo[b]thiophene-2-carboxamide;
53) N-(3-chloro-5-(3-fluoro-5-methoxyphenoxy)phenyl)-5-(2-(methylsulfonyl)propan-2-yl)benzo[b]thiophene-2-carboxamide;
54) N-(3-chloro-5-(4-chloro-3-fluorophenoxy)phenyl)-5-(2-(methylsulfonyl)propan-2-yl)benzo[b]thiophene-2-carboxamide;
55) N-(3-chloro-5-(2-(3-chloro-5-methoxyphenyl)propan-2-yl)phenyl)-5-(2-(methylsulfonyl)propan-2-yl)benzo[b]thiophene-2-carboxamide;
56) N-(3-chloro-5-(4-chlorophenoxy)phenyl)-5-(4-(methylsulfonyl)tetrahydro-2H-pyran-4-yl)benzo[b]thiophene-2-carboxamide;
57) N-(3-chloro-5-(4-chlorophenoxy)phenyl)-5-(2-((2-methoxyethyl)sulfonyl)propan-2-yl)benzo[b]thiophene-2-carboxamide;
58) N-(3-chloro-5-(4-chlorophenoxy)phenyl)-6-(2-(methylsulfonyl)propan-2-yl)benzo[b]thiophene-2-carboxamide;
59) N-(3-(azetidin-1-yl)-5-(4-chlorophenoxy)phenyl)-5-(2-(methylsulfonyl)propan-2-yl)benzo[b]thiophene-2-carboxamide;
60) N-(3-chloro-5-((6-chloropyridin-3-yl)oxy)phenyl)-5-(2-(methylsulfonyl)propan-2-yl)benzo[b]thiophene-2-carboxamide;
61) N-(3-chloro-5-((5-chloropyridin-2-yl)oxy)phenyl)-5-(2-(methylsulfonyl)propan-2-yl)benzo[b]thiophene-2-carboxamide;
62) N-(2-chloro-6-(3,5-dichlorophenoxy)pyridin-4-yl)-5-(2-(methylsulfonyl)propan-2-yl)benzo[b]thiophene-2-carboxamide;

63) N-(6-chloro-4-(4-chlorophenoxy)pyridin-2-yl)-5-(2-(methylsulfonyl)propan-2-yl)benzo[b]thiophene-2-carboxamide;
64) N-(2-chloro-6-(4-chlorophenoxy)pyridin-4-yl)-5-(2-(methylsulfonyl)propan-2-yl)benzo[b]thiophene-2-carboxamide;
65) N-(2-chloro-6-((6-chloropyridin-3-yl)oxy)pyridin-4-yl)-5-(2-(methylsulfonyl)propan-2-yl)benzo[b]thiophene-2-carboxamide;
66) N-(4-chloro-6-(4-chlorophenoxy)pyridin-2-yl)-5-(2-(methylsulfonyl)propan-2-yl)benzo[b]thiophene-2-carboxamide;
67) N-(2-chloro-6-(4-(trifluoromethyl)phenoxy)pyridin-4-yl)-5-(2-(methylsulfonyl)propan-2-yl)benzo[b]thiophene-2-carboxamide;
68) N-(2-chloro-6-(4-fluorophenoxy)pyridin-4-yl)-5-(2-(methylsulfonyl)propan-2-yl)benzo[b]thiophene-2-carboxamide;
69) N-(2-bromo-6-(4-chlorophenoxy)pyridin-4-yl)-5-(2-(methylsulfonyl)propan-2-yl)benzo[b]thiophene-2-carboxamide;
70) N-(2-chloro-6-(3-chloro-5-methoxyphenoxy)pyridin-4-yl)-5-(2-(methylsulfonyl)propan-2-yl)benzo[b]thiophene-2-carboxamide;
71) N-(2-chloro-6-(3-chloro-4-fluorophenoxy)pyridin-4-yl)-5-(2-(methylsulfonyl)propan-2-yl)benzo[b]thiophene-2-carboxamide;
72) N-(2-chloro-6-(4-chloro-3-fluorophenoxy)pyridin-4-yl)-5-(2-(methylsulfonyl)propan-2-yl)benzo[b]thiophene-2-carboxamide;
73) N-(2-chloro-6-(4-chlorophenoxy)pyridin-4-yl)-5-(1,1-dioxidotetrahydrothiophen-2-yl)benzo[b]thiophene-2-carboxamide;
74) N-(2-chloro-6-(4-chlorophenoxy)pyridin-4-yl)-5-(1,1-dioxidotetrahydro-2H-thiopyran-2-yl)benzo[b]thiophene-2-carboxamide;
75) N-(2-chloro-6-(4-chlorophenoxy)pyrimidin-4-yl)-5-(2-(methylsulfonyl)propan-2-yl)benzo[b]thiophene-2-carboxamide;
76) N-(6-chloro-2-(4-chlorophenoxy)pyrimidin-4-yl)-5-(2-(methylsulfonyl)propan-2-yl)benzo[b]thiophene-2-carboxamide;
77) N-(2-(4-chlorophenoxy)-6-fluoropyridin-4-yl)-5-(2-(methylsulfonyl)propan-2-yl)benzo[b]thiophene-2-carboxamide;
78) N-(2-(bicyclo[2.2.1]hept-5-en-2-yloxy)-6-chloropyridin-4-yl)-5-(2-(methylsulfonyl)propan-2-yl)benzo[b]thiophene-2-carboxamide;
79) N-(2-chloro-6-(3,4-difluorophenoxy)pyridin-4-yl)-5-(2-(methylsulfonyl)propan-2-yl)benzo[b]thiophene-2-carboxamide;
80) N-(2-chloro-6-(3-chlorophenoxy)pyridin-4-yl)-5-(2-(methylsulfonyl)propan-2-yl)benzo[b]thiophene-2-carboxamide;
81) N-(2-chloro-6-(3-(trifluoromethoxy)phenoxy)pyridin-4-yl)-5-(2-(methylsulfonyl)propan-2-yl)benzo[b]thiophene-2-carboxamide;
82) N-(2-chloro-6-(3,4-dichlorophenoxy)pyridin-4-yl)-5-(2-(methylsulfonyl)propan-2-yl)benzo[b]thiophene-2-carboxamide;
83) N-(2-chloro-6-(4-chloro-2-fluorophenoxy)pyridin-4-yl)-5-(2-(methylsulfonyl)propan-2-yl)benzo[b]thiophene-2-carboxamide;
84) N-(2-chloro-6-(4-(trifluoromethoxy)phenoxy)pyridin-4-yl)-5-(2-(methylsulfonyl)propan-2-yl)benzo[b]thiophene-2-carboxamide;
85) N-(2-chloro-6-((5-chloropyridin-2-yl)oxy)pyridin-4-yl)-5-(2-(methylsulfonyl)propan-2-yl)benzo[b]thiophene-2-carboxamide;
86) N-(2-chloro-6-((4-chlorobenzyl)oxy)pyridin-4-yl)-5-(2-(methylsulfonyl)propan-2-yl)benzo[b]thiophene-2-carboxamide;
87) N-(3-chloro-5-(2-(3-(prop-1-yn-1-yl)-5-(trifluoromethoxy)phenyl)propan-2-yl)phenyl)-5-(2-(methylsulfonyl)propan-2-yl)benzo[b]thiophene-2-carboxamide;
88) N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide;
89) N-(3-(2-(4-chlorophenyl)propan-2-yl)-1H-pyrazol-5-yl)-5-(2-(methylsulfonyl)propan-2-yl)benzo[b]thiophene-2-carboxamide;
90) N-(2-chloro-6-(2-(3-methoxy-5-(trifluoromethoxy)phenyl)propan-2-yl)pyridin-4-yl)-5-(2-(methylsulfonyl)propan-2-yl)benzo[b]thiophene-2-carboxamide;
91) N-(4-chloro-6-(2-(3-methoxy-5-(trifluoromethoxy)phenyl)propan-2-yl)pyridin-2-yl)-5-(2-(methylsulfonyl)propan-2-yl)benzo[b]thiophene-2-carboxamide;
92) N-(3-chloro-5-((2,2,6,6-tetramethylpiperidin-4-yl)oxy)phenyl)-5-(2-(methylsulfonyl)propan-2-yl)benzo[b]thiophene-2-carboxamide;
93) tert-butyl (2-(3-(4-chlorophenoxy)-5-(5-(2-(methylsulfonyl)propan-2-yl)benzo[b]thiophene-2-carboxamido)phenoxy)ethyl)carbamate;
94) N-(3-(2-aminoethoxy)-5-(4-chlorophenoxy)phenyl)-5-(2-(methylsulfonyl)propan-2-yl)benzo[b]thiophene-2-carboxamide;
95) N-(5-chloro-2',4'-difluoro-[1,1'-biphenyl]-3-yl)-5-((methyl sulfonyl)methyl)benzo[b]thiophene-2-carboxamide;
96) (8-chloro-6-(4-chlorophenoxy)-2,3-dihydro-4H-benzo[b][1,4]oxazin-4-yl)(5-(2-(methylsulfonyl)propan-2-yl)benzo[b]thiophen-2-yl)methanone;
97) N-(3-chloro-5-(1-(4-chlorophenyl)cyclopropyl)phenyl)-5-(2-(methylsulfonyl)propan-2-yl)benzo[b]thiophene-2-carboxamide;
98) N-(3-chloro-5-((2,4-difluorophenyl)(methyl)amino)phenyl)-5-(2-(methylsulfonyl)propan-2-yl)benzo[b]thiophene-2-carboxamide;
99) N-(3-chloro-5-((4-chlorophenyl)(methyl)amino)phenyl)-5-(2-(methylsulfonyl)propan-2-yl)benzo[b]thiophene-2-carboxamide;
100) N-(2-chloro-6-((4-chlorophenyl)(methyl)amino)pyridin-4-yl)-5-(2-(methylsulfonyl)propan-2-yl)benzo[b]thiophene-2-carboxamide;
101) N-(2-chloro-6-((4-chlorocyclohex-3-en-1-yl)oxy)pyridin-4-yl)-5-(2-(methylsulfonyl)propan-2-yl)benzo[b]thiophene-2-carboxamide;
102) N-(2-chloro-6-((octahydroindolizin-7-yl)oxy)pyridin-4-yl)-5-(2-(methylsulfonyl)propan-2-yl)benzo[b]thiophene-2-carboxamide;
103) N-(3-chloro-5-(4-chlorophenoxy)phenyl)-5-(2-(methylsulfonyl)propan-2-yl)benzo[b]thiophene-2-carboximidamide 2,2,2-trifluoroacetate;
104) N-(2-chloro-6-(hexahydropyrrolo[1,2-a]pyrazin-2(1H)-yl)pyridin-4-yl)-5-(2-(methylsulfonyl)propan-2-yl)benzo[b]thiophene-2-carboxamide;
105) N-(2-(4-(tert-butyl)piperidin-1-yl)-6-chloropyridin-4-yl)-5-(2-(methylsulfonyl)propan-2-yl)benzo[b]thiophene-2-carboxamide;
106) N-(2-chloro-6-(octahydro-2H-pyrido[1,2-a]pyrazin-2-yl)pyridin-4-yl)-5-(2-(methylsulfonyl)propan-2-yl)benzo[b]thiophene-2-carboxamide;

107) N-(2-chloro-6-(7-ethyl-2,7-diazaspiro[4.4]nonan-2-yl)pyridin-4-yl)-5-(2-(methylsulfonyl)propan-2-yl)benzo[b]thiophene-2-carboxamide;
108) N-(2-chloro-6-(octahydroisoquinolin-2(1H)-yl)pyridin-4-yl)-5-(2-(methylsulfonyl)propan-2-yl)benzo[b]thiophene-2-carboxamide;
109) N-(2-chloro-6-((5-methylthiazol-2-yl)oxy)pyridin-4-yl)-5-(2-(methylsulfonyl)propan-2-yl)benzo[b]thiophene-2-carboxamide;
110) N-(2-chloro-6-((1-methyl-1H-pyrazol-5-yl)oxy)pyridin-4-yl)-5-(2-(methylsulfonyl)propan-2-yl)benzo[b]thiophene-2-carboxamide;
111) N-(2-chloro-6-((1,3,5-trimethyl-1H-pyrazol-4-yl)oxy)pyridin-4-yl)-5-(2-(methylsulfonyl)propan-2-yl)benzo[b]thiophene-2-carboxamide;
112) N-(2-chloro-6-((1-methyl-1H-pyrazol-4-yl)oxy)pyridin-4-yl)-5-(2-(methylsulfonyl)propan-2-yl)benzo[b]thiophene-2-carboxamide;
113) N-(2-chloro-6-((3,5-dimethylisoxazol-4-yl)oxy)pyridin-4-yl)-5-(2-(methylsulfonyl)propan-2-yl)benzo[b]thiophene-2-carboxamide;
114) N-(2-chloro-6-((5-methylthiophen-3-yl)oxy)pyridin-4-yl)-5-(2-(methylsulfonyl)propan-2-yl)benzo[b]thiophene-2-carboxamide;
115) N-(2-chloro-6-((2-methylthiophen-3-yl)oxy)pyridin-4-yl)-5-(2-(methylsulfonyl)propan-2-yl)benzo[b]thiophene-2-carboxamide;
116) N-(2-chloro-6-((4,5-dimethylisoxazol-3-yl)oxy)pyridin-4-yl)-5-(2-(methylsulfonyl)propan-2-yl)benzo[b]thiophene-2-carboxamide;
117) N-(2-chloro-6-((5-(trifluoromethyl)thiophen-3-yl)oxy)pyridin-4-yl)-5-(2-(methylsulfonyl)propan-2-yl)benzo[b]thiophene-2-carboxamide;
118) methyl 3-((6-chloro-4-(5-(2-(methylsulfonyl)propan-2-yl)benzo[b]thiophene-2-carboxamido)pyridin-2-yl)oxy)isoxazole-5-carboxylate;
119) N-(2-chloro-6-((4-methylthiazol-2-yl)oxy)pyridin-4-yl)-5-(2-(methylsulfonyl)propan-2-yl)benzo[b]thiophene-2-carboxamide;
120) N-(2-chloro-6-((5-methylthiophen-2-yl)oxy)pyridin-4-yl)-5-(2-(methylsulfonyl)propan-2-yl)benzo[b]thiophene-2-carboxamide; and
121) N-(2-chloro-6-((2-chlorothiophen-3-yl)oxy)pyridin-4-yl)-5-(2-(methylsulfonyl)propan-2-yl)benzo[b]thiophene-2-carboxamide.

The above-listed names of the compounds are described in accordance with the nomenclature method provided by ChemBioDraw Ultra software (Version 13.0.0.3015) of PerkinElmer.

The present invention provides a pharmaceutically acceptable salt of a heterocyclic derivative represented by formula (I) above. The pharmaceutically acceptable salt should have low toxicity to humans, and should not have any negative impact on the biological activities and physicochemical properties of parent compounds. Examples of the pharmaceutically acceptable salt may include an acid addition salt between a pharmaceutically usable free acid and a basic compound represented by formula (I), an alkaline metal salt (sodium salt, etc.) and an alkaline earth metal salt (potassium salt, etc.), an organic base addition salt between an organic base and carboxylic acid represented by formula (I), amino acid addition salt, etc.

Examples of a suitable form of salts according to the present invention may be a salt with an inorganic acid or organic acid, wherein the inorganic acid may be hydrochloric acid, sulfuric acid, nitric acid, phosphoric acid, perchloric acid, bromic acid, etc., and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc. The organic base which may be used for the preparation of the organic base addition salt may include tris(hydroxymethyl)methylamine, dicyclohexylamine, etc. Amino acids which may be used for the preparation of amino acid addition base may include natural amino acids such as alanine, and glycine.

The salts may be prepared using a conventional method. For example, the salts may be prepared by dissolving the compound represented by formula (I) in a water-miscible solvent such as methanol, ethanol, acetone, and 1,4-dioxane, adding a free acid or a free base, and then crystallizing the resultant thereafter.

Additionally, the compounds of the present invention may have a chiral carbon center, and thus they may be present in the form of an R or S isomer, a racemic compound, an individual enantiomer or a mixture, an individual diastereomer or a mixture, and all these stereoisomers and a mixture thereof may belong to the scope of the present invention.

Additionally, the compounds of the present invention may also include a hydrate or solvate of the heterocyclic derivative represented by formula (I). The hydrate or solvate may be prepared using a known method, and they are preferred to be non-toxic and water-soluble, and in particular, they are preferably water or a hydrate or solvate having 1-5 molecules of alcoholic solvent (especially ethanol, etc.) bound thereto.

The present invention also provides a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

Further, the present invention provides method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

Further, the present invention provides a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

Specifically, the diseases associated with the activation of STAT3 protein is selected from the group consisting of solid cancers, hematological or blood cancers, radio- or chemoresistant cancers, metastatic cancers, inflammatory diseases, immunological diseases, diabetes, macular degeneration, human papillomavirus infection and tuberculosis.

More specifically, the diseases associated with the activation of STAT3 protein are selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, autoimmune diseases comprising rheumatoid arthritis, psoriasis, hepatitis, inflammatory bowel disease, Crohn's disease, diabetes, macular degeneration, human papillomavirus infection, and tuberculosis.

In particular, a heterocyclic derivative represented by formula (I) above, or a pharmaceutically acceptable salt or a stereoisomer thereof has an excellent inhibitory effect on the activation of STAT3 protein, and thus the present invention also provides a composition for the inhibition of STAT3 protein comprising the same as an active ingredient.

The pharmaceutical composition of the present invention, in addition to the heterocyclic derivative represented by formula (I) above, the pharmaceutically acceptable salt thereof, or the stereoisomer thereof, may further include as active ingredients, common and non-toxic pharmaceutically acceptable additives, for example, a carrier, an excipient, a diluent, an adjuvant, etc., to be formulated into a preparation according to a conventional method.

The pharmaceutical composition of the present invention may be formulated into various forms of preparations for oral administration such as tablets, pills, powders, capsules, syrups, or emulsions, or for parenteral administration such as intramuscular, intravenous or subcutaneous injections, etc., and preferably in the form of a preparation for oral administration.

Examples of the additives to be used in the pharmaceutical composition of the present invention may include sweeteners, binders, solvents, solubilization aids, wetting agents, emulsifiers, isotonic agents, absorbents, disintegrating agents, antioxidants, preservatives, lubricants, fillers, flavoring agents, etc. For example, they may include, lactose, dextrose, sucrose, mannitol, sorbitol, cellulose, glycine, silica, talc, stearic acid, stearin, magnesium stearate, magnesium alluminosilicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc.

The pharmaceutical composition of the present invention may be formulated into a preparation for oral administration by adding additives to active ingredients, wherein the additives may include cellulose, calcium silicate, corn starch, lactose, sucrose, dextrose, calcium phosphate, stearic acid, magnesium stearate, calcium stearate, gelatin, talc, surfactants, suspension agents, emulsifiers, diluents, etc.

The pharmaceutical composition of the present invention may be formulated into a preparation for injection by adding additives to the active ingredients, for example, water, a saline solution, a glucose solution, an aqueous glucose solution analog, alcohol, glycol, ether, oil, fatty acid, fatty acid ester, glyceride, surfactants, suspension agents, emulsifiers, etc.

The compound of the present invention may be administered preferably in an amount ranging from 0.1 to 2,000 mg/day based on an adult subject with 70 kg body weight. The compound of the present invention may be administered once daily or a few divided doses. The dosage of the compound of the present invention may vary depending on the health conditions, age, body weight, sex of the subject, administration route, severity of illness, etc., and the scope of the present invention will not be limited to the dose suggested above.

EXAMPLE

Hereinafter, the present invention is described more specifically by the following examples, but these are provided only for illustration purposes and the present invention is not limited thereto.

The definition of the abbreviations used in the following examples is as follows.

TABLE 1

| Abbreviation | Full name |
|---|---|
| $AlCl_3$ | Aluminum chloride |
| AcOH | Acetic acid |
| AIBN | 2,2'-Azobis(2-methylpropionitrile) |
| BINAP | 2,2'-Bis(diphenylphosphino)-1,1'-binaphthyl |
| $BBr_3$ | Boron tribromide |
| Brine | Brine is water saturated or nearly saturated with a brine salt (generally, sodium chloride) |
| n-BuLi | n-butyllithium |
| tert-BuLi | tert-butyllithium |
| tert-BuOH | tert-buthyl alcohol |
| $CH_3CN$ | Acetonitrile |
| $CHCl_3$ | Chloroform |
| $CHBr_3$ | Bromoform |
| $CDCl_3$ | Deuterated chloroform |
| $CH_2Cl_2$ | Dichloromethane |
| $CH_3I$ | Methyl iodide |
| $(COCl)_2$ | Oxalyl chloride |
| $Cs_2CO_3$ | Cesium carbonate |
| CuI | Copper (I) iodide |
| $Cu_2O$ | Copper (I) oxide |
| DBU | 1,8-Diazabicyclo[5.4.0]undec-7-ene |
| DEAD | Diethyl azodicarboxylate |
| DIPEA | N,N-diisopropylethylamine |
| DME | 1,2-Dimethoxyethane |
| DMF | N,N-dimethylformamide |
| DMSO | Dimethylsulfoxide |
| DMSO-$d_6$ | Dimethylsulfoxide-$d_6$ |
| EtOAc | Ethyl acetate |
| EtOH | Ethyl alcohol |
| $Et_2O$ | Diethyl ether |
| HATU | 2-(7-Aza-1H-benzotriazole-1-yl)-1,1,3,3-tetramethyluronium hexafluorophosphate |
| HBr | Hydrogen bromide |
| HCl | Hydrogen chloride |
| n-Hex | n-Hexane |
| $H_2O$ | Water |
| $H_2O_2$ | Hydrogen peroxide |
| $K_2CO_3$ | Potassium carbonate |
| KOH | Potassium hydroxide |
| $LiAlH_4$ | Lithium aluminum hydride |
| $LiOHH_2O$ | Lithium hydroxide, monohydrate |
| MeOH | Methyl alcohol |
| $Na_2CO_3$ | Sodium carbonate |
| $Na_2SO_4$ | Sodium sulfate |
| NaH | Sodium hydride |
| $NaHCO_3$ | Sodium bicarbonate |
| $NaHSO_4$ | Sodium bisulfate |
| $NaH_2PO_4$ | Sodium phosphate monobasic acid |
| $NaIO_4$ | Sodium periodate |
| $NaN_3$ | Sodium azide |
| NaOH | Sodium hydroxide |
| NaOMe | Sodium methoxide |
| NaOt-Bu | Sodium tert-butoxide |
| $NH_4Cl$ | Ammonium chloride |
| $Pd(dba)_2$ | Bis(dibenzylideneacetone)palladium(0) |
| $Pd(PPh_3)_4$ | Tetrakis(triphenylphosphine)palladium(0) |
| $Pd(OAc)_2$ | Palladium(II) acetate |
| $PCl_3$ | Phosphorus trichloride |
| $PCl_5$ | Phosphorus pentachloride |
| $PPh_3$ | Triphenylphosphine |
| $RuCl_3H_2O$ | Ruthenium(III) chloride hydrate |
| $SOCl_2$ | Thionyl chloride |
| $Tf_2O$ | Trifluoromethanesulfonic anhydride |
| THF | Tetrahydrofuran |
| $TiCl_4$ | Titanium tetrachloride |
| TFA | Trifluoroacetic acid |
| XPhos | 4,5-bis(diphenylphosphino)-9,9-dimethylxanthene |
| Zn | Zinc |
| $ZnBr_2$ | Zinc bromide |
| $ZnCl_2$ | Zinc chloride |

Intermediate 1) Synthesis of 6-fluoro-5-(2-(methylsulfonyl)propan-2-yl)benzo[b]thiophene-2-carboxylic acid (a) Synthesis of 1-(bromomethyl)-2,4-difluoro-5-methylbenzene Paraformaldehyde (247.0 mg, 7.81 mmol) was dissolved in 33% solution of HBr in AcOH (4.0 mL), and 2,4-difluoro-1-methylbenzene (1.0 g, 7.81 mmol) and $ZnBr_2$ (880.0 mg, 3.91 mmol) were added. The reaction mixture was stirred at 120° C. for 4 hours, cooled to room temperature, sat. $NaHCO_3$ was added, and extracted with EtOAc. The organic extract was washed with brine, dried over anhydrous $Na_2SO_4$, and concentrated under reduced pressure. The residue was purified by flash column chromatography (silica gel, n-Hex:EtOAc=9:1) to obtain 1-(bromomethyl)-2,4-difluoro-5-methylbenzene (1.1 g, 64%) as a colorless liquid.
$^1$H-NMR (400 MHz, $CDCl_3$): δ 7.20 (t, 1H, J=8.4 Hz), 6.77 (t, 1H, J=9.5 Hz), 4.46 (s, 2H), 2.24 (s, 3H)

(b) Synthesis of 1,5-difluoro-2-methyl-4-((methylsulfonyl)methyl)benzene 1-(Bromomethyl)-2,4-difluoro-5-methylbenzene (260.0 mg, 1.18 mmol) was dissolved in anhydrous EtOH (6.0 mL) and sodium methanesulfinate (120.0 mg, 1.18 mmol) was added. The reaction mixture was refluxed for 2 hours, cooled to room temperature, and concentrated under reduced pressure. The residue was recrystallized with $Et_2O$ to obtain 1,5-difluoro-2-methyl-4-((methylsulfonyl)methyl)benzene (160.0 mg, 61%) as a white solid.
$^1$H-NMR (400 MHz, $CDCl_3$): δ 7.32 (t, 1H, J=8.3 Hz), 6.86 (t, 1H, J=9.5 Hz), 4.24 (s, 2H), 2.82 (s, 3H), 2.27 (s, 3H)

(c) Synthesis of 1,5-difluoro-2-methyl-4-(2-(methylsulfonyl)propan-2-yl)benzene 1,5-Difluoro-2-methyl-4-((methylsulfonyl)methyl)benzene (3.4 g, 15.40 mmol) was dissolved in anhydrous DMF (22.4 mL), and NaOt-Bu (3.7 g, 38.60 mmol) and $CH_3I$ (4.8 mL, 77.20 mmol) were added at 0° C. The reaction mixture was stirred at 0° C., $H_2O$ was added, and extracted with EtOAc. The organic extract was washed with brine, dried over anhydrous $Na_2SO_4$ and concentrated under reduced pressure. The residue was purified by flash column chromatography (silica gel, n-Hex:EtOAc=4:1) to obtain 1,5-difluoro-2-methyl-4-(2-(methylsulfonyl)propan-2-yl)benzene (370.0 mg, 10%) as a white solid.
$^1$H-NMR (400 MHz, $CDCl_3$): δ 7.38 (t, 1H, J=9.2 Hz), 6.75 (t, 1H, J=9.2 Hz), 2.70-2.81 (m, 3H), 1.90 (s, 3H), 1.74 (d, 6H, J=7.2 Hz)

(d) Synthesis of 1-(bromomethyl)-2,4-difluoro-5-(2-(methylsulfonyl)propan-2-yl)benzene 1,5-Difluoro-2-methyl-4-(2-(methylsulfonyl)propan-2-yl)benzene (370.0 mg, 1.49 mmol) was dissolved in anhydrous 1,2-dichloroethane (15.0 mL), and N-bromosuccinimide (265.0 mg, 1.49 mmol) and AIBN (25.0 mg, 0.15 mmol) were added. The reaction mixture was refluxed at 100° C. for 15 hours, cooled to room temperature, $H_2O$ was added, and extracted with $CH_2Cl_2$. The organic extract was washed with brine, dried over anhydrous $Na_2SO_4$ and concentrated under reduced pressure. The residue was purified by silica column chromatography (n-Hex:EtOAc=4:1) to obtain 1-(bromomethyl)-2,4-difluoro-5-(2-(methylsulfonyl)propan-2-yl)benzene (367.0 mg, 66%) as a white solid.
$^1$H-NMR (400 MHz, $CDCl_3$): δ 7.60 (t, 1H, J=8.5 Hz), 6.88 (dd, 1H, J=12.4, 9.2 Hz), 4.28 (s, 2H), 2.74 (s, 3H), 1.93 (d, 6H, J=2.6 Hz)

(e) Synthesis of 2,4-difluoro-5-(2-(methylsulfonyl)propan-2-yl)benzaldehyde 1-(Bromomethyl)-2,4-difluoro-5-(2-(methylsulfonyl)propan-2-yl)benzene (367.0 mg, 1.12 mmol) was dissolved in anhydrous $CH_3CN$ (11.0 mL), and 4-methylmorpholine N-oxide (263.0 mg, 2.24 mmol) and molecular sieves (1.0 g) were added. The reaction mixture was stirred at room temperature for 90 minutes, $H_2O$ was added, and extracted with EtOAc. The organic extract was washed with brine, dried over anhydrous $Na_2SO_4$ and concentrated under reduced pressure. The residue was recrystallized with $CH_2Cl_2$ and n-Hex to obtain 2,4-difluoro-5-(2-(methylsulfonyl)propan-2-yl)benzaldehyde (200.0 mg, 66%) as a white solid.
$^1$H-NMR (400 MHz, $CDCl_3$): δ 10.16 (s, 1H), 8.07 (t, 1H, J=8.6 Hz), 7.56 (dd, 1H, J=12.6, 10.6 Hz), 2.90 (s, 3H), 1.87 (d, 6H, J=2.5 Hz)

(f) Synthesis of methyl 6-fluoro-5-(2-(methylsulfonyl)propan-2-yl)benzo[b]thiophene-2-carboxylate 2,4-Difluoro-5-(2-(methylsulfonyl)propan-2-yl)benzaldehyde (170.0 mg, 0.65 mmol) was dissolved in anhydrous DMF (11.0 mL), and methyl 2-mercaptoacetate (58.0 μL, 0.65 mmol) and $K_2CO_3$ (179.6 mg, 1.30 mmol) were added. The reaction mixture was stirred at 80° C. for 5 hours, cooled to room temperature, $H_2O$ was added, and extracted with EtOAc. The organic extract was washed with brine, dried over anhydrous $Na_2SO_4$ and concentrated under reduced pressure. The residue was purified by flash column chromatography (silica gel, n-Hex:EtOAc=1:1) to obtain methyl 6-fluoro-5-(2-(methylsulfonyl)propan-2-yl)benzo[b]thiophene-2-carboxylate (165.0 mg, 77%) as a white solid.
$^1$H-NMR (400 MHz, $CDCl_3$): δ 8.08 (d, 1H, J=7.6 Hz), 8.03 (s, 1H), 7.60 (d, 1H, J=12.8 Hz), 3.96 (s, 3H), 2.77 (s, 3H), 2.00 (d, 6H, J=2.6 Hz)

(g) Synthesis of 6-fluoro-5-(2-(methylsulfonyl)propan-2-yl)benzo[b]thiophene-2-carboxylic acid Methyl 6-fluoro-5-(2-(methylsulfonyl)propan-2-yl)benzo[b]thiophene-2-carboxylate (165.0 mg, 0.50 mmol) was dissolved in THF (3.4 mL) and $H_2O$ (1.6 mL), and $LiOH.H_2O$ (210.0 mg, 4.99 mmol) was added. The reaction mixture was stirred at room temperature for 1 hour, $H_2O$ was added, and extracted with EtOAc. The organic extract was washed with brine, dried over anhydrous $Na_2SO_4$ and concentrated under reduced pressure. The residue was recrystallized with $CH_2Cl_2$ and n-Hex to obtain 6-fluoro-5-(2-(methylsulfonyl)propan-2-yl)benzo[b]thiophene-2-carboxylic acid (150.0 mg, quant) as a white solid.
LC/MS ESI (−): 315 (M−1)

Intermediate 2) Synthesis of 5-((methylsulfonyl)methyl)benzo[b]thiophene-2-carboxylic acid (a) Synthesis of methyl 5-methylbenzo[b]thiophene-2-carboxylate The synthesis procedure of Intermediate 1-f was repeated except for using 2-fluoro-5-methylbenzaldehyde (300.0 mg, 2.17 mmol) as a starting material to obtain methyl 5-methylbenzo[b]thiophene-2-carboxylate (164.0 mg, 37%).
LC/MS (ESI+): 207 (M+1)
$^1$H-NMR (400 MHz, CDCl$_3$): δ 7.99 (s, 1H), 7.29 (d, 1H, J=8.4 Hz), 7.67 (s, 1H), 7.30 (dd, 1H, J=8.3, 1.3 Hz), 3.94 (s, 3H), 2.48 (s, 3H)

(b) Synthesis of methyl 5-(bromomethyl)benzo[b]thiophene-2-carboxylate

The synthesis procedure of Intermediate 1-d was repeated except for using methyl 5-methylbenzo[b]thiophene-2-carboxylate (100.0 mg, 0.49 mmol) as a starting material to obtain methyl 5-(bromomethyl)benzo[b]thiophene-2-carboxylate (46.5 mg, 34%).
$^1$H-NMR (400 MHz, CDCl$_3$): δ 8.04 (s, 1H), 7.89 (s, 1H), 7.85 (d, 1H, J=8.4 Hz), 7.50 (d, 1H, J=8.5 Hz), 4.63 (s, 2H), 3.95 (s, 3H)

(c) Synthesis of methyl 5-((methylsulfonyl)methyl)benzo[b]thiophene-2-carboxylate The synthesis procedure of Intermediate 1-b was repeated except for using methyl 5-(bromomethyl)benzo[b]thiophene-2-carboxylate (45.0 mg, 0.16 mmol) as a starting material to obtain methyl 5-((methylsulfonyl)methyl)benzo[b]thiophene-2-carboxylate (45.0 mg, quant).
LC/MS (ESI+): 285 (M+1)
$^1$H-NMR (400 MHz, CDCl$_3$): δ 8.07 (s, 1H), 7.91-7.93 (m, 2H), 7.51 (d, 1H, J=8.4 Hz), 4.37 (s, 2H), 3.96 (s, 3H), 2.80 (s, 3H)

(d) Synthesis of 5-((methylsulfonyl)methyl)benzo[b]thiophene-2-carboxylic acid

The synthesis procedure of Intermediate 1-g was repeated except for using methyl 5-((methylsulfonyl)methyl)benzo[b]thiophene-2-carboxylate (45.0 mg, 0.16 mmol) as a starting material to obtain 5-((methylsulfonyl)methyl)benzo[b]thiophene-2-carboxylic acid (39.3 mg, 90%).
$^1$H-NMR (400 MHz, DMSO-d$_6$): δ 13.50 (brs, 1H), 8.15 (s, 1H), 8.08 (d, 1H, J=8.5 Hz), 8.03 (s, 1H), 7.53 (d, 1H, J=8.5 Hz), 4.62 (s, 2H), 2.94 (s, 3H)

Intermediate 3) Synthesis of 5-(((trifluoromethyl)sulfonyl)methyl)benzo[b]thiophene-2-carboxylic acid (a) Synthesis of methyl 5-(((trifluoromethyl)sulfonyl)methyl)benzo[b]thiophene-2-carboxylate Methyl 5-(bromomethyl)benzo[b]thiophene-2-carboxylate (263.0 mg, 0.92 mmol) and sodium triflinate (216.0 mg, 1.38 mmol) were dissolved in propionitrile (4.6 mL). The reaction mixture was refluxed for 16 hours and concentrated under reduced pressure. The residue was purified by flash column chromatography (silica gel, n-Hex:EtOAc=4:1) to obtain methyl 5-(((trifluoromethyl)sulfonyl)methyl)benzo[b]thiophene-2-carboxylate (171.8 mg, 55%) as a white solid.
LC/MS (ESI+): 339 (M+1)
$^1$H-NMR (400 MHz, CDCl$_3$): δ 8.08 (s, 1H), 7.94-7.96 (m, 2H), 7.49 (dd, 1H, J=8.5, 1.6 Hz), 4.61 (s, 2H), 3.97 (s, 3H)

(b) Synthesis of 5-(((trifluoromethyl)sulfonyl)methyl)benzo[b]thiophene-2-carboxylic acid The synthesis procedure of Intermediate 1-g was repeated except for using methyl 5-(((trifluoromethyl)sulfonyl)methyl)benzo[b]thiophene-2-carboxylate (210.0 mg, 0.62 mmol) as a starting material to obtain 5-(((trifluoromethyl)sulfonyl)methyl)benzo[b]thiophene-2-carboxylic acid (151.8 mg) without purification.
$^1$H-NMR (400 MHz, DMSO-d$_6$): δ 13.62 (brs, 1H), 8.20 (s, 1H), 8.15 (d, 1H, J=8.5 Hz), 8.12 (s, 1H), 7.58 (dd, 1H, J=8.5, 1.6 Hz), 5.41 (s, 2H)

Intermediate 4) Synthesis of 5-(fluoro(methylsulfonyl)methyl)benzo[b]thiophene-2-carboxylic acid (a) Synthesis of 2-methyl-4-((methylsulfonyl)methyl)-1-nitrobenzene The synthesis procedure of Intermediate 1-b was repeated except for using 4-(bromomethyl)-2-methyl-1-nitrobenzene (2.0 g, 8.69 mmol) as a starting material to obtain 2-methyl-4-((methylsulfonyl)methyl)-1-nitrobenzene (1.7 g, 86%).
$^1$H-NMR (400 MHz, CDCl$_3$): δ 8.02 (d, 1H, J=8.1 Hz), 7.40-7.42 (m, 2H), 4.29 (s, 2H), 2.86 (s, 3H), 2.64 (s, 3H)

(b) Synthesis of 4-(fluoro(methylsulfonyl)methyl)-2-methyl-1-nitrobenzene

2-Methyl-4-((methylsulfonyl)methyl)-1-nitrobenzene (760.0 mg, 3.32 mmol) and N-fluoro-N-(phenylsulfonyl)benzene sulfonamide (2.1 g, 6.64 mmol) were dissolved in anhydrous THF (16.6 mL), and 1.6M solution of n-BuLi in n-Hex (4.2 mL, 6.64 mmol) was slowly added dropwise at −78° C. The reaction mixture was stirred for 9 hours, H$_2$O was added at room temperature, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=1:1) to obtain 4-(fluoro(methylsulfonyl)methyl)-2-methyl-1-nitrobenzene (175.0 mg, 21%) as a brown solid.
$^1$H-NMR (400 MHz, CDCl$_3$): δ 8.05 (d, 1H, J=8.9 Hz), 7.94 (m, 1H), 7.54 (m, 1H), 6.09 (d, 1H, J=46.8 Hz), 3.04 (d, 3H, J=1.6 Hz), 2.65 (s, 3H)

(c) Synthesis of 2-(bromomethyl)-4-(fluoro(methylsulfonyl)methyl)-1-nitrobenzene The synthesis procedure of Intermediate 1-d was repeated except for using 4-(fluoro(methylsulfonyl)methyl)-2-methyl-1-nitrobenzene (168.0 mg, 0.68 mmol) as a starting material to obtain 2-(bromomethyl)-4-(fluoro(methylsulfonyl)methyl)-1-nitrobenzene (129.5 mg).
$^1$H-NMR (400 MHz, CDCl$_3$): δ 8.05 (d, 1H, J=8.9 Hz), 7.95 (m, 1H), 7.93 (m, 1H), 6.10 (d, 1H, J=46.8 Hz), 4.84 (s, 2H), 2.65 (s, 3H)

(d) Synthesis of 5-(fluoro(methylsulfonyl)methyl)-2-nitrobenzaldehyde

The synthesis procedure of Intermediate 1-e was repeated except for using 2-(bromomethyl)-4-(fluoro(methylsulfonyl)methyl)-1-nitrobenzene (127.0 mg) as a starting material to obtain 5-(fluoro(methylsulfonyl)methyl)-2-nitrobenzaldehyde (13.5 mg, 2 steps yield: 8%).
$^1$H-NMR (400 MHz, CDCl$_3$): δ 10.44 (s, 1H), 8.23 (d, 1H, J=8.5 Hz), 8.13 (d, 1H, J=1.9 Hz), 7.97 (dd, 1H, J=8.5, 2.0 Hz), 6.21 (d, 1H, J=47.0 Hz), 3.10 (d, 3H, J=1.7 Hz)

(e) Synthesis of methyl 5-(fluoro(methylsulfonyl)methyl)benzo[b]thiophene-2-carboxylate The synthesis procedure of Intermediate 1-f was repeated except for using 5-(fluoro(methylsulfonyl)methyl)-2-nitrobenzaldehyde (10.0 mg, 0.04 mmol) as a starting material to obtain methyl 5-(fluoro(methylsulfonyl)methyl)benzo[b]thiophene-2-carboxylate (11.0 mg, quant).

LC/MS (ESI+): 303 (M+1)

$^1$H-NMR (400 MHz, CDCl$_3$): δ 8.11 (s, 1H), 8.08 (s, 1H), 7.98 (d, 1H, J=8.6 Hz), 7.63 (dd, 1H, J=8.5, 1.6 Hz), 6.17 (d, 1H, J=46.2 Hz), 3.97 (s, 3H), 3.02 (d, 3H, J=1.4 Hz)

(f) Synthesis of 5-(fluoro(methylsulfonyl)methyl) benzo[b]thiophene-2-carboxylic acid The synthesis procedure of Intermediate 1-g was repeated except for using methyl 5-(fluoro(methylsulfonyl)methyl)benzo[b]thiophene-2-carboxylate (11.0 mg, 0.04 mmol) as a starting material to obtain 5-(fluoro(methylsulfonyl)methyl)benzo[b]thiophene-2-carboxylic acid (6.7 mg, 64%).

$^1$H-NMR (400 MHz, DMSO-d$_6$): δ 8.23 (s, 1H), 8.17-8.20 (m, 2H), 7.59 (dd, 1H, J=8.5, 1.6 Hz), 6.93 (d, 1H, J=45.2 Hz), 3.19 (d, 3H, J=1.2 Hz)

Intermediate 5) Synthesis of 5-(2-(methylsulfonyl)propan-2-yl)benzo[b]thiophene-2-carboxylic acid (a) Synthesis of 2-methyl-4-(2-(methylsulfonyl)propan-2-yl)-1-nitrobenzene The synthesis procedure of Intermediate 1-c was repeated except for using 2-methyl-4-((methylsulfonyl)methyl)-1-nitrobenzene (500.0 mg, 2.18 mmol) as a starting material to obtain 2-methyl-4-(2-(methylsulfonyl)propan-2-yl)-1-nitrobenzene (308.0 mg, 55%).

$^1$H-NMR (400 MHz, CDCl$_3$): δ 8.00 (d, 1H, J=9.2 Hz), 7.62-7.63 (m, 2H), 2.65 (s, 3H), 2.61 (s, 3H), 1.88 (s, 6H)

(b) Synthesis of 2-(bromomethyl)-4-(2-(methylsulfonyl)propan-2-yl)-1-nitrobenzene The synthesis procedure of Intermediate 1-d was repeated except for using 2-methyl-4-(2-(methylsulfonyl)propan-2-yl)-1-nitrobenzene (270.0 mg, 1.05 mmol) as a starting material to obtain 2-(bromomethyl)-4-(2-(methylsulfonyl)propan-2-yl)-1-nitrobenzene (272.0 mg).

$^1$H-NMR (400 MHz, CDCl$_3$): δ 8.07 (d, 1H, J=8.7 Hz), 7.84 (d, 1H, J=2.2 Hz), 7.77 (dd, 1H, J=8.7, 2.2 Hz), 4.86 (s, 2H), 2.63 (s, 3H), 1.91 (s, 6H)

(c) Synthesis of 5-(2-(methylsulfonyl)propan-2-yl)-2-nitrobenzaldehyde

The synthesis procedure of Intermediate 1-e was repeated except for using 2-(bromomethyl)-4-(2-(methylsulfonyl)propan-2-yl)-1-nitrobenzene (270.0 mg) as a starting material to obtain 5-(2-(methylsulfonyl)propan-2-yl)-2-nitrobenzaldehyde (139.0 mg, 2 step yield: 49%).

LC/MS (ESI+): 272 (M+1)

$^1$H-NMR (400 MHz, CDCl$_3$): δ 10.46 (s, 1H), 8.10-8.18 (m, 3H), 2.66 (s, 3H), 1.93 (s, 6H)

(d) Synthesis of methyl 5-(2-(methylsulfonyl)propan-2-yl)benzo[b]thiophene-2-carboxylate The synthesis procedure of Intermediate 1-f was repeated except for using 5-(2-(methylsulfonyl)propan-2-yl)-2-nitrobenzaldehyde (137.0 mg, 0.51 mmol) as a starting material to obtain methyl 5-(2-(methylsulfonyl)propan-2-yl)benzo[b]thiophene-2-carboxylate (140.0 mg, 89%).

$^1$H-NMR (400 MHz, CDCl$_3$): δ 8.12 (d, 1H, J=1.8 Hz), 8.08 (s, 1H), 7.90 (d, 1H, J=8.7 Hz), 7.79 (dd, 1H, J=8.7, 1.9 Hz), 3.96 (s, 3H), 2.55 (s, 3H), 1.93 (s, 6H)

(e) Synthesis of 5-(2-(methylsulfonyl)propan-2-yl)benzo[b]thiophene-2-carboxylic acid The synthesis procedure of Intermediate 1-g was repeated except for using methyl 5-(2-(methylsulfonyl)propan-2-yl)benzo[b]thiophene-2-carboxylate (155.0 mg, 0.50 mmol) as a starting material to obtain 5-(2-(methylsulfonyl)propan-2-yl)benzo[b]thiophene-2-carboxylic acid (115.0 mg, 78%).

$^1$H-NMR (400 MHz, DMSO-d$_6$): δ 13.55 (brs, 1H), 8.25 (s, 1H), 8.14 (s, 1H), 8.07 (d, 1H, J=8.7 Hz), 7.76 (dd, 1H, J=8.8, 1.7 Hz), 2.73 (s, 3H), 1.83 (s, 6H)

Intermediate 6) Synthesis of 5-(1-(methylsulfonyl)cyclopropyl)benzo[b]thiophene-2-carboxylic acid (a) Synthesis of 2-methyl-4-(1-(methylsulfonyl)cyclopropyl)-1-nitrobenzene 2-Methyl-4-((methylsulfonyl)methyl)-1-nitrobenzene (500.0 mg, 2.18 mmol), 1,2-dibromoethane (0.3 mL, 3.27 mmol) and tetra-n-butylammonium bromide (70.3 mg, 0.22 mmol) were dissolved in toluene (22.0 mL), and 10N NaOH aqueous solution (0.7 mL, 6.54 mmol) was slowly added. The reaction mixture was heated at 40° C. for 16 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex: EtOAc=4:1) to obtain 2-methyl-4-(1-(methylsulfonyl)cyclopropyl)-1-nitrobenzene (92.0 mg, 17%) as a yellow oil.

$^1$H-NMR (400 MHz, CDCl$_3$): δ 8.00 (d, 1H, J=8.4 Hz), 7.58 (m, 1H), 7.53 (m, 1H), 2.79 (s, 3H), 2.62 (s, 3H), 1.89-1.92 (m, 2H), 1.30-1.33 (m, 2H)

(b) Synthesis of 2-(bromomethyl)-4-(1-(methylsulfonyl)cyclopropyl)-1-nitrobenzene The synthesis procedure of Intermediate 1-d was repeated except for using 2-methyl-4-(1-(methylsulfonyl)cyclopropyl)-1-nitrobenzene (95.0 mg, 0.37 mmol) as a starting material to obtain 2-(bromomethyl)-4-(1-(methylsulfonyl)cyclopropyl)-1-nitrobenzene (102.0 mg).

$^1$H-NMR (400 MHz, CDCl$_3$): δ 8.05 (d, 1H, J=8.4 Hz), 7.79 (d, 1H, J=2.0 Hz), 7.69 (dd, 1H, J=8.4, 2.0 Hz), 4.83 (s, 2H), 2.80 (s, 3H), 1.90-1.95 (m, 2H), 1.34-1.37 (m, 2H)

(c) Synthesis of 5-(1-(methylsulfonyl)cyclopropyl)-2-nitrobenzaldehyde

The synthesis procedure of Intermediate 1-e was repeated except for using 2-(bromomethyl)-4-(1-(methylsulfonyl)cyclopropyl)-1-nitrobenzene (100.0 mg) as a starting material to obtain 5-(1-(methylsulfonyl)cyclopropyl)-2-nitrobenzaldehyde (40.6 mg, 2 steps yield: 41%).

LC/MS (ESI+): 270 (M+1)

$^1$H-NMR (400 MHz, CDCl$_3$): δ 10.43 (s, 1H), 8.16 (d, 1H, J=8.2 Hz), 8.03-8.07 (m, 2H), 2.80 (s, 3H), 1.96-1.99 (m, 2H), 1.35-1.39 (m, 2H)

(d) Synthesis of methyl 5-(1-(methylsulfonyl)cyclopropyl)benzo[b]thiophene-2-carboxylate The synthesis procedure of Intermediate 1-f was repeated except for using 5-(1-(methylsulfonyl)cyclopropyl)-2-nitrobenzaldehyde (40.0 mg, 0.15 mmol) as a starting material to obtain methyl 5-(1-(methylsulfonyl)cyclopropyl)benzo[b]thiophene-2-carboxylate (35.9 mg, 78%).

LC/MS (ESI+): 311 (M+1)

$^1$H-NMR (400 MHz, CDCl$_3$): δ 8.04-8.07 (m, 2H), 7.88 (m, 1H), 7.67 (m, 1H), 3.96 (s, 3H), 2.77 (s, 3H), 1.90-1.91 (m, 2H), 1.34-1.36 (m, 2H)

(e) Synthesis of 5-(1-(methylsulfonyl)cyclopropyl)benzo[b]thiophene-2-carboxylic acid The synthesis procedure of Intermediate 1-g was repeated except for using methyl 5-(1-(methylsulfonyl)cyclopropyl)benzo[b]thiophene-2-carboxylate (33.0 mg, 0.11 mmol) as a starting material to obtain 5-(1-(methylsulfonyl)cyclopropyl)benzo[b]thiophene-2-carboxylic acid (21.9 mg, 70%).

LC/MS ESI (+): 297 (M+1)

$^1$H-NMR (400 MHz, DMSO-d$_6$): δ 13.57 (brs, 1H), 8.19 (s, 1H), 8.10 (s, 1H), 8.07 (d, 1H, J=8.5 Hz), 7.67 (d, 1H, J=8.9 Hz), 2.88 (s, 3H), 1.67-1.70 (m, 2H), 1.35-1.38 (m, 2H)

Intermediate 7) Synthesis of 6-chloro-5-(2-(methylsulfonyl)propan-2-yl)benzo[b]thiophene-2-carboxylic acid (a) Synthesis of 1-(2-chloro-4-fluoro-5-methylphenyl)ethan-1-one AlCl$_3$ (5.8 g, 43.3 mmol) was dissolved in 1,2-dichloroethane (34.6 mL), and acetyl chloride (3.1 mL, 43.3 mmol) was added dropwise at 0° C. 4-Chloro-2-fluoro-1-methylbenzene (5.0 g, 34.6 mmol) was added. The reaction mixture was stirred at 0° C. for 1 hour and then at 60° C. for 16 hours. 1N HCl aqueous solution was added dropwise, and the reaction mixture was extracted with EtOAc. The organic extract was washed with sat. NaHCO$_3$ aqueous solution and brine, dried over anhydrous Na$_2$SO$_4$ and concentrated under reduced pressure. The residue was purified by flash column chromatography (silica gel, n-Hex:EtOAc=9:1) to obtain 1-(2-chloro-4-fluoro-5-methylphenyl)ethan-1-one (4.9 g, 75%) as a yellow oil.

LC/MS ESI (+): 187 (M+1)

$^1$H-NMR (400 MHz, CDCl$_3$): δ 7.48 (d, 1H, J=8.1 Hz), 7.10 (d, 1H, J=9.1 Hz), 2.64 (s, 3H), 2.27 (s, 3H)

(b) Synthesis of 2-(2-chloro-4-fluoro-5-methylphenyl)propan-2-ol 1-(2-Chloro-4-fluoro-5-methylphenyl)ethan-1-one (4.9 g, 26.00 mmol) was dissolved in THF (260.0 mL), and 3.0M solution of methylmagnesium bromide in Et$_2$O (26.0 mL) was added dropwise at −8° C. The reaction mixture was stirred for 16 hours, 1N HCl aqueous solution was added dropwise at 0° C. to quench the reaction, and extracted with EtOAc. The organic extract was washed with brine, dried over anhydrous Na$_2$SO$_4$ and concentrated under reduced pressure. The residue was purified by flash column chromatography (amine silica gel, n-Hex:EtOAc=2:1) to obtain 2-(2-chloro-4-fluoro-5-methylphenyl)propan-2-ol (4.3 g, 82%) as a colorless oil.

$^1$H-NMR (400 MHz, CDCl$_3$): δ 7.50 (d, 1H, J=8.4 Hz), 7.04 (d, 1H, J=9.1 Hz), 2.44 (s, 1H), 2.25 (d, 3H, J=1.7 Hz), 1.70 (s, 6H)

(c) Synthesis of 2-(2-chloro-4-fluoro-5-methylphenyl)propane-2-thiol 2-(2-Chloro-4-fluoro-5-methylphenyl)propan-2-ol (4.3 g, 21.40 mmol) and Lawesson's reagent (5.2 g, 12.80 mmol) were dissolved in toluene (107.0 mL), and H$_2$O (0.5 mL) was added. The reaction mixture was stirred at 50° C. for 16 hours, H$_2$O was added, and extracted with EtOAc. The organic extract was washed with sat. NaHCO$_3$ aqueous solution, dried over anhydrous Na$_2$SO$_4$ and concentrated under reduced pressure. The residue was purified by flash column chromatography (silica gel, n-Hex:DCM=4:1) to obtain 2-(2-chloro-4-fluoro-5-methylphenyl)propane-2-thiol (2.7 g, 59%) as a pale yellow oil.

$^1$H-NMR (400 MHz, CDCl$_3$): δ 7.31 (d, 1H, J=8.1 Hz), 7.08 (d, 1H, J=9.1 Hz), 2.89 (s, 1H), 2.24 (s, 3H), 1.92 (s, 6H)

(d) Synthesis of (2-(2-chloro-4-fluoro-5-methylphenyl)propan-2-yl)(methyl)sulfane NaOH (357.0 mg, 8.92 mmol) was dissolved in EtOH (34.3 mL), and dimethyl sulfate (1.0 mL, 10.29 mmol) was added dropwise. 2-(2-Chloro-4-fluoro-5-methylphenyl)propane-2-thiol (1.5 g, 6.86 mmol) was added, and the reaction mixture was stirred at room temperature for 2 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:DCM=6:1) to obtain (2-(2-chloro-4-fluoro-5-methylphenyl)propan-2-yl)(methyl)sulfane (1.5 g, 93%) as a colorless oil.

$^1$H-NMR (400 MHz, CDCl$_3$): δ 7.27 (d, 1H, J=7.7 Hz), 7.08 (d, 1H, J=9.2 Hz), 2.25 (d, 3H, J=1.7 Hz), 1.81-1.83 (m, 9H)

(e) Synthesis of 1-chloro-5-fluoro-4-methyl-2-(2-(methylsulfonyl)propan-2-yl)benzene (2-(2-Chloro-4-fluoro-5-methylphenyl)propan-2-yl)(methyl)sulfane (1.5 g, 6.36 mmol) was dissolved in AcOH (31.8 mL) and 35 wt % H$_2$O$_2$ aqueous solution (6.4 mL) was added dropwise. The reaction mixture was stirred at room temperature for 16 hours, H$_2$O was added, and extracted with EtOAc. The organic extract was washed with sat. NaHCO$_3$ aqueous solution and brine, dried over anhydrous Na$_2$SO and concentrated under reduced pressure. The residue was purified by flash column chromatography (amine silica gel, n-Hex:EtOAc=4:1) to obtain 1-chloro-5-fluoro-4-methyl-2-(2-(methylsulfonyl)propan-2-yl)benzene (1.6 g, 95%) as a white solid.

LC/MS ESI (+): 265 (M+1)

$^1$H-NMR (400 MHz, CDCl$_3$): δ 7.55 (d, 1H, J=8.1 Hz), 7.09 (d, 1H, J=9.0 Hz), 2.76 (s, 3H), 2.27 (s, 3H), 2.03 (s, 6H)

(f) Synthesis of 1-(bromomethyl)-4-chloro-2-fluoro-5-(2-(methylsulfonyl)propan-2-yl)benzene The synthesis procedure of Intermediate 1-d was repeated except for using 1-chloro-5-fluoro-4-methyl-2-(2-(methylsulfonyl)propan-2-yl)benzene (1.7 g, 6.35 mmol) as a starting material to obtain 1-(bromomethyl)-4-chloro-2-fluoro-5-(2-(methylsulfonyl)propan-2-yl)benzene (2.2 g).

LC/MS ESI (+): 343 (M+1)

$^1$H-NMR (400 MHz, CDCl$_3$): δ 7.77 (d, 1H, J=7.9 Hz), 7.18 (d, 1H, J=9.1 Hz), 4.47 (s, 2H), 2.77 (s, 3H), 2.06 (s, 6H)

(g) Synthesis of 4-chloro-2-fluoro-5-(2-(methylsulfonyl)propan-2-yl)benzaldehyde The synthesis procedure of Intermediate 1-e was repeated except for using 1-(bromomethyl)-4-chloro-2-fluoro-5-(2-

(methylsulfonyl)propan-2-yl)benzene (2.2 g) as a starting material to obtain 4-chloro-2-fluoro-5-(2-(methylsulfonyl)propan-2-yl)benzaldehyde (1.0 g, 2 step yield: 57%).

$^1$H-NMR (400 MHz, CDCl$_3$): δ 10.29 (s, 1H), 8.22 (d, 1H, J=7.4 Hz), 7.34 (d, 1H, J=9.6 Hz), 2.78 (s, 3H), 2.09 (s, 6H)

(h) Synthesis of methyl 6-chloro-5-(2-(methylsulfonyl)propan-2-yl)benzo[b]thiophene-2-carboxylate The synthesis procedure of Intermediate 1-f was repeated except for using 4-chloro-2-fluoro-5-(2-(methylsulfonyl)propan-2-yl)benzaldehyde (1.0 g, 3.59 mmol) as a starting material to obtain methyl 6-chloro-5-(2-(methylsulfonyl)propan-2-yl)benzo[b]thiophene-2-carboxylate (1.1 g, 91%).

$^1$H-NMR (400 MHz, CDCl$_3$): δ 8.27 (s, 1H), 8.03 (s, 1H), 7.94 (s, 1H), 3.96 (s, 3H), 2.79 (s, 3H), 2.14 (s, 6H)

(i) Synthesis of 6-chloro-5-(2-(methylsulfonyl)propan-2-yl)benzo[b]thiophene-2-carboxylic acid The synthesis procedure of Intermediate 1-g was repeated except for using methyl 6-chloro-5-(2-(methylsulfonyl)propan-2-yl)benzo[b]thiophene-2-carboxylate (1.1 g, 3.26 mmol) as a starting material to obtain 6-chloro-5-(2-(methylsulfonyl)propan-2-yl)benzo[b]thiophene-2-carboxylic acid (998.0 mg, 92%).

$^1$H-NMR (400 MHz, DMSO-d$_6$): δ 13.67 (brs, 1H), 8.44 (s, 1H), 8.26 (s, 1H), 8.14 (s, 1H), 2.88 (s, 3H), 2.04 (s, 6H)

Intermediate 8) Synthesis of 5-(2-(methylsulfonyl)propan-2-yl)thieno[2,3-C]pyridine-2-carboxylic acid (a) Synthesis of 2-(bromomethyl)-4-methyl-5-nitropyridine The synthesis procedure of Intermediate 1-d was repeated except for using 2,4-dimethyl-5-nitropyridine (2.5 g, 16.43 mmol) as a starting material to obtain 2-(bromomethyl)-4-methyl-5-nitropyridine (1.1 g, 28%).

LC/MS ESI (+): 231 (M+1)
$^1$H-NMR (400 MHz, CDCl$_3$): δ 9.11 (s, 1H), 7.74 (s, 1H), 4.75 (s, 2H), 2.59 (s, 3H)

(b) Synthesis of 4-methyl-2-((methylsulfonyl)methyl)-5-nitropyridine

The synthesis procedure of Intermediate 1-b was repeated except for using 2-(bromomethyl)-4-methyl-5-nitropyridine (1.1 g, 4.76 mmol) as a starting material to obtain 4-methyl-2-((methylsulfonyl)methyl)-5-nitropyridine (980.0 mg, 89%).

LC/MS ESI (+): 231 (M+1)
$^1$H-NMR (400 MHz, CDCl$_3$): δ 9.15 (s, 1H) 7.50 (s, 1H), 4.46 (s, 2H), 2.98 (s, 3H), 2.69 (s, 3H)

(c) Synthesis of 4-methyl-2-(2-(methylsulfonyl)propan-2-yl)-5-nitropyridine

4-Methyl-2-((methylsulfonyl)methyl)-5-nitropyridine (980.0 mg, 4.25 mmol) was dissolved in anhydrous DMF (21.2 mL), and 60 wt % NaH (426.0 mg, 10.64 mmol) and CH$_3$I (0.8 mL, 12.75 mmol) were added at 0° C. The reaction mixture was stirred at room temperature for 16 hours, H$_2$O was added at 0° C., and extracted with EtOAc. The organic extract was washed with brine, dried over anhydrous Na$_2$SO$_4$ and concentrated under reduced pressure. The residue was purified by flash column chromatography (silica gel, n-Hex:EtOAc=2:1) to obtain 4-methyl-2-(2-(methylsulfonyl)propan-2-yl)-5-nitropyridine (290.0 mg, 26%) as a white solid.

LC/MS ESI (+): 259 (M+1)
$^1$H-NMR (400 MHz, CDCl$_3$): δ 9.14 (s, 1H) 7.65 (s, 1H), 2.82 (s, 3H), 2.69 (s, 3H), 1.92 (s, 6H)

(d) Synthesis of (E)-N,N-dimethyl-2-(2-(2-(methylsulfonyl)propan-2-yl)-5-nitropyridin-4-yl)ethene-1-amine 4-Methyl-2-(2-(methylsulfonyl)propan-2-yl)-5-nitropyridine (250.0 mg, 0.97 mmol) was dissolved in anhydrous DMF (1.2 mL) and N,N-dimethylformamide dimethylacetal (1.3 mL, 9.68 mmol) was added. The reaction mixture was stirred for 1 hour, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=1:1) to obtain (E)-N,N-dimethyl-2-(2-(2-(methylsulfonyl)propan-2-yl)-5-nitropyridin-4-yl)ethene-1-amine (250.0 mg, 82%) as a red solid.

$^1$H-NMR (400 MHz, CDCl$_3$): δ 8.93 (s, 1H) 7.58 (s, 1H), 7.35 (d, 1H, J=13.2 Hz), 5.98 (d, 1H, J=13.2 Hz), 3.05 (s, 6H), 2.95 (s, 3H), 1.87 (s, 6H)

(e) Synthesis of 2-(2-(methylsulfonyl)propan-2-yl)-5-nitroisonicotinaldehyde (E)-N,N-dimethyl-2-(2-(2-(methylsulfonyl)propan-2-yl)-5-nitropyridin-4-yl)ethene-1-amine (250.0 mg, 0.80 mmol) was dissolved in THF (4.0 mL) and H$_2$O (4.0 mL), and sodium metaperiodate (512.0 mg, 2.39 mmol) was added. The reaction mixture was stirred at 40° C. for 5 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=1:1) to obtain 2-(2-(methylsulfonyl)propan-2-yl)-5-nitroisonicotinaldehyde (130.0 mg, 60%) as a yellow solid.

LC/MS ESI (+): 273 (M+1)
$^1$H-NMR (400 MHz, CDCl$_3$): δ 10.55 (s, 1H) 9.41 (s, 1H), 8.06 (s, 1H), 2.87 (s, 3H), 1.95 (s, 6H)

(f) Synthesis of methyl 5-(2-(methylsulfonyl)propan-2-yl)thieno[2,3-c]pyridine-2-carboxylate The synthesis procedure of Intermediate 1-f was repeated except for using 2-(2-(methylsulfonyl)propan-2-yl)-5-nitroisonicotinaldehyde (130.0 mg, 0.48 mmol) as a starting material to obtain methyl 5-(2-(methylsulfonyl)propan-2-yl)thieno[2,3-c]pyridine-2-carboxylate (110.0 mg, 74%).

LC/MS ESI (+): 314 (M+1)
$^1$H-NMR (400 MHz, CDCl$_3$): δ 9.16 (s, 1H) 8.10 (s, 1H), 8.07 (s, 1H), 4.00 (s, 3H), 2.82 (s, 3H), 1.98 (s, 6H)

(g) Synthesis of 5-(2-(methylsulfonyl)propan-2-yl)thieno[2,3-c]pyridine-2-carboxylic acid The synthesis procedure of Intermediate 1-g was repeated except for using methyl 5-(2-(methylsulfonyl)propan-2-yl)thieno[2,3-c]pyridine-2-carboxylate (110.0 mg, 7.64 mmol) as a starting material to obtain 5-(2-(methylsulfonyl)propan-2-yl)thieno[2,3-c]pyridine-2-carboxylic acid (100.0 mg, 95%).

LC/MS ESI (+): 300 (M+1)
$^1$H-NMR (400 MHz, DMSO-d$_6$): δ 9.37 (s, 1H) 8.28 (s, 1H), 8.16 (s, 1H), 2.86 (s, 3H), 1.86 (s, 6H)

Intermediate 9) Synthesis of 6-(2-(methylsulfonyl)propan-2-yl)benzo[b]thiophene-2-carboxylic acid (a) Synthesis of 2-fluoro-1-methyl-4-((methylsulfonyl)methyl)benzene The synthesis procedure of Intermediate 1-b was repeated except for using 4-(bromomethyl)-2-fluoro-1-methylbenzene (1.0 g, 4.92 mmol) as a starting material to obtain 2-fluoro-1-methyl-4-((methylsulfonyl)methyl)benzene (813.0 mg, 82%).
$^1$H-NMR (400 MHz, CDCl$_3$): δ 7.23 (t, 1H, J=8.1 Hz), 7.07-7.10 (m, 2H), 4.20 (s, 2H), 2.78 (s, 3H), 2.29 (s, 3H)

(b) Synthesis of 2-fluoro-1-methyl-4-(2-(methylsulfonyl)propan-2-yl)benzene

The synthesis procedure of Intermediate 1-c was repeated except for using 2-fluoro-1-methyl-4-((methylsulfonyl)methyl)benzene (813.0 mg, 4.02 mmol) as a starting material to obtain 2-fluoro-1-methyl-4-(2-(methylsulfonyl)propan-2-yl)benzene (620 mg, 67%).
$^1$H-NMR (400 MHz, CDCl$_3$): δ 7.26-7.32 (m, 2H), 7.21 (t, 1H, J=8.4 Hz), 2.54 (s, 3H), 2.28 (s, 3H), 1.82 (s, 6H)

(c) Synthesis of 1-(bromomethyl)-2-fluoro-4-(2-(methylsulfonyl)propan-2-yl)benzene The synthesis procedure of Intermediate 1-d was repeated except for using 2-fluoro-1-methyl-4-(2-(methylsulfonyl)propan-2-yl)benzene (620.0 mg, 2.69 mmol) to obtain 1-(bromomethyl)-2-fluoro-4-(2-(methylsulfonyl)propan-2-yl)benzene (680.0 mg, 79%).
$^1$H-NMR (400 MHz, CDCl$_3$): δ 7.35-7.46 (m, 3H), 4.51 (s, 2H), 2.58 (s, 3H), 1.84 (s, 6H)

(d) Synthesis of 2-fluoro-4-(2-(methylsulfonyl)propan-2-yl)benzaldehyde

The synthesis procedure of Intermediate 1-e was repeated except for using 1-(bromomethyl)-2-fluoro-4-(2-(methylsulfonyl)propan-2-yl)benzene (650.0 mg, 2.10 mmol) as a starting material to obtain 2-fluoro-4-(2-(methylsulfonyl)propan-2-yl)benzaldehyde (330.0 mg, 64%).
$^1$H-NMR (400 MHz, CDCl$_3$): δ 10.23 (s, 1H), 7.88 (t, 1H, J=8.3 Hz), 7.60-7.64 (m, 2H), 2.78 (s, 3H), 1.78 (s, 6H)

(e) Synthesis of methyl 6-(2-(methylsulfonyl)propan-2-yl)benzo[b]thiophene-2-carboxylate The synthesis procedure of Intermediate 1-f was repeated except for using 2-fluoro-4-(2-(methylsulfonyl)propan-2-yl)benzaldehyde (350.0 mg, 1.43 mmol) as a starting material to obtain methyl 6-(2-(methylsulfonyl)propan-2-yl)benzo[b]thiophene-2-carboxylate (265.0 mg, 59%).
$^1$H-NMR (400 MHz, CDCl$_3$): δ 8.33 (s, 1H), 8.22 (s, 1H), 8.04 (d, 1H, J=8.6 Hz), 7.73 (dd, 1H, J=8.6, 1.7 Hz), 3.90 (s, 3H), 2.74 (s, 3H), 1.84 (s, 6H)

(f) Synthesis of 6-(2-(methylsulfonyl)propan-2-yl)benzo[b]thiophene-2-carboxylic acid The synthesis procedure of Intermediate 1-g was repeated except for using methyl 6-(2-(methylsulfonyl)propan-2-yl)benzo[b]thiophene-2-carboxylate (265.0 mg, 0.85 mmol) as a starting material to obtain 6-(2-(methylsulfonyl)propan-2-yl)benzo[b]thiophene-2-carboxylic acid (230.0 mg, 91%).
LC/MS ESI (−): 297 (M−1)

Intermediate 10) Synthesis of 5-(4-(methylsulfonyl)tetrahydro-2H-pyran-4-yl)benzo[b]thiophene-2-carboxylic acid (a) Synthesis of 4-(4-fluoro-3-methylphenyl)tetrahydro-2H-pyran-4-ol 4-Bromo-1-fluoro-2-methylbenzene (1.0 g, 5.29 mmol) was dissolved in anhydrous THF (26.0 mL), and 1.6M solution of n-BuLi in THF (3.5 mL, 5.55 mmol) and tetrahydro-4H-pyran-4-one (556.0 mg, 5.55 mmol) were added at −78° C. The reaction mixture was stirred at 0° C. for 2 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=1:1) to obtain 4-(4-fluoro-3-methylphenyl)tetrahydro-2H-pyran-4-ol (800.0 mg, 72%) as a white solid.
$^1$H-NMR (400 MHz, CDCl$_3$): δ 7.31 (dd, 1H, J=7.3, 2.2 Hz), 7.26 (m, 1H), 6.99 (t, 1H, J=8.9 Hz), 3.84-3.98 (m, 4H), 2.29 (s, 3H), 2.08-2.18 (m, 2H), 1.65-1.69 (m, 3H)

(b) Synthesis of 4-(4-fluoro-3-methylphenyl)tetrahydro-2H-pyran-4-thiol

The synthesis procedure of Intermediate 7-c was repeated except for using 4-(4-fluoro-3-methylphenyl)tetrahydro-2H-pyran-4-ol (800.0 mg, 3.80 mmol) as a starting material to obtain 4-(4-fluoro-3-methylphenyl)tetrahydro-2H-pyran-4-thiol (450.0 mg, 52%).
$^1$H-NMR (400 MHz, DMSO-d$_6$): δ, 7.40 (dd, 1H, J=7.4, 2.4 Hz), 7.32 (m, 1H), 7.10 (t, 1H, J=8.9 Hz), 3.76-3.82 (m, 2H), 3.65-3.69 (m, 2H), 3.26 (s, 1H), 2.24 (s, 3H), 2.08-2.18 (m, 4H)

(c) Synthesis of 4-(4-fluoro-3-methylphenyl)-4-(methylthio)tetrahydro-2H-pyran

The synthesis procedure of Intermediate 7-d was repeated except for using 4-(4-fluoro-3-methylphenyl)tetrahydro-2H-pyran-4-thiol (450.0 g, 1.99 mmol) as a starting material to obtain 4-(4-fluoro-3-methylphenyl)-4-(methylthio)tetrahydro-2H-pyran (300.0 mg, 63%).
$^1$H-NMR (400 MHz, DMSO-d$_6$): δ 7.33 (d, 1H, J=7.4 Hz), 7.25 (m, 1H), 7.09 (t, 1H, J=9.0 Hz), 3.77-3.82 (m, 2H), 3.57-3.62 (m, 2H), 2.24 (s, 3H), 2.04-2.12 (m, 4H), 1.60 (s, 3H)

(d) Synthesis of 4-(4-fluoro-3-methylphenyl)-4-(methylsulfonyl)tetrahydro-2H-pyran The synthesis procedure of Intermediate 7-e was repeated except for using 4-(4-fluoro-3-methylphenyl)-4-(methylthio)tetrahydro-2H-pyran (300.0 mg, 1.25 mmol) as a starting material to obtain 4-(4-fluoro-3-methylphenyl)-4-(methylsulfonyl)tetrahydro-2H-pyran (300.0 mg, 89%).
$^1$H-NMR (400 MHz, CDCl$_3$): δ 7.39 (dd, 1H, J=7.0, 2.4 Hz), 7.33 (m, 1H), 7.10 (t, 1H, J=8.8 Hz), 3.98-4.02 (m, 2H), 3.40 (t, 2H, J=11.7 Hz), 2.55-2.63 (m, 2H), 2.42-2.47 (m, 5H), 2.33 (s, 3H)

(e) Synthesis of 4-(3-(bromomethyl)-4-fluorophenyl)-4-(methylsulfonyl)tetrahydro-2H-pyran The synthesis procedure of Intermediate 1-d was repeated except for using 4-(4-fluoro-3-methylphenyl)-4-(methylsulfonyl)tetrahydro-2H-pyran (300.0 mg, 1.10 mmol) as a starting material to obtain 4-(3-(bromomethyl)-4-fluorophenyl)-4-(methylsulfonyl)tetrahydro-2H-pyran (340.0 mg, 88%).
$^1$H-NMR (400 MHz, CDCl$_3$): δ 7.59 (dd, 1H, J=6.9, 2.6 Hz), 7.50 (m, 1H), 7.19 (t, 1H, J=8.9 Hz), 4.54 (s, 2H), 3.98-4.02 (m, 2H), 3.36-3.42 (m, 2H), 2.55-2.65 (m, 2H), 2.42-2.50 (m, 5H)

(f) Synthesis of 2-fluoro-5-(4-(methylsulfonyl)tetrahydro-2H-pyran-4-yl)benzaldehyde The synthesis procedure of Intermediate 1-e was repeated except for using 4-(3-(bromomethyl)-4-fluorophenyl)-4-(methylsulfonyl)tetrahydro-2H-pyran (350.0 mg, 1.00 mmol) as a starting material to obtain 2-fluoro-5-(4-(methylsulfonyl)tetrahydro-2H-pyran-4-yl)benzaldehyde (220.0 mg, 76%).
LC/MS ESI (−): 285 (M−1)

(g) Synthesis of methyl 5-(4-(methylsulfonyl)tetrahydro-2H-pyran-4-yl)benzo[b]thiophene-2-carboxylate The synthesis procedure of Intermediate 1-f was repeated except for using 2-fluoro-5-(4-(methylsulfonyl)tetrahydro-2H-pyran-4-yl)benzaldehyde (110.0 mg, 0.38 mmol) as a starting material to obtain methyl 5-(4-(methylsulfonyl)tetrahydro-2H-pyran-4-yl)benzo[b]thiophene-2-carboxylate (124.0 mg, 91%).
$^1$H-NMR (400 MHz, CDCl$_3$): δ, 8.06-8.09 (m, 2H), 7.97 (d, 1H, J=8.7 Hz), 7.66 (dd, 1H, J=8.7, 1.9 Hz), 4.03-4.06 (m, 2H), 3.97 (s, 3H), 3.43 (t, 2H, J=11.6 Hz), 2.56-2.72 (m, 4H), 2.49 (s, 3H)

(h) Synthesis of 5-(4-(methylsulfonyl)tetrahydro-2H-pyran-4-yl)benzo[b]thiophene-2-carboxylic acid The synthesis procedure of Intermediate 1-g was repeated except for using methyl 5-(4-(methylsulfonyl)tetrahydro-2H-pyran-4-yl)benzo[b]thiophene-2-carboxylate (124.0 mg, 0.35 mmol) as a starting material to obtain 5-(4-(methylsulfonyl)tetrahydro-2H-pyran-4-yl)benzo[b]thiophene-2-carboxylic acid (104.0 mg, 87%).
LC/MS ESI (−): 339 (M−1)

Intermediate 11) Synthesis of 6-(2-(methylsulfonyl)propan-2-yl)-1H-indole-2-carboxylic acid (a) Synthesis of 2-(3-bromo-4-methylphenyl)propan-2-ol The synthesis procedure of Intermediate 7-b was repeated except for using 1-(3-bromo-4-methylphenyl)ethan-1-one (1.0 g, 4.69 mmol) as a starting material to obtain 2-(3-bromo-4-methylphenyl)propan-2-ol (1.0 g, 96%).
$^1$H-NMR (400 MHz, CDCl$_3$): δ 7.67 (d, 1H, J=1.8 Hz), 7.31 (dd, 1H, J=7.9, 1.8 Hz), 7.20 (d, 1H, J=7.9 Hz), 2.38 (s, 3H), 1.70 (s, 1H), 1.56 (s, 6H)

(b) Synthesis of 2-(3-bromo-4-methylphenyl)propane-2-thiol

The synthesis procedure of Intermediate 7-c was repeated except for using 2-(3-bromo-4-methylphenyl)propan-2-ol (1.0 g, 4.50 mmol) as a starting material to obtain 2-(3-bromo-4-methylphenyl)propane-2-thiol (1.0 g, 92%).
$^1$H-NMR (400 MHz, CDCl$_3$): 0.5-7.71 (s, 1H), 7.40 (d, 1H, J=8.0 Hz), 7.18 (d, 1H, J=8.0 Hz), 2.37 (s, 3H), 2.24 (s, 1H), 1.79 (s, 6H)

(c) Synthesis of (2-(3-bromo-4-methylphenyl)propan-2-yl)(methyl)sulfane

The synthesis procedure of Intermediate 7-d was repeated except for using 2-(3-bromo-4-methylphenyl)propane-2-thiol (1.0 g, 4.08 mmol) as a starting material to obtain (2-(3-bromo-4-methylphenyl)propan-2-yl)(methyl)sulfane (872.7 mg, 83%).
$^1$H-NMR (400 MHz, CDCl$_3$): δ 7.65 (d, 1H, J=2.0 Hz), 7.36 (dd, 1H, J=8.0, 2.0 Hz), 7.18 (d, 1H, J=8.0 Hz), 2.37 (s, 3H), 1.79 (s, 3H), 1.66 (s, 6H)

(d) Synthesis of 2-bromo-1-methyl-4-(2-(methylsulfonyl)propan-2-yl)benzene

The synthesis procedure of Intermediate 7-e was repeated except for using (2-(3-bromo-4-methylphenyl)propan-2-yl)(methyl)sulfane (871.0 mg, 3.36 mmol) as a starting material to obtain 2-bromo-1-methyl-4-(2-(methylsulfonyl)propan-2-yl)benzene (973.7 mg, quant).
$^1$H-NMR (400 MHz, CDCl$_3$): δ 7.76 (s, 1H), 7.51 (d, 1H, J=8.1 Hz), 7.27 (d, 1H, J=8.1 Hz), 2.56 (s, 3H), 2.41 (s, 3H), 1.82 (s, 6H)

(e) Synthesis of 2-bromo-1-(bromomethyl)-4-(2-(methylsulfonyl)propan-2-yl)benzene The synthesis procedure of Intermediate 1-d was repeated except for using 2-bromo-1-methyl-4-(2-(methylsulfonyl)propan-2-yl)benzene (972.0 mg, 3.34 mmol) as a starting material to obtain 2-bromo-1-(bromomethyl)-4-(2-(methylsulfonyl)propan-2-yl)benzene (894.4 mg, 72%).
$^1$H-NMR (400 MHz, CDCl$_3$): δ 7.82 (d, 1H, J=2.0 Hz), 7.61 (dd, 1H, J=8.2, 2.0 Hz), 7.50 (d, 1H, J=8.2 Hz), 4.59 (s, 2H), 2.59 (s, 3H), 1.84 (s, 6H)

(f) Synthesis of 2-bromo-4-(2-(methylsulfonyl)propan-2-yl)benzaldehyde

The synthesis procedure of Intermediate 1-e was repeated except for using 2-bromo-1-(bromomethyl)-4-(2-(methylsulfonyl)propan-2-yl)benzene (890.0 mg, 2.41 mmol) as a starting material to obtain 2-bromo-4-(2-(methylsulfonyl)propan-2-yl)benzaldehyde (475.9 mg, 65%).
$^1$H-NMR (400 MHz, CDCl$_3$): δ 10.36 (s, 1H), 7.94 (d, 1H, J=8.3 Hz), 7.92 (d, 1H, J=1.8 Hz), 7.74 (dd, 1H, J=8.3, 1.2 Hz), 2.62 (s, 3H), 1.88 (s, 6H)

(g) Synthesis of methyl (Z)-2-(((benzyloxy)carbonyl)amino)-3-(2-bromo-4-(2-(methylsulfonyl)propan-2-yl)phenyl)acrylate 2-Bromo-4-(2-(methylsulfonyl)propan-2-yl)benzaldehyde (441.0 mg, 1.45 mmol), methyl 2-(((benzyloxy)carbonyl)amino)-2-(dimethoxyphosphoryl)acetate (622.0 mg, 1.88 mmol) and DBU (330.0 mg, 2.17 mmol) were dissolved in CH$_2$Cl$_2$ (14.5 mL). The reaction mixture was stirred at room temperature for 30 minutes, H$_2$O was added, and extracted with CH$_2$Cl$_2$. The organic extract was washed with brine, dried over anhydrous Na$_2$SO$_4$ and concentrated under reduced pressure. The residue was purified by flash column chromatography (amine silica gel, n-Hex:EtOAc=1:1) to obtain methyl (Z)-2-(((benzyloxy)carbonyl)amino)-3-(2-bromo-4-(2-(methylsulfonyl)propan-2-yl)phenyl)acrylate (570.0 mg, 77%).

LC/MS ESI (+): 510 (M+1)

$^1$H-NMR (400 MHz, CDCl$_3$): δ 7.82 (s, 1H), 7.51 (s, 2H), 7.32-7.37 (m, 4H), 7.26-7.29 (m, 2H), 6.55 (brs, 1H), 5.04 (s, 2H), 3.87 (s, 3H), 2.53 (s, 3H), 1.82 (s, 6H)

(h) Synthesis of methyl 6-(2-(methylsulfonyl)propan-2-yl)-1H-indole-2-carboxylate Methyl (Z)-2-(((benzyloxy)carbonyl)amino)-3-(2-bromo-4-(2-(methylsulfonyl)propan-2-yl)phenyl)acrylate (570.0 mg, 1.12 mmol), CuI (42.5 mg, 0.22 mmol), L-proline (51.4 mg, 0.45 mmol) and K$_2$CO$_3$ (463.0 mg, 3.35 mmol) were dissolved in 1,4-dioxane (5.6 mL). The reaction mixture was stirred at 100° C. for 2 days, H$_2$O was added, and extracted with EtOAc. The organic extract was washed with brine, dried over anhydrous Na$_2$SO$_4$ and concentrated under reduced pressure. The residue was purified by flash column chromatography (amine silica gel, n-Hex:EtOAc=1:1) to obtain methyl 6-(2-(methylsulfonyl)propan-2-yl)-1H-indole-2-carboxylate (227.0 mg, 69%).

$^1$H-NMR (400 MHz, DMSO-d$_6$): δ 12.02 (s, 1H), 7.67-7.69 (m, 2H), 7.37 (dd, 1H, J=8.6, 1.8 Hz), 7.16 (d, 1H, J=1.5 Hz), 3.88 (s, 3H), 2.68 (s, 3H), 1.80 (s, 6H)

(i) Synthesis of 6-(2-(methylsulfonyl)propan-2-yl)-1H-indole-2-carboxylic acid hydrochloride The synthesis procedure of Intermediate 1-g was repeated except for using methyl 6-(2-(methylsulfonyl)propan-2-yl)-1H-indole-2-carboxylate (227.0 mg, 0.77 mmol) as a starting material to obtain 6-(2-(methylsulfonyl)propan-2-yl)-1H-indole-2-carboxylic acid hydrochloride (170.0 mg, 79%).

$^1$H-NMR (400 MHz, DMSO-d$_6$): δ 13.02 (brs, 1H), 11.82 (s, 1H), 7.64-7.67 (m, 2H), 7.35 (dd, 1H, J=8.8, 1.6 Hz), 7.07 (d, 1H, J=1.6 Hz), 2.67 (s, 3H), 1.80 (s, 6H)

Intermediate 12) Synthesis of 5-(2-((2-methoxyethyl)sulfonyl)propan-2-yl)benzo[b]thiophene-2-carboxylic acid (a) Synthesis of 2-(4-fluoro-3-methylphenyl)propan-2-ol The synthesis procedure of Intermediate 7-b was repeated except for using 1-(4-fluoro-3-methylphenyl)ethan-1-one (1.0 g, 6.57 mmol) as a starting material to obtain 2-(4-fluoro-3-methylphenyl)propan-2-ol (872.0 mg, 79%).

$^1$H-NMR (400 MHz, CDCl$_3$): δ 7.31 (dd, 1H, J=7.4, 2.1 Hz), 7.25 (m, 1H), 6.95 (t, 1H, J=8.9 Hz), 2.28 (s, 3H), 1.71 (s, 1H), 1.57 (s, 6H)

(b) Synthesis of 2-(4-fluoro-3-methylphenyl)propane-2-thiol

The synthesis procedure of Intermediate 7-c was repeated except for using 2-(4-fluoro-3-methylphenyl)propan-2-ol (872.0 mg, 5.18 mmol) as a starting material to obtain 2-(4-fluoro-3-methylphenyl)propane-2-thiol (955.0 mg, 85%).

$^1$H-NMR (400 MHz, CDCl$_3$): δ 7.37 (dd, 1H, J=7.1, 2.3 Hz), 7.32 (m, 1H), 6.93 (t, 1H, J=8.9 Hz), 2.28 (s, 3H), 2.24 (s, 1H), 1.81 (s, 6H)

(c) Synthesis of (2-(4-fluoro-3-methylphenyl)propan-2-yl)(2-methoxyethyl)sulfane 2-(4-Fluoro-3-methylphenyl)propane-2-thiol (400.0 mg, 2.17 mmol) was dissolved in anhydrous DMF (16.3 mL), and 1-bromo-2-methoxyethane (392.0 mg, 2.82 mmol) and Cs$_2$CO$_3$ (1.4 g, 4.34 mmol) were added. The reaction mixture was stirred at 70° C. for 5 hours, cooled to room temperature, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain (2-(4-fluoro-3-methylphenyl)propan-2-yl)(2-methoxyethyl)sulfane (420.0 mg, 80%) as a white solid.

$^1$H-NMR (400 MHz, CDCl$_3$): δ 7.34 (dd, 1H, J=7.4, 2.3 Hz), 7.29 (m, 1H), 6.92 (t, 1H, J=8.9 Hz), 3.32 (t, 2H, J=6.7 Hz), 3.26 (s, 3H), 2.43 (t, 2H, J=6.7 Hz), 2.27 (s, 3H), 1.68 (s, 6H)

(d) Synthesis of 1-fluoro-4-(2-((2-methoxyethyl)sulfonyl)propan-2-yl)-2-methylbenzene The synthesis procedure of Intermediate 7-e was repeated except for using (2-(4-fluoro-3-methylphenyl)propan-2-yl)(2-methoxyethyl)sulfane (420.0 mg, 1.73 mmol) as a starting material to obtain 1-fluoro-4-(24(2-methoxyethyl)sulfonyl)propan-2-yl)-2-methylbenzene (410.0 mg, 86%).

$^1$H-NMR (400 MHz, CDCl$_3$): δ 7.32-7.40 (m, 2H), 7.02 (t, 1H, J=8.9 Hz), 3.64 (t, 2H, J=6.7 Hz), 3.29 (s, 3H), 2.91 (t, 2H, J=6.7 Hz), 2.30 (s, 3H), 1.82 (s, 6H) (e) Synthesis of 2-(bromomethyl)-1-fluoro-4-(24(2-methoxyethyl)sulfonyl)propan-2-yl)benzene The synthesis procedure of Intermediate 1-d was repeated except for using 1-fluoro-4-(2-((2-methoxyethyl)sulfonyl)propan-2-yl)-2-methylbenzene (410.0 mg, 1.49 mmol) as a starting material to obtain 2-(bromomethyl)-1-fluoro-4-(2-((2-methoxyethyl)sulfonyl)propan-2-yl)benzene (40.0 mg, 8%).

$^1$H-NMR (400 MHz, CDCl$_3$): δ 7.65 (dd, 1H, J=7.0, 2.6 Hz), 7.58 (m, 1H), 7.10 (t, 1H, J=9.0 Hz), 4.52 (s, 2H), 3.64 (t, 2H, J=6.5 Hz), 3.29 (s, 3H), 2.93 (t, 2H, J=6.5 Hz), 1.84 (s, 6H)

(f) Synthesis of 2-fluoro-5-(2-((2-methoxyethyl)sulfonyl)propan-2-yl)benzaldehyde The synthesis procedure of Intermediate 1-e was repeated except for using 2-(bromomethyl)-1-fluoro-4-(2-(2-methoxyethyl)sulfonyl)propan-2-yl)benzene (60.0 mg, 0.17 mmol) as a starting material to obtain 2-fluoro-5-(2-((2-methoxyethyl)sulfonyl)propan-2-yl)benzaldehyde (36.0 mg, 74%).

$^1$H-NMR (400 MHz, CDCl$_3$): δ 10.30 (s, 1H), 7.99 (dd, 1H, J=6.4, 2.7 Hz), 7.93 (m, 1H), 7.17 (t, 1H, J=9.2 Hz), 3.62 (t, 2H, J=6.4 Hz), 3.23 (s, 3H), 2.87 (t, 2H, J=6.4 Hz), 1.80 (s, 6H)

(g) Synthesis of methyl 5-(2-((2-methoxyethyl)sulfonyl)propan-2-yl)benzo[b]thiophene-2-carboxylate The synthesis procedure of Intermediate 1-f was repeated except for using 2-fluoro-5-(2-(2-methoxyethyl)sulfonyl)propan-2-yl)benzaldehyde (36.0 mg, 0.13 mmol) as a starting material to obtain methyl 5-(2-(2-methoxyethyl)sulfonyl)propan-2-yl)benzo[b]thiophene-2-carboxylate (30.0 mg, 67%).

¹H-NMR (400 MHz, CDCl₃): δ 8.10 (s, 1H), 8.07 (s, 1H), 7.90 (d, 1H, J=8.7 Hz), 7.78 (dd, 1H, J=8.7, 2.0 Hz), 3.96 (s, 3H), 3.63 (t, 2H, J=6.4 Hz), 3.25 (s, 3H), 2.91 (t, 2H, J=6.4 Hz), 1.93 (s, 6H)

(h) Synthesis of 5-(2-((2-methoxyethyl)sulfonyl)propan-2-yl)benzo[b]thiophene-2-carboxylic acid The synthesis procedure of Intermediate 1-g was repeated except for using methyl 5-(2-((2-methoxyethyl)sulfonyl)propan-2-yl)benzo[b]thiophene-2-carboxylate (30.0 mg, 0.08 mmol) as a starting material to obtain 5-(2-(2-methoxyethyl)sulfonyl)propan-2-yl)benzo[b]thiophene-2-carboxylic acid (27.0 mg, 94%).
LC/MS ESI (−): 341 (M−1)

Intermediate 13) Synthesis of 5-((S-methylsulfonimidoyl)methyl)benzo[b]thiophene-2-carboxylic acid (a) Synthesis of (4-fluoro-3-methylbenzyl)(methyl)sulfane 4-(Bromomethyl)-1-fluoro-2-methylbenzene (1.0 g, 4.92 mmol) and sodium methanethiolate (380.0 mg, 5.42 mmol) were dissolved in DMF (24.6 mL). The reaction mixture was stirred at room temperature for 16 hours, H₂O was added, and extracted with EtOAc. The organic extract was washed with brine, dried over anhydrous Na₂SO₄ and concentrated under reduced pressure. The residue was purified by flash column chromatography (silica gel, n-Hex:CH₂Cl₂=4:1) to obtain (4-fluoro-3-methylbenzyl)(methyl)sulfane (709.0 mg, 85%) as a colorless liquid.
¹H-NMR (400 MHz, CDCl₃): δ 7.12 (d, 1H, J=7.3 Hz), 7.06 (m, 1H), 6.93 (m, 1H), 3.61 (s, 2H), 2.26 (s, 3H), 1.99 (s, 3H)

(b) Synthesis of (E)-N-((4-fluoro-3-methylbenzyl)(methyl)-λ⁴-sulfanylidene)-4-nitrobenzenesulfonamide (4-Fluoro-3-methylbenzyl)(methyl)sulfane (600.0 mg, 3.52 mmol), 4-nitrobenzenesulfonamide (869.0 mg, 4.39 mmol) and (diacetoxyiodo)benzene (1.7 g, 5.37 mmol) were dissolved in CH₃CN (35.8 mL). The reaction mixture was stirred at 90° C. for 16 hours, cooled to room temperature, and concentrated under reduced pressure. The residue was purified by reversed-phase column chromatography (C18-silica gel, CH₃CN:H₂O) to obtain (E)-N-((4-fluoro-3-methylbenzyl)(methyl)-λ⁴-sulfanylidene)-4-nitrobenzenesulfonamide (606.0 mg, 46%).
LC/MS ESI (+): 371 (M+1)
¹H-NMR (400 MHz, CDCl₃): δ 8.18 (d, 2H, J=8.9 Hz), 7.88 (d, 2H, J=8.9 Hz), 7.01-7.05 (m, 2H), 6.91 (m, 1H), 4.16 (d, 1H, J=12.8 Hz), 4.07 (d, 1H, J=12.8 Hz), 2.66 (s, 3H), 2.20 (d, 3H, J=1.9 Hz)

(c) Synthesis of N-((4-fluoro-3-methylbenzyl)(methyl)(oxo)-λ⁶-sulfanylidene)-4-nitrobenzene sulfonamide (E)-N-((4-fluoro-3-methylbenzyl)(methyl)-λ⁴-sulfanylidene)-4-nitrobenzene sulfonamide (600.0 mg, 1.62 mmol), RuCl₃H₂O (36.5 mg, 0.16 mmol) and NaIO₄ (520.0 mg, 2.43 mmol) were dissolved in a mixture of CH₂Cl₂/H₂O (16.3 mL, 10/3 v/v). The reaction mixture was stirred at room temperature for 16 hours, H₂O was added, and extracted with CH₂Cl₂. The organic extract was washed with brine, dried over anhydrous Na₂SO₄ and concentrated under reduced pressure. The residue was purified by flash column chromatography (amine silica gel, n-Hex:EtOAc=1:2) to obtain N-((4-fluoro-3-methylbenzyl)(methyl)(oxo)-λ⁶-sulfanylidene)-4-nitrobenzene sulfonamide (546.0 mg, 87%).
¹H-NMR (400 MHz, CDCl₃): δ 8.32 (d, 2H, J=9.0 Hz), 8.14 (d, 2H, J=9.0 Hz), 7.30 (dd, 1H, J=6.9, 1.9 Hz), 7.25 (m, 1H), 7.08 (m, 1H), 4.69 (s, 2H), 3.09 (s, 3H), 2.31 (d, 3H, J=1.8 Hz)

(d) Synthesis of N-((3-(bromomethyl)-4-fluorobenzyl)(methyl)(oxo)-λ⁶-sulfanylidene)-4-nitrobenzene sulfonamide The synthesis procedure of Intermediate 1-d was repeated except for using N-((4-fluoro-3-methylbenzyl)(methyl)(oxo)-λ⁶-sulfanylidene)-4-nitrobenzene sulfonamide (546.0 mg, 1.41 mmol) as a starting material to obtain N-((3-(bromomethyl)-4-fluorobenzyl)(methyl)(oxo)-?⁶-sulfanylidene)-4-nitrobenzene sulfonamide (657.0 mg, quant).
¹H-NMR (400 MHz, CDCl₃): δ 8.32 (d, 2H, J=9.0 Hz), 8.13 (d, 2H, J=9.0 Hz), 7.52 (m, 1H), 7.43 (m, 1H), 7.17 (m, 1H), 4.72 (s, 2H), 4.51 (s, 2H), 3.13 (s, 3H)

(e) Synthesis of N-((4-fluoro-3-formylbenzyl)(methyl)(oxo)-λ⁶-sulfanylidene)-4-nitrobenzene sulfonamide The synthesis procedure of Intermediate 1-e was repeated except for using N-((3-(bromomethyl)-4-fluorobenzyl)(methyl)(oxo)-λ⁶-sulfanylidene)-4-nitrobenzene sulfonamide (657.0 mg, 1.41 mmol) as a starting material to obtain N-((4-fluoro-3-formylbenzyl)(methyl)(oxo)-λ⁶-sulfanylidene)-4-nitrobenzene sulfonamide (357.7 mg, 63%).
¹H-NMR (400 MHz, CDCl₃): δ 10.38 (s, 1H), 8.33 (d, 2H, J=8.8 Hz), 8.14 (d, 2H, J=8.8 Hz), 7.92 (dd, 1H, J=6.2, 2.4 Hz), 7.82-7.86 (m, 1H), 7.34 (m, 1H), 4.75-4.83 (m, 2H), 3.14 (s, 3H)

(f) Synthesis of methyl 5-((S-methylsulfonimidoyl)methyl)benzo[b]thiophene-2-carboxylate The synthesis procedure of Intermediate 1-f was repeated except for using N-((4-fluoro-3-formylbenzyl)(methyl)(oxo)-λ⁶-sulfanylidene)-4-nitrobenzene sulfonamide (306.0 mg, 0.77 mmol) as a starting material to obtain methyl 5-((S-methylsulfonimidoyl)methyl)benzo[b]thiophene-2-carboxylate (139.0 mg, 65%).
LC/MS ESI (+): 284 (M+1)
¹H-NMR (400 MHz, CDCl₃): δ 8.08 (s, 1H), 7.91-7.93 (m, 2H), 7.51 (dd, 1H, J=8.5, 1.7 Hz), 4.52 (d, 1H, J=13.1 Hz), 4.36 (d, 1H, J=13.1 Hz), 3.97 (s, 3H), 3.77 (s, 1H), 2.97 (s, 3H)

(g) Synthesis of 5-((S-methylsulfonimidoyl)methyl)benzo[b]thiophene-2-carboxylic acid The synthesis procedure of Intermediate 1-g was repeated except for using methyl 5-((S-methylsulfonimidoyl)methyl)benzo[b]thiophene-2-carboxylate (137.0 mg, 0.48 mmol) as a starting material to obtain 5-((S-methylsulfonimidoyl)methyl)benzo[b]thiophene-2-carboxylic acid (93.4 mg, 46%).

LC/MS ESI (+): 270 (M+1)
$^1$H-NMR (400 MHz, DMSO-$d_6$): δ 8.13 (s, 1H), 8.06 (d, 1H, J=8.3 Hz), 8.04 (s, 1H), 7.57 (dd, 1H, J=8.4, 1.4 Hz), 4.55-4.57 (m, 3H), 2.86 (d, 3H, J=3.5 Hz)

Intermediate 14) Synthesis of 5-(1,1-dioxidotetrahydrothiophen-2-yl)benzo[b]thiophene-2-carboxylic acid (a) Synthesis of methyl 5-(1,1-dioxidotetrahydrothiophen-2-yl)benzo[b]thiophene-2-carboxylate Tetrahydrothiophene 1,1-dioxide (124.0 mg, 1.03 mmol) was dissolved in anhydrous THF (7.3 mL), and 1M solution of lithium bis(trimethylsilyl)amide in THF (1.5 mL, 1.55 mmol) was added dropwise at −20° C. The reaction mixture was stirred at room temperature for 30 minutes, and ZnCl$_2$ (211.0 mg, 1.55 mmol) was added −20° C. The reaction mixture was slowly warmed to room temperature, methyl 5-bromobenzo[b]thiophene-2-carboxylate (200.0 mg, 0.74 mmol), Pd(OAc)$_2$ (8.3 mg, 0.04 mmol) and XPhos (35.2 mg, 0.07 mmol) were added, and stirred at 65° C. for 5 hours. The reaction mixture was cooled to room temperature, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain methyl 5-(1,1-dioxidotetrahydrothiophen-2-yl)benzo[b]thiophene-2-carboxylate (60.0 mg, 26%) as an off-white solid.
$^1$H-NMR (400 MHz, CDCl$_3$): δ 8.06 (s, 1H), 7.89-7.91 (m, 2H), 7.49 (dd, 1H, J=8.4, 2.0 Hz), 4.30 (m, 1H), 3.95 (s, 3H), 2.95-3.35 (m, 3H), 2.22-2.58 (m, 3H)

(b) Synthesis of 5-(1,1-dioxidotetrahydrothiophen-2-yl)benzo[b]thiophene-2-carboxylic acid The synthesis procedure of Intermediate 1-g was repeated except for using methyl 5-(1,1-dioxidotetrahydrothiophen-2-yl)benzo[b]thiophene-2-carboxylate (70.0 mg, 0.23 mmol) as a starting material to obtain 5-(1,1-dioxidotetrahydrothiophen-2-yl)benzo[b]thiophene-2-carboxylic acid (60.0 mg, 90%) as a white solid.
LC/MS ESI (−): 295 (M−1)
$^1$H-NMR (400 MHz, DMSO-$d_6$): δ 13.55 (s, 1H), 8.13 (s, 1H), 8.08 (d, 1H, J=8.5 Hz), 8.02 (s, 1H), 7.51 (d, 1H, J=8.4 Hz), 4.50 (m, 1H), 3.17-3.36 (m, 2H), 2.38-2.46 (m, 2H), 2.13-2.28 (m, 2H)

Intermediate 15) Synthesis of 5-(1,1-dioxidotetrahydro-2H-thiopyran-2-yl)benzo[b]thiophene-2-carboxylic acid (a) Synthesis of methyl 5-(1,1-dioxidotetrahydro-2H-thiopyran-2-yl)benzo[b]thiophene-2-carboxylate The synthesis procedure of Intermediate 14-a was repeated except for using methyl 5-bromobenzo[b]thiophene-2-carboxylate (95.0 mg, 0.35 mmol) and tetrahydro-2H-thiopyrane 1,1-dioxide (66.0 mg, 0.49 mmol) as a starting material to obtain methyl 5-(1,1-dioxidotetrahydro-2H-thiopyran-2-yl)benzo[b]thiophene-2-carboxylate (26.0 mg, 23%) as an off-white solid.
$^1$H-NMR (400 MHz, CDCl$_3$): δ 8.06 (s, 1H), 7.95 (s, 1H), 7.89 (d, 1H, J=8.5 Hz), 7.53 (d, 1H, J=8.5 Hz), 4.15 (m, 1H), 3.95 (s, 3H), 3.09-3.29 (m, 2H), 1.56-2.59 (m, 6H)

(b) Synthesis of 5-(1,1-dioxidotetrahydro-2H-thiopyran-2-yl)benzo[b]thiophene-2-carboxylic acid The synthesis procedure of Intermediate 1-g was repeated except for using methyl 5-(1,1-dioxidotetrahydro-2H-thiopyran-2-yl)benzo[b]thiophene-2-carboxylate (26.0 mg, 0.08 mmol) as a starting material to obtain 5-(1,1-dioxidotetrahydro-2H-thiopyran-2-yl)benzo[b]thiophene-2-carboxylic acid (22.0 mg, 88%) as a white solid.
LC/MS ESI (−): 309 (M−1)

Example 1) Synthesis of N-(3-chloro-5-(2-(3-ethoxy-5-(trifluoromethoxy)phenyl)propan-2-yl)phenyl)-5-(2-(methylsulfonyl)propan-2-yl)benzo[b]thiophene-2-carboxamide (a) Synthesis of 3-chloro-5-nitrobenzoyl chloride 3-Chloro-5-nitrobenzoic acid (5.0 g, 24.81 mmol) was dissolved in SOCl$_2$ (10.0 mL, 137.00 mmol), and a catalytic amount of anhydrous DMF was added. The reaction mixture was refluxed at 110° C. for 2 hours and concentrated under reduced pressure to obtain 3-chloro-5-nitrobenzoyl chloride (5.3 g, quant.) as a yellow liquid without purification.

(b) Synthesis of (3-chloro-5-nitrophenyl)(3-methoxy-5-(trifluoromethoxy)phenyl)methanone 3-Chloro-5-nitrobenzoyl chloride (5.0 g, 22.70 mmol) was dissolved in anhydrous Et$_2$O (230.0 mL), and (3-methoxy-5-(trifluoromethoxy)phenyl)boronic acid (5.4 g, 22.70 mmol), Pd(dba)$_2$ (1.3 g, 2.27 mmol), PPh$_3$ (1.2 g, 4.54 mmol) and copper thiophene-2-carboxylate (4.3 g, 22.70 mmol) were added. The reaction mixture was stirred at room temperature for 15 hours, filtered through Celite, and concentrated under reduced pressure. The residue was purified by flash column chromatography (amine silica gel, n-Hex:EtOAc=9:1) to obtain (3-chloro-5-nitrophenyl)(3-methoxy-5-(trifluoromethoxy)phenyl)methanone (4.2 g, 41%) as a yellow oil.
$^1$H-NMR (400 MHz, CDCl$_3$): δ 8.49 (s, 1H), 8.46 (s, 1H), 8.10 (s, 1H), 7.26 (s, 1H), 7.18 (s, 1H), 7.05 (s, 1H), 3.90 (s, 3H)

(c) Synthesis of 1-chloro-3-(dichloro(3-methoxy-5-(trifluoromethoxy)phenyl)methyl)-5-nitrobenzene (3-Chloro-5-nitrophenyl)(3-methoxy-5-(trifluoromethoxy)phenyl)methanone (4.0 g, 10.65 mmol) was dissolved in 1,2-dibromoethane (106.0 mL) and PCl$_5$ (11.1 g, 53.24 mmol) was added. The reaction mixture was stirred at 110° C. for 24 hours and cooled to room temperature. The reaction mixture was poured into a solution of NaHCO$_3$ in ice water, vigorously stirred, and extracted with CH$_2$Cl$_2$. The organic extract was dried over anhydrous Na$_2$SO$_4$ and concentrated under reduced pressure. The residue was purified by flash column chromatography (amine silica gel, n-Hex:EtOAc=20:1) to obtain 1-chloro-3-(dichloro(3-methoxy-5-(trifluoromethoxy)phenyl)methyl)-5-nitrobenzene (1.4 g, 30%) as a yellow oil.
$^1$H-NMR (400 MHz, CDCl$_3$): δ 8.37 (s, 1H), 8.24 (s, 1H), 7.91 (s, 1H), 7.08 (s, 1H), 7.05 (s, 1H), 6.81 (s, 1H), 3.84 (s, 3H)

(d) Synthesis of 1-chloro-3-(2-(3-methoxy-5-(trifluoromethoxy)phenyl)propan-2-yl)-5-nitrobenzene 1M solution of TiCl$_4$ in CH$_2$Cl$_2$ (0.6 mL, 0.63 mmol) was added to 1.2M solution of dimethylzinc in toluene (7.8 mL, 9.41 mmol) at −40° C., and stirred for 1 hour. 1-Chloro-3-(dichloro(3-methoxy-5-(trifluoromethoxy)phenyl)methyl)-5-nitrobenzene (1.4 g, 3.14 mmol) in $CH_2Cl_2$ (11.4 mL) was slowly added dropwise at −40° C., and the reaction mixture was warmed to 0° C. and stirred for 18 hours. $H_2O$ was added, and the reaction mixture was extracted with $CH_2Cl_2$. The organic extract was dried over anhydrous $Na_2SO_4$ and concentrated under reduced pressure. The residue was purified by flash column chromatography (amine silica gel, n-Hex:EtOAc=9:1) to obtain 1-chloro-3-(2-(3-methoxy-5-(trifluoromethoxy)phenyl)propan-2-yl)-5-nitrobenzene (750.0 mg, 61%) as a yellow solid.

$^1$H-NMR (400 MHz, $CDCl_3$): δ 8.07 (s, 1H), 8.00 (s, 1H), 7.48 (s, 1H), 6.62-6.65 (m, 3H), 3.78 (s, 3H), 1.70 (s, 6H)

(e) Synthesis of 3-(2-(3-chloro-5-nitrophenyl)propan-2-yl)-5-(trifluoromethoxy)phenol 1-Chloro-3-(2-(3-methoxy-5-(trifluoromethoxy)phenyl)propan-2-yl)-5-nitrobenzene (450.0 mg, 1.15 mmol) was dissolved in anhydrous $CH_2Cl_2$ (8.0 mL) and 1M solution of $BBr_3$ in $CH_2Cl_2$ (3.5 mL, 3.46 mmol) was slowly added dropwise at 0° C. The reaction mixture was stirred at room temperature for 8 hours, $H_2O$ was added at 0° C., and extracted with $CH_2Cl_2$. The organic extract was washed with brine, dried over anhydrous $Na_2SO_4$ and concentrated under reduced pressure. The residue was purified by flash column chromatography (silica gel, n-Hex:EtOAc=3:1) to obtain 3-(2-(3-chloro-5-nitrophenyl)propan-2-yl)-5-(trifluoromethoxy)phenol (380.0 mg, 88%) as a colorless oil.

$^1$H-NMR (400 MHz, $CDCl_3$): δ 8.07 (s, 1H), 8.00 (s, 1H), 7.48 (s, 1H), 6.64 (s, 1H), 6.61 (s, 1H), 6.55 (s, 1H), 5.00 (s, 1H), 1.69 (s, 6H)

(f) Synthesis of 1-chloro-3-(2-(3-ethoxy-5-(trifluoromethoxy)phenyl)propan-2-yl)-5-nitrobenzene 3-(2-(3-Chloro-5-nitrophenyl)propan-2-yl)-5-(trifluoromethoxy)phenol (370.0 mg, 0.98 mmol) was dissolved in anhydrous DMF (9.8 mL), and $K_2CO_3$ (406.0 mg, 2.94 mmol) and iodoethane (158.0 mL, 1.97 mmol) were added. The reaction mixture was stirred at 40° C. for 15 hours, $H_2O$ was added, and extracted with EtOAc. The organic extract was washed with brine, dried over anhydrous $Na_2SO_4$ and concentrated under reduced pressure. The residue was purified by flash column chromatography (silica gel, n-Hex:EtOAc=9:1) to obtain 1-chloro-3-(2-(3-ethoxy-5-(trifluoromethoxy)phenyl)propan-2-yl)-5-nitrobenzene (386.0 mg, 97%) as a colorless oil.

$^1$H-NMR (400 MHz, $CDCl_3$): δ 8.07 (s, 1H), 8.00 (s, 1H), 7.48 (s, 1H), 6.60-6.63 (m, 3H), 3.98 (q, 2H, J=7.0 Hz), 1.69 (s, 6H), 1.40 (t, 3H, J=7.0 Hz)

(g) Synthesis of 3-chloro-5-(2-(3-ethoxy-5-(trifluoromethoxy)phenyl)propan-2-yl)aniline 1-Chloro-3-(2-(3-ethoxy-5-(trifluoromethoxy)phenyl)propan-2-yl)-5-nitrobenzene (380.0 mg, 0.94 mmol) was dissolved in a mixture of $MeOH/H_2O$ (10.0 mL, 9/1 v/v), and Zn (616.0 mg, 9.43 mmol) and $NH_4Cl$ (504.0 mg, 9.43 mmol) were added at room temperature. The reaction mixture was ultrasonificated at 40° C. for 40 minutes, cooled to room temperature, filtered through Celite, and concentrated under reduced pressure. The residue was purified by flash column chromatography (amine silica gel, n-Hex:EtOAc=1:1) to obtain 3-chloro-5-(2-(3-ethoxy-5-(trifluoromethoxy)phenyl)propan-2-yl)aniline (350.0 mg, 98%) as a white solid.

LC/MS ESI (+): 374 (M+1)

(h) Synthesis of N-(3-chloro-5-(2-(3-ethoxy-5-(trifluoromethoxy)phenyl)propan-2-yl)phenyl)-5-(2-(methylsulfonyl)propan-2-yl)benzo[b]thiophene-2-carboxamide 5-(2-(Methylsulfonyl)propan-2-yl)benzo[b]thiophene-2-carboxylic acid (38.8 mg, 0.13 mmol), 3-chloro-5-(2-(3-ethoxy-5-(trifluoromethoxy)phenyl)propan-2-yl)aniline (48.6 mg, 0.13 mmol) and HATU (53.0 mg, 0.14 mmol) were dissolved in anhydrous DMF (1.3 mL) and DIPEA (44.0 μL, 0.24 mmol) was added. The reaction mixture was stirred at 40° C. for 3 hours, $H_2O$ was added, and extracted with $CH_2Cl_2$. The organic extract was washed with brine, dried over anhydrous $Na_2SO_4$ and concentrated under reduced pressure. The residue was purified by reversed-phase column chromatography (C18-silica gel, 0.1% formic acid in $CH_3CN$:0.1% formic acid in $H_2O$) to obtain N-(3-chloro-5-(2-(3-ethoxy-5-(trifluoromethoxy)phenyl)propan-2-yl)phenyl)-5-(2-(methylsulfonyl)propan-2-yl)benzo[b]thiophene-2-carboxamide (35.0 mg, 41%) as a white solid.

LC/MS ESI (+): 654 (M+1)

$^1$H-NMR (400 MHz, DMSO-$d_6$): δ 10.65 (s, 1H), 8.34 (s, 1H), 8.20 (s, 1H), 8.09 (d, 1H, J=8.8 Hz), 7.88 (s, 1H), 7.74 (d, 1H, J=8.8 Hz), 7.52 (s, 1H), 7.04 (s, 1H), 6.77 (s, 2H), 6.72 (s, 1H), 4.01 (q, 2H, J=6.9 Hz), 2.73 (s, 3H), 1.84 (s, 6H), 1.64 (s, 6H), 1.29 (t, 3H, J=6.9 Hz)

Compounds from Examples 2 to 16 were synthesized through the synthesis route of Example 1, and data of these compounds are listed as follows.

TABLE 2

| Ex. | Compound | Analysis data |
|---|---|---|
| 2 | N-(3-chloro-5-(2-(3-propoxy-5-(trifluoromethoxy)phenyl)propan-2-yl)phenyl)-5-(2-(methylsulfonyl)propan-2-yl)benzo[b]thiophene-2-carboxamide | LC/MS ESI (+): 668 (M + 1)<br>$^1$H-NMR (400 MHz, DMSO-$d_6$): δ 10.65 (s, 1H), 8.34 (s, 1H), 8.19 (s, 1H), 8.09 (d, 1H, J = 8.8 Hz), 7.88 (s, 1H), 7.74 (d, 1H, J = 8.8 Hz), 7.53 (s, 1H), 7.04 (s, 1H), 6.78 (s, 2H), 6.72 (s, 1H), 3.93 (t, 2H, J = 6.4 Hz), 2.73 (s, 3H), 1.85 (s, 6H), 1.67-1.73 (m, 2H) 1.64 (s, 6H), 0.96 (t, 3H, J = 8.8 Hz) |
| 3 | N-(3-(2-(3-methoxy-5-(trifluoromethoxy)phenyl)propan-2-yl)phenyl)-5-(2-(methylsulfonyl)propan-2-yl)benzo[b]thiophene-2-carboxamide | LC/MS ESI (+): 606 (M + 1)<br>$^1$H-NMR (400 MHz, DMSO-$d_6$): δ 10.50 (s, 1H), 8.35 (s, 1H), 8.19 (s, 1H), 8.09 (d, 1H, J = 8.8 Hz), 7.72 (t, 2H, J = 9.6 Hz), 7.63 (s, 1H), 7.31 (t, 1H, J = 8.0 Hz), 7.01 (d, 1H, J = 8.0 Hz), 6.78 (d, 2H, J = 6.4 Hz), 6.70 (s, 1H), 3.75 (s, 3H), 2.73 (s, 3H), 1.85 (s, 6H), 1.65 (s, 6H) |

TABLE 2-continued

| Ex. | Compound | Analysis data |
|---|---|---|
| 4 | N-(3-bromo-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide | LC/MS ESI (+): 770 (M + 1)<br>$^1$H-NMR (400 MHz, DMSO-$d_6$): δ 10.64 (s, 1H), 8.34 (s, 1H), 8.21 (s, 1H), 8.10 (d, 1H, J = 8.8 Hz), 8.04 (s, 1H), 7.75 (d, 1H, J = 8.8 Hz), 7.59 (s, 1H), 7.27 (s, 1H), 7.23 (s, 1H), 7.19 (s, 1H), 7.13 (s, 1H), 6.81 (t, 1H, J = 51.9 Hz), 2.73 (s, 3H), 1.85 (s, 6H), 1.68 (s, 6H) |
| 5 | N-(3-chloro-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide | LC/MS ESI (−): 724 (M − 1)<br>$^1$H-NMR (400 MHz, DMSO-$d_6$): δ 10.66 (s, 1H), 8.35 (s, 1H), 8.21 (s, 1H), 8.11 (d, 1H, J = 8.4 Hz), 7.92 (t, 1H, J = 1.6 Hz), 7.75 (dd, 1H, J = 8.8, 2.0 Hz), 7.56 (s, 1H), 7.28 (s, 1H), 7.24 (s, 1H), 7.14 (s, 1H), 7.08 (s, 1H), 6.81 (tt, 1H, J = 51.6, 3.2 Hz), 2.74 (s, 3H), 1.86 (s, 6H), 1.69 (s, 6H) |
| 6 | N-(3-methoxy-5-(2-(3-methoxy-5-(trifluoromethoxy)phenyl)propan-2-yl)phenyl)-5-(2-(methylsulfonyl)propan-2-yl)benzo[b]thiophene-2-carboxamide | LC/MS ESI (+): 636 (M + 1)<br>$^1$H-NMR (400 MHz, DMSO-$d_6$): δ 10.48 (s, 1H), 8.34 (s, 1H), 8.18 (s, 1H), 8.09 (d, 1H, J = 8.8 Hz), 7.73 (d, 1H, J = 8.8 Hz), 7.41 (s, 1H), 7.19 (s, 1H), 6.79 (d, 2H, J = 8.8 Hz), 6.71 (s, 1H), 6.56 (s, 1H), 3.75 (s, 3H), 3.73 (s, 3H) 2.73 (s, 3H), 1.84 (s, 6H), 1.62 (s, 6H) |
| 7 | N-(3-chloro-5-(2-(3-methoxy-5-(trifluoromethoxy)phenyl)propan-2-yl)phenyl)-5-(2-(methylsulfonyl)propan-2-yl)benzo[b]thiophene-2-carboxamide | LC/MS ESI (+): 640 (M + 1)<br>$^1$H-NMR (400 MHz, DMSO-$d_6$): δ 10.66 (s, 1H), 8.34 (s, 1H), 8.19 (s, 1H), 8.09 (d, 1H, J = 8.8 Hz), 7.88 (s, 1H), 7.74 (d, 1H, J = 8.8 Hz), 7.52 (s, 1H), 7.04 (s, 1H), 6.81 (s, 2H), 6.73 (s, 1H), 3.76 (s, 3H), 2.73 (s, 3H) 1.85 (s, 6H), 1.64 (s, 6H) |
| 8 | N-(3-chloro-5-(2-(3-(2-morpholinoethoxy)-5-(trifluoromethoxy)phenyl)propan-2-yl)phenyl)-5-(2-(methylsulfonyl)propan-2-yl)benzo[b]thiophene-2-carboxamide | LC/MS ESI (+): 739 (M + 1)<br>$^1$H-NMR (400 MHz, DMSO-$d_6$): δ 10.65 (s, 1H), 8.34 (s, 1H), 8.20 (s, 1H), 8.10 (d, 1H, J = 8.7 Hz), 7.89 (s, 1H), 7.74 (d, 1H, J = 8.7 Hz), 7.54 (s, 1H), 7.05 (s, 1H), 6.83 (s, 1H), 6.79 (s, 1H), 6.74 (s, 1H), 4.07-4.10 (m, 2H), 3.54-3.55 (m, 4H), 2.73 (s, 3H), 2.43-2.64 (m, 6H), 1.85 (s, 6H), 1.64 (s, 6H) |
| 9 | N-(3-bromo-5-(2-(3-isopropoxy-5-(trifluoromethoxy)phenyl)propan-2-yl)phenyl)-5-(2-(methylsulfonyl)propan-2-yl)benzo[b]thiophene-2-carboxamide | LC/MS ESI (+): 712 (M + 1)<br>$^1$H-NMR (400 MHz, DMSO-$d_6$): δ 10.61 (s, 1H), 8.34 (s, 1H), 8.20 (s, 1H), 8.09 (d, 1H, J = 8.7 Hz), 8.03 (s, 1H), 7.74 (d, 1H, J = 8.6 Hz), 7.59 (s, 1H), 7.17 (s, 1H), 6.77 (s, 1H), 6.73 (s, 1H), 6.71 (s, 1H), 4.65 (m, 1H), 2.73 (s, 3H), 1.85 (s, 6H), 1.64 (s, 6H), 1.24 (d, 6H, J = 6.0 Hz) |
| 10 | N-(3-(2-(3-(but-2-yn-1-yloxy)-5-(trifluoromethoxy)phenyl)propan-2-yl)-5-chlorophenyl)-5-(2-(methylsulfonyl)propan-2-yl)benzo[b]thiophene-2-carboxamide | LC/MS ESI (−): 676 (M − 1)<br>$^1$H-NMR (400 MHz, DMSO-$d_6$): δ 10.66 (s, 1H), 8.36 (s, 1H), 8.21 (s, 1H), 8.11 (d, 1H, J = 8.4 Hz), 7.91 (t, 1H, J = 2.0 Hz), 7.75 (dd, 1H, J = 8.8, 2.0 Hz), 7.55 (s, 1H), 7.06 (s, 1H), 6.85 (s, 1H), 6.84 (s, 1H), 6.80 (s, 1H), 4.78 (s, 2H), 2.75 (s, 3H), 1.86 (s, 6H), 1.80 (s, 3H), 1.66 (s, 6H) |
| 11 | N-(3-chloro-5-(2-(3-isobutoxy-5-(trifluoromethoxy)phenyl)propan-2-yl)phenyl)-5-(2-(methylsulfonyl)propan-2-yl)benzo[b]thiophene-2-carboxamide | LC/MS ESI (−): 680 (M − 1)<br>$^1$H-NMR (400 MHz, DMSO-$d_6$): δ 10.66 (s, 1H), 8.35 (s, 1H), 8.21 (s, 1H), 8.11 (d, 1H, J = 8.8 Hz), 7.90 (s, 1H), 7.74 (dd, 1H, J = 8.8, 2.0 Hz), 7.54 (s, 1H), 7.06 (s, 1H), 6.82 (s, 1H), 6.80 (s, 1H), 6.73 (s, 1H), 3.76 (d, 2H, J = 6.4 Hz), 2.74 (s, 3H), 1.99 (m, 1H), 1.86 (s, 6H), 1.66 (s, 6H), 0.97 (d, 6H, J = 6.8 Hz) |
| 12 | N-(3-chloro-5-(2-(3-(2,2,2-trifluoroethoxy)-5-(trifluoromethoxy)phenyl)propan-2-yl)phenyl)-5-(2-(methylsulfonyl)propan-2-yl)benzo[b]thiophene-2-carboxamide | LC/MS ESI (−): 706 (M − 1)<br>$^1$H-NMR (400 MHz, DMSO-$d_6$): δ 10.66 (s, 1H), 8.35 (s, 1H), 8.21 (s, 1H), 8.11 (d, 1H, J = 8.8 Hz), 7.90 (s, 1H), 7.75 (dd, 1H, J = 8.8, 2.0 Hz), 7.55 (s, 1H), 7.06 (s, 1H), 7.00 (s, 1H), 6.98 (s, 1H), 6.85 (s, 1H), 4.82-4.88 (m, 2H), 2.75 (s, 3H), 1.86 (s, 6H), 1.67 (s, 6H) |
| 13 | N-(3-chloro-5-(2-(3-(2,2-difluoroethoxy)-5-(trifluoromethoxy)phenyl)propan-2-yl)phenyl)-5-(2-(methylsulfonyl)propan-2-yl)benzo[b]thiophene-2-carboxamide | LC/MS ESI (−): 688 (M − 1)<br>$^1$H-NMR (400 MHz, DMSO-$d_6$): δ 10.65 (s, 1H), 8.35 (s, 1H), 8.21 (s, 1H), 8.11 (d, 1H, J = 8.8 Hz), 7.90 (s, 1H), 7.75 (dd, 1H, J = 8.8, 1.6 Hz), 7.55 (s, 1H), 7.06 (s, 1H), 6.94 (s, 1H), 6.91 (s, 1H), 6.81 (s, 1H), 6.38 (tt, 1H, J = 54.4, 3.6 Hz), 4.38 (td, 2H, J = 14.4, 3.6 Hz), 2.74 (s, 3H), 1.86 (s, 6H), 1.67 (s, 6H) |

TABLE 2-continued

| Ex. | Compound | Analysis data |
|---|---|---|
| 14 | N-(3-(2-(3-(allyloxy)-5-(trifluoromethoxy)phenyl)propan-2-yl)-5-chlorophenyl)-5-(2-(methylsulfonyl)propan-2-yl)benzo[b]thiophene-2-carboxamide | LC/MS ESI (−): 664 (M − 1)<br>$^1$H-NMR (400 MHz, DMSO-d$_6$): δ 10.65 (s, 1H), 8.35 (s, 1H), 8.21 (s, 1H), 8.11 (d, 1H, J = 8.4 Hz), 7.90 (s, 1H), 7.75 (d, 1H, J = 8.8 Hz), 7.54 (s, 1H), 7.05 (s, 1H), 6.84 (s, 1H), 6.83 (s, 1H), 6.76 (s, 1H), 6.00 (m, 1H), 5.37 (d, 1H, J = 18.0 Hz), 5.27 (d, 1H, J = 9.6 Hz), 4.60 (d, 2H, J = 5.2 Hz), 2.74 (s, 3H), 1.84 (s, 6H), 1.66 (s, 6H) |
| 15 | N-(3-chloro-5-(2-(3-cyclopropoxy-5-(trifluoromethoxy)phenyl)propan-2-yl)phenyl)-5-(2-(methylsulfonyl)propan-2-yl)benzo[b]thiophene-2-carboxamide | LC/MS ESI (−): 664 (M − 1)<br>$^1$H-NMR (400 MHz, DMSO-d$_6$): δ 10.65 (s, 1H), 8.35 (s, 1H), 8.21 (s, 1H), 8.11 (d, 1H, J = 8.8 Hz), 7.91 (s, 1H), 7.75 (d, 1H, J = 8.8 Hz), 7.55 (s, 1H), 7.07 (s, 1H), 6.95 (s, 1H), 6.87 (s, 1H), 6.79 (s, 1H), 3.89 (s, 1H), 2.74 (s, 3H), 1.86 (s, 6H), 1.66 (s, 6H), 0.65-0.79 (m, 4H) |
| 16 | N-(3-chloro-5-(2-(3-isopropoxy-5-(trifluoromethoxy)phenyl)propan-2-yl)phenyl)-5-((methylsulfonyl)methyl)benzo[b]thiophene-2-carboxamide | LC/MS ESI (+): 640 (M + 1)<br>$^1$H-NMR (400 MHz, DMSO-d$_6$): δ 10.61 (s, 1H), 8.35 (s, 1H), 8.10 (d, 1H, J = 8.4 Hz), 8.03 (s, 1H), 7.91 (m, 1H), 7.51-7.54 (m, 2H), 7.05 (s, 1H), 6.77 (s, 1H), 6.73 (m, 1H), 6.72 (s, 1H), 4.60-4.66 (m, 3H), 2.93 (s, 3H), 1.64 (s, 6H), 1.24 (d, 6H, J = 6.0 Hz) |

Example 17) Synthesis of N-(3-chloro-5-(2-(4-methoxyphenyl)propan-2-yl)phenyl)-5-(2-(methylsulfonyl)propan-2-yl)benzo[b]thiophene-2-carboxamide (a) Synthesis of 1-chloro-3-(2-(4-methoxyphenyl)propan-2-yl)-5-nitrobenzene 1-(2-Bromopropan-2-yl)-3-chloro-5-nitrobenzene (30.0 mg, 0.11 mmol) and anisole (0.1 mL, 1.07 mmol) were dissolved in 1,2-dichloroethane (1.1 mL) and AlCl$_3$ (44.0 mg, 0.33 mmol) was added. The reaction mixture was stirred at room temperature for 12 hours, H$_2$O was added, and extracted with CH$_2$Cl$_2$. The organic extract was washed with brine, dried over anhydrous Na$_2$SO$_4$ and concentrated under reduced pressure. The residue was purified by flash column chromatography (silica gel, n-Hex:EtOAc=9:1) to obtain 1-chloro-3-(2-(4-methoxyphenyl)propan-2-yl)-5-nitrobenzene (40.0 mg, 90%) as a yellow solid.

$^1$H-NMR (400 MHz, CDCl$_3$): δ 8.03 (s, 1H), 8.01 (s, 1H), 7.49 (s, 1H), 7.11 (d, 2H, J=8.4 Hz), 6.84 (d, 2H, J=8.6 Hz), 3.81 (s, 3H), 1.70 (s, 6H)

(b) Synthesis of 3-chloro-5-(2-(4-methoxyphenyl)propan-2-yl)aniline

The synthesis procedure of Example 1-g was repeated except for using 1-chloro-3-(2-(4-methoxyphenyl)propan-2-yl)-5-nitrobenzene (84.2 mg, 0.24 mmol) as a starting material to obtain 3-chloro-5-(2-(4-methoxyphenyl)propan-2-yl)aniline (20.0 mg, 56%).

LC/MS ESI (+): 276 (M+1)

$^1$H-NMR (400 MHz, CDCl$_3$): δ 7.14 (d, 2H, J=8.4 Hz), 6.81 (d, 2H, J=8.6 Hz), 6.64 (s, 1H), 6.49 (s, 1H), 6.36 (s, 1H), 3.79 (s, 3H), 3.62 (s, 2H), 1.59 (s, 6H)

(c) Synthesis of N-(3-chloro-5-(2-(4-methoxyphenyl)propan-2-yl)phenyl)-5-(2-(methylsulfonyl)propan-2-yl)benzo[b]thiophene-2-carboxamide The synthesis procedure of Example 1-h was repeated except for using 3-chloro-5-(2-(4-methoxyphenyl)propan-2-yl)aniline (81.0 mg, 0.27 mmol) as a starting material to obtain N-(3-chloro-5-(2-(4-methoxyphenyl)propan-2-yl)phenyl)-5-(2-(methylsulfonyl)propan-2-yl)benzo[b]thiophene-2-carboxamide (40.0 mg, 27%).

LC/MS ESI (+): 556 (M+1)

$^1$H-NMR (400 MHz, DMSO-d$_6$): δ 10.64 (s, 1H), 8.36 (s, 1H), 8.20 (s, 1H), 8.10 (d, 1H, J=8.4 Hz), 7.87 (s, 1H), 7.75 (dd, 1H, J=8.4, 1.6 Hz), 7.54 (s, 1H), 7.17 (d, 2H, J=8.8 Hz), 7.00 (s, 1H), 6.88 (d, 2H, J=8.8 Hz), 3.74 (s, 3H), 2.74 (s, 3H), 1.86 (s, 6H), 1.64 (s, 6H)

Compounds from Example 18 to Example 36 were synthesized through the synthesis route of Example 17, and data of these compounds are listed as follows.

TABLE 3

| Ex. | Compound | Analysis data |
|---|---|---|
| 18 | N-(3-chloro-5-(2-(4-fluorophenyl)propan-2-yl)phenyl)-5-(2-(methylsulfonyl)propan-2-yl)benzo[b]thiophene-2-carboxamide | LC/MS ESI (+): 544 (M + 1)<br>$^1$H-NMR (400 MHz, DMSO-d$_6$): δ 10.64 (brs, 1H), 8.34 (s, 1H), 8.20 (s, 1H), 8.08 (d, 1H, J = 8.7 Hz), 7.87 (s, 1H), 7.73 (d, 1H, J = 8.7 Hz), 7.52 (s, 1H), 7.27-7.30 (m, 2H), 7.11-7.15 (m, 2H), 7.02 (s, 1H), 2.73 (s, 3H), 1.85 (s, 6H), 1.65 (s, 6H) |

TABLE 3-continued

| Ex. | Compound | Analysis data |
|---|---|---|
| 19 | N-(3-chloro-5-(2-(4-fluorophenyl)propan-2-yl)phenyl)-6-fluoro-5-(2-(methylsulfonyl)propan-2-yl)benzo[b]thiophene-2-carboxamide | LC/MS ESI (+): 562 (M + 1)<br>$^1$H-NMR (400 MHz, DMSO-d$_6$): δ 10.66 (s, 1H), 8.32 (s, 1H), 8.22 (d, 1H, J = 7.7 Hz), 8.02 (d, 1H, J = 13.1 Hz), 7.86 (s, 1H), 7.49 (s, 1H), 7.28 (dd, 2H, J = 8.7, 5.5 Hz), 7.13 (t, 2H, J = 8.8 Hz), 7.03 (s, 1H), 2.88 (s, 3H), 1.92 (s, 6H), 1.64 (s, 6H) |
| 20 | N-(3-bromo-5-(2-(4-fluorophenyl)propan-2-yl)phenyl)-5-(2-(methylsulfonyl)propan-2-yl)benzo[b]thiophene-2-carboxamide | LC/MS ESI (+): 588 (M + 1)<br>$^1$H-NMR (400 MHz, DMSO-d$_6$): δ 10.61 (s, 1H), 8.34 (s, 1H), 8.19 (s, 1H), 8.10 (d, 1H, J = 8.8 Hz), 8.00 (s, 1H), 7.74 (d, 1H, J = 8.8 Hz), 7.56 (s, 1H), 7.26-7.30 (m, 2H), 7.11-7.15 (m, 3H), 2.73 (s, 3H), 1.84 (s, 6H), 1.64 (s, 6H) |
| 21 | N-(3-chloro-5-(2-(4-chlorophenyl)propan-2-yl)phenyl)-5-((methylsulfonyl)methyl)benzo[b]thiophene-2-carboxamide | LC/MS ESI (+): 532 (M + 1)<br>$^1$H-NMR (400 MHz, DMSO-d$_6$): δ 10.60 (s, 1H), 8.34 (s, 1H), 8.09 (d, 1H, J = 8.4 Hz), 8.02 (s, 1H), 7.89 (m, 1H), 7.50-7.53 (m, 2H), 7.37 (d, 2H, J = 8.6 Hz), 7.27 (d, 2H, J = 8.6 Hz), 7.03 (m, 1H), 4.64 (s, 2H), 2.93 (s, 3H), 1.65 (s, 6H) |
| 22 | N-(3-chloro-5-(2-(4-chlorophenyl)propan-2-yl)phenyl)-5-(2-(methylsulfonyl)propan-2-yl)benzo[b]thiophene-2-carboxamide | LC/MS ESI (+): 560 (M + 1)<br>$^1$H-NMR (400 MHz, DMSO-d$_6$): δ 10.63 (s, 1H), 8.33 (s, 1H), 8.19 (m, 1H), 8.09 (d, 1H, J = 8.8 Hz), 7.88 (m, 1H), 7.74 (dd, 1H, J = 8.5, 1.6 Hz), 7.50 (m, 1H), 7.37 (d, 2H, J = 8.5 Hz), 7.27 (d, 2H, J = 8.7 Hz), 7.03 (m, 1H), 2.73 (s, 3H), 1.85 (s, 6H), 1.64 (s, 6H) |
| 23 | 6-chloro-N-(3-chloro-5-(2-(4-chlorophenyl)propan-2-yl)phenyl)-5-(2-(methylsulfonyl)propan-2-yl)benzo[b]thiophene-2-carboxamide | LC/MS ESI (+): 594 (M + 1)<br>$^1$H-NMR (400 MHz, DMSO-d$_6$): δ 10.67 (s, 1H), 8.36 (s, 1H), 8.31 (s, 1H), 8.28 (s, 1H), 7.87 (m, 1H), 7.47 (m, 1H), 7.37 (d, 2H, J = 8.7 Hz), 7.27 (d, 2H, J = 8.7 Hz), 7.04 (m, 1H), 2.89 (s, 3H), 2.05 (s, 6H), 1.64 (s, 6H) |
| 24 | N-(3-chloro-5-(2-(4-chlorophenyl)propan-2-yl)phenyl)-5-(((trifluoromethyl)sulfonyl)methyl)benzo[b]thiophene-2-carboxamide | LC/MS ESI (+): 586 (M + 1)<br>$^1$H-NMR (400 MHz, DMSO-d$_6$): δ 10.62 (s, 1H), 8.36 (s, 1H), 8.16 (m, 1H), 8.12 (m, 1H), 7.89 (m, 1H), 7.56 (m, 1H), 7.50 (m, 1H), 7.37 (d, 2H, J = 8.7 Hz), 7.27 (d, 2H, J = 8.7 Hz), 7.03 (m, 1H), 5.42 (s, 2H), 1.64 (s, 6H) |
| 25 | N-(3-chloro-5-(2-(4-chlorophenyl)propan-2-yl)phenyl)-5-(fluoro(methylsulfonyl)methyl)benzo[b]thiophene-2-carboxamide | LC/MS ESI (+): 550 (M + 1)<br>$^1$H-NMR (400 MHz, DMSO-d$_6$): δ 10.67 (s, 1H), 8.39 (m, 1H), 8.21 (d, 1H, J = 8.8 Hz), 8.13 (s, 1H), 7.89 (m, 1H), 7.59 (d, 1H, J = 8.8 Hz), 7.49 (m, 1H), 7.37 (d, 2H, J = 8.7 Hz), 7.27 (d, 2H, J = 8.7 Hz), 7.03 (m, 1H), 6.94 (d, 1H, J = 45.0 Hz), 3.20 (s, 3H), 1.65 (s, 6H) |
| 26 | N-(3-chloro-5-(2-(4-chlorophenyl)propan-2-yl)phenyl)-5-(2-(methylsulfonyl)propan-2-yl)thieno[2,3-c]pyridine-2-carboxamide | LC/MS ESI (+): 561 (M + 1)<br>$^1$H-NMR (400 MHz, DMSO-d$_6$): δ 10.83 (s, 1H), 9.39 (s, 1H), 8.38 (s, 1H), 8.26 (s, 1H), 7.89 (s, 1H), 7.51 (s, 1H), 7.38 (d, 2H, J = 8.4 Hz), 7.28 (d, 2H, J = 8.4 Hz), 7.08 (s, 1H), 2.87 (s, 3H), 1.88 (s, 6H), 1.66 (s, 6H) |
| 27 | N-(3-chloro-5-(2-(5-chlorothiophen-2-yl)propan-2-yl)phenyl)-5-(2-(methylsulfonyl)propan-2-yl)benzo[b]thiophene-2-carboxamide | LC/MS ESI (+): 566 (M + 1)<br>$^1$H-NMR (400 MHz, DMSO-d$_6$): δ 10.68 (s, 1H), 8.35 (s, 1H), 8.21 (s, 1H), 8.10 (d, 1H, J = 8.8 Hz), 7.90 (m, 1H), 7.74 (dd, 1H, J = 8.8, 1.9 Hz), 7.63 (m, 1H), 7.13 (m, 1H), 6.99 (d, 1H, J = 3.9 Hz), 6.86 (d, 1H, J = 3.9 Hz), 2.74 (s, 3H), 1.85 (s, 6H), 1.71 (s, 6H) |
| 28 | N-(3-chloro-5-(2-(5-isopropylthiophen-2-yl)propan-2-yl)phenyl)-5-(2-(methylsulfonyl)propan-2-yl)benzo[b]thiophene-2-carboxamide | LC/MS ESI (+): 574 (M + 1)<br>$^1$H-NMR (400 MHz, DMSO-d$_6$): δ 10.67 (s, 1H), 8.37 (s, 1H), 8.21 (s, 1H), 8.10 (d, 1H, J = 8.5 Hz), 7.88 (s, 1H), 7.75 (d, 1H, J = 8.7 Hz), 7.67 (s, 1H), 7.09 (s, 1H), 6.75 (d, 1H J = 3.4 Hz), 6.67 (d, 1H J = 3.3 Hz), 3.08 (m, 1H), 2.73 (s, 3H), 1.85 (s, 6H), 1.70 (s, 6H), 1.22 (d, 6H, J = 6.8 Hz) |
| 29 | N-(3-chloro-5-(2-(5-methoxythiophen-2-yl)propan-2-yl)phenyl)-5-(2-(methylsulfonyl)propan-2-yl)benzo[b]thiophene-2-carboxamide | LC/MS ESI (+): 562 (M + 1)<br>$^1$H-NMR (400 MHz, DMSO-d$_6$): δ 10.65 (s, 1H), 8.36 (s, 1H), 8.21 (s, 1H), 8.10 (d, 1H, J = 8.6 Hz), 7.87 (s, 1H), 7.76 (d, 1H, J = 8.7 Hz), 7.64 (s, 1H), 7.08 (s, 1H), 6.58 (d, 1H J = 3.8 Hz), 6.10 (d, 1H J = 3.8 Hz), 3.79 (s, 3H), 2.73 (s, 3H), 1.85 (s, 6H), 1.66 (d, 6H) |

TABLE 3-continued

| Ex. | Compound | Analysis data |
|---|---|---|
| 30 | N-(3-chloro-5-(2-(2-methoxythiophen-3-yl)propan-2-yl)phenyl)-5-(2-(methylsulfonyl)propan-2-yl)benzo[b]thiophene-2-carboxamide | LC/MS ESI (+): 562 (M + 1)<br>$^1$H-NMR (400 MHz, DMSO-d$_6$): δ 10.62 (s, 1H), 8.36 (s, 1H), 8.20 (s, 1H), 8.09 (d, 1H, J = 8.6 Hz), 7.84 (t, 1H, J = 1.6 Hz), 7.75 (d, 1H, J = 1.6 Hz), 7.55 (s, 1H), 6.97 (d, 1H J = 1.6 Hz), 6.80 (d, 2H J = 2.0 Hz), 3.63 (s, 3H), 2.73 (s, 3H), 1.85 (s, 6H), 1.62 (s, 6H) |
| 31 | N-(3-chloro-5-(2-(1-methyl-1H-pyrrol-2-yl)propan-2-yl)phenyl)-5-(2-(methylsulfonyl)propan-2-yl)benzo[b]thiophene-2-carboxamide | LC/MS ESI (+): 529 (M + 1)<br>$^1$H-NMR (400 MHz, DMSO-d$_6$): δ 10.69 (s, 1H), 8.35 (s, 1H), 8.19 (s, 1H), 8.09 (d, 1H, J = 8.4 Hz), 7.88 (s, 1H), 7.74 (s, 1H, J = 8.8 Hz), 7.50 (s, 1H), 6.80 (s, 1H), 6.62 (d, 1H, J = 1.6 Hz), 6.10 (m, 1H), 5.94 (t, 1H, J = 1.6 Hz), 3.09 (s, 3H), 2.73 (s, 3H), 1.85 (s, 6H), 1.61 (s, 6H) |
| 32 | N-(3-chloro-5-(2-(4-methylthiophen-2-yl)propan-2-yl)phenyl)-5-(2-(methylsulfonyl)propan-2-yl)benzo[b]thiophene-2-carboxamide | LC/MS ESI (+): 546 (M + 1)<br>$^1$H-NMR (400 MHz, DMSO-d$_6$): δ 10.69 (s, 1H), 8.36 (s, 1H), 8.20 (s, 1H), 8.09 (d, 1H, J = 8.8 Hz), 7.88 (s, 1H), 7.74 (dd, 1H, J = 8.4, 1.6 Hz), 7.64 (s, 1H), 7.08 (s, 1H), 6.95 (s, 1H) 6.78 (s, 1H), 2.73 (s, 3H), 2.17 (s, 3H) 1.85 (s, 6H), 1.70 (s, 6H) |
| 33 | N-(3-chloro-5-(2-(4-chlorophenyl)propan-2-yl)phenyl)-5-(1-(methylsulfonyl)cyclopropyl)benzo[b]thiophene-2-carboxamide | LC/MS ESI (+): 558 (M + 1)<br>$^1$H-NMR (400 MHz, DMSO-d$_6$): δ 10.65 (s, 1H), 8.32 (s, 1H), 8.16 (s, 1H), 8.09 (d, 1H, J = 8.4 Hz), 7.87 (m, 1H), 7.66 (dd, 1H, J = 8.2, 1.4 Hz), 7.50 (m, 1H), 7.37 (d, 2H, J = 8.6 Hz), 7.27 (d, 2H, J = 8.6 Hz), 7.03 (m, 1H), 2.89 (s, 3H), 1.68-1.71 (m, 2H), 1.64 (s, 6H), 1.37-1.40 (m, 2H) |
| 34 | N-(3-chloro-5-(2-(4-chlorophenyl)propan-2-yl)phenyl)-5-(4-(methylsulfonyl)tetrahydro-2H-pyran-4-yl)benzo[b]thiophene-2-carboxamide | LC/MS ESI (+): 602 (M + 1)<br>$^1$H-NMR (400 MHz, DMSO-d$_6$): δ 10.65 (s, 1H), 8.33 (s, 1H), 8.25 (s, 1H), 8.15 (d, 1H, J = 8.7 Hz), 7.88 (s, 1H), 7.73 (m, J = 8.5 Hz), 7.50 (s, 1H), 7.37 (d, 2, J = 8.5 Hz), 7.27 (d, 2H, J = 8.5 Hz), 7.04 (s, 1H), 3.91 (d, 2H, J = 10.8 Hz), 3.20 (t, 2H, J = 11.8 Hz), 2.73 (d, 2H, J = 12.7 Hz), 2.65 (s, 3H), 2.33 (t, 2H, J = 12.0 Hz), 1.64 (s, 6H) |
| 35 | N-(3-chloro-5-(2-(4-chlorophenyl)propan-2-yl)phenyl)-6-(2-(methylsulfonyl)propan-2-yl)-1H-indole-2-carboxamide | LC/MS ESI (+): 543 (M + 1)<br>$^1$H-NMR (400 MHz, DMSO-d$_6$): δ 11.85 (s, 1H), 10.34 (s, 1H), 7.95 (m, 1H), 7.68-7.70 (m, 2H), 7.55 (m, 1H), 7.35-7.40 (m, 4H), 7.28 (d, 2H, J = 8.7 Hz), 7.00 (m, 1H), 2.68 (s, 3H), 1.81 (s, 6H), 1.65 (s, 6H) |
| 36 | N-(3-chloro-5-(2-(4-chlorophenyl)propan-2-yl)phenyl)-5-((S-methylsulfonimidoyl)methyl)benzo[b]thiophene-2-carboxamide | LC/MS ESI (+): 531 (M + 1)<br>$^1$H-NMR (400 MHz, DMSO-d$_6$): δ 10.58 (s, 1H), 8.34 (m, 1H), 8.07 (d, 1H, J = 8.4 Hz), 8.04 (m, 1H), 7.89 (m, 1H), 7.55 (dd, 1H, J = 8.4, 1.6 Hz), 7.51 (m, 1H), 7.37 (d, 2H, J = 8.7 Hz), 7.27 (d, 2H, J = 8.7 Hz), 7.03 (m, 1H), 4.47-4.56 (m, 3H), 2.80 (s, 3H), 1.65 (s, 6H) |

Example 37) Synthesis of N-(3-chloro-5-(4-(trifluoromethoxy)phenoxy)phenyl)-5-(2-(methylsulfonyl)propan-2-yl)benzo[b]thiophene-2-carboxamide (a) Synthesis of 1-chloro-3-nitro-5-(4-(trifluoromethoxy)phenoxy)benzene 1-Bromo-3-chloro-5-nitrobenzene (200.0 mg, 0.84 mmol), 4-(trifluoromethoxy)phenol (220.0 mg, 1.69 mmol), CuI (80.6 mg, 0.42 mmol), N,N-dimethylglycine (87.2 mg, 0.42 mmol) and Cs$_2$CO$_3$ (826.9 mg, 2.53 mmol) were dissolved in anhydrous 1,4-dioxane (5.0 mL). The reaction mixture was stirred at 120° C. for 15 hours, cooled to room temperature, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex) to obtain 1-chloro-3-nitro-5-(4-(trifluoromethoxy)phenoxy)benzene (160.0 mg, 61%) as a yellow oil.

$^1$H-NMR (400 MHz, CDCl$_3$): δ 7.95 (s, 1H), 7.65 (s, 1H), 7.26-7.30 (m, 3H), 7.09 (d, 2H, J=8.8 Hz)

(b) Synthesis of 3-chloro-5-(4-(trifluoromethoxy)phenoxy)aniline

The synthesis procedure of Example 1-g was repeated except for using 1-chloro-3-nitro-5-(4-(trifluoromethoxy)phenoxy)benzene (160.0 mg, 0.52 mmol) as a starting material to obtain 3-chloro-5-(4-(trifluoromethoxy)phenoxy)aniline (130.0 mg, 79%) as an off-white oil.

LC/MS ESI (+): 304 (M+1)

$^1$H-NMR (400 MHz, CDCl$_3$): δ 7.31 (d, 2H, J=8.7 Hz), 6.95 (d, 2H, J=8.7 Hz), 6.41 (s, 1H), 6.34 (s, 1H), 6.16 (s, 1H), 3.76 (brs, 2H)

(c) Synthesis of N-(3-chloro-5-(4-(trifluoromethoxy)phenoxy)phenyl)-5-(2-(methylsulfonyl)propan-2-yl)benzo[b]thiophene-2-carboxamide The synthesis procedure of Example 1-h was repeated except for using 3-chloro-5-(4-(trifluoromethoxy)phenoxy)aniline (130.0 mg, 0.42 mmol) and 5-(2-(methylsulfonyl)propan-2-yl)benzo[b]thiophene-2-carboxylic acid (150.0 mg, 0.55 mmol) as starting materials, to obtain N-(3-chloro-5-(4-(trifluoromethoxy)phenoxy)phenyl)-5-(2-(methylsulfonyl)propan-2-yl)benzo[b]thiophene-2-carboxamide (75.0 mg, 47%) as a white solid.

LC/MS ESI (+): 584 (M+1)

$^1$H-NMR (400 MHz, DMSO-d$_6$): δ 10.74 (brs, 1H), 8.34 (s, 1H), 8.21 (s, 1H), 8.09 (d, 1H, J=8.7 Hz), 7.79 (s, 1H), 7.74 (d, 1H, J=8.7 Hz), 7.46 (d, 2H, J=8.7 Hz), 7.40 (t, 1H, J=1.8 Hz), 7.26 (d, 2H, J=8.9 Hz), 6.96 (t, 1H, J=1.8 Hz), 2.73 (s, 3H), 1.85 (s, 6H)

Compounds from Example 38 to Example 61 were synthesized through the synthesis route of Example 37, and data of these compounds are listed as follows.

TABLE 4

| Ex. | Compound | Analysis data |
|---|---|---|
| 38 | N-(3-chloro-5-(4-(trifluoromethyl)phenoxy)phenyl)-5-(2-(methylsulfonyl)propan-2-yl)benzo[b]thiophene-2-carboxamide | LC/MS ESI (+): 568 (M + 1)<br>$^1$H-NMR (400 MHz, DMSO-d$_6$): δ 10.77 (s, 1H), 8.34 (s, 1H), 8.21 (d, 1H, J = 1.5 Hz), 8.10 (d, 1H, J = 8.7 Hz), 7.82 (s, 1H), 7.81 (d, 2H, J = 8.7 Hz), 7.75 (dd, 1H, J = 8.8, 1.8 Hz), 7.47 (m, 1H), 7.30 (d, 2H, J = 8.5 Hz), 7.05 (m, 1H), 2.73 (s, 3H), 1.85 (s, 6H) |
| 39 | N-(3-bromo-5-(4-chlorophenoxy)phenyl)-5-(2-(methylsulfonyl)propan-2-yl)benzo[b]thiophene-2-carboxamide | LC/MS ESI (−): 576 (M − 1)<br>$^1$H-NMR (400 MHz, DMSO-d$_6$): δ 10.69 (s, 1H), 8.34 (s, 1H), 8.21 (s, 1H), 8.10 (d, 1H, J = 8.4 Hz), 7.90 (s, 1H), 7.75 (d, 1H, J = 8.4 Hz), 7.52 (d, 2H, J = 8.8 Hz), 7.42 (s, 1H), 7.18 (d, 2H, J = 8.8 Hz), 7.04 (s, 1H), 2.74 (s, 3H), 1.86 (s, 6H) |
| 40 | N-(3-chloro-5-(4-chlorophenoxy)phenyl)-6-(2-(methylsulfonyl)propan-2-yl)-1H-indole-2-carboxamide | LC/MS ESI (+): 517 (M + 1)<br>$^1$H-NMR (400 MHz, DMSO-d$_6$): δ 11.90 (s, 1H), 10.42 (s, 1H), 7.79 (m, 1H), 7.70 (d, 1H, J = 8.7 Hz), 7.67 (s, 1H), 7.52 (d, 2H, J = 8.9 Hz), 7.45 (m, 1H), 7.40 (m, 1H), 7.36 (dd, 1H, J = 8.7, 1.8 Hz), 7.19 (d, 2H, J = 8.9 Hz), 6.89 (m, 1H), 2.68 (s, 3H), 1.80 (s, 6H) |
| 41 | N-(3-chloro-5-(4-chlorophenoxy)phenyl)-5-((methylsulfonyl)methyl)benzo[b]thiophene-2-carboxamide | LC/MS ESI (+): 506 (M + 1)<br>$^1$H-NMR (400 MHz, DMSO-d$_6$): δ 10.68 (s, 1H), 8.33 (s, 1H), 8.09 (d, 1H, J = 8.3 Hz), 8.03 (s, 1H), 7.76 (m, 1H), 7.54 (s, 1H), 7.44 (d, 2H, J = 8.8 Hz), 7.36 (m, 1H), 7.18 (d, 2H, J = 8.8 Hz), 6.92 (m, 1H), 4.64 (s, 2H), 2.93 (s, 3H) |
| 42 | N-(3-chloro-5-(4-chlorophenoxy)phenyl)-5-(((trifluoromethyl)sulfonyl)methyl)benzo[b]thiophene-2-carboxamide | LC/MS ESI (+): 560 (M + 1)<br>$^1$H-NMR (400 MHz, DMSO-d$_6$): δ 10.70 (s, 1H), 8.35 (s, 1H), 8.15-8.18 (m, 2H), 7.75 (m, 1H), 7.56 (m, 1H), 7.51 (d, 2H, J = 8.9 Hz), 7.35 (m, 1H), 7.18 (d, 2H, J = 8.9 Hz), 6.92 (m, 1H), 5.41 (s, 2H) |
| 43 | N-(3-chloro-5-(4-fluorophenoxy)phenyl)-5-(2-(methylsulfonyl)propan-2-yl)benzo[b]thiophene-2-carboxamide | LC/MS ESI (+): 518 (M + 1)<br>$^1$H-NMR (400 MHz, DMSO-d$_6$): δ 10.72 (brs, 1H), 8.33 (s, 1H), 8.21 (s, 1H), 8.10 (d, 1H, J = 8.8 Hz), 7.74-7.76 (m, 2H), 7.30-7.34 (m, 3H), 7.20-7.23 (m, 2H), 6.86 (s, 1H), 2.74 (s, 3H), 1.85 (s, 6H) |
| 44 | N-(3-chloro-5-(4-chlorophenoxy)phenyl)-6-fluoro-5-(2-(methylsulfonyl)propan-2-yl)benzo[b]thiophene-2-carboxamide | LC/MS ESI (+): 552 (M + 1)<br>$^1$H-NMR (400 MHz, DMSO-d$_6$): δ 10.74 (s, 1H), 8.31 (s, 1H), 8.24 (d, 1H, J = 7.6 Hz), 8.02 (d, 1H, J = 13.1 Hz), 7.75 (s, 1H), 7.51 (d, 2H, J = 8.6 Hz), 7.34 (s, 1H), 7.18 (d, 2H, J = 8.6 Hz), 6.93 (s, 1H), 2.87 (s, 3H), 1.92 (s, 6H) |
| 45 | 6-chloro-N-(3-chloro-5-(4-chlorophenoxy)phenyl)-5-(2-(methylsulfonyl)propan-2-yl)benzo[b]thiophene-2-carboxamide | LC/MS ESI (+): 568 (M + 1)<br>$^1$H-NMR (400 MHz, DMSO-d$_6$): δ 10.74 (s, 1H), 8.38 (s, 1H), 8.31 (s, 1H), 8.28 (s, 1H), 7.75 (m, 1H), 7.51 (d, 2H, J = 8.9 Hz), 7.34 (m, 1H), 7.18 (d, 2H, J = 8.9 Hz), 6.93 (m, 1H), 2.89 (s, 3H), 2.05 (s, 6H) |
| 46 | N-(3-(4-chlorophenoxy)-5-methoxyphenyl)-5-(2-(methylsulfonyl)propan-2-yl)benzo[b]thiophene-2-carboxamide | LC/MS ESI (+): 530 (M + 1)<br>$^1$H-NMR (400 MHz, DMSO-d$_6$): δ 10.53 (brs, 1H), 8.34 (s, 1H), 8.19 (s, 1H), 8.08 (d, 1H, J = 8.7 Hz), 7.73 (d, 1H, J = 8.7 Hz), 7.47 (d, 2H, J = 8.7 Hz), 7.30 (s, 1H), 7.11 (d, 2H, J = 8.9 Hz), 7.04 (s, 1H), 6.44 (s, 1H), 3.77 (s, 3H), 2.73 (s, 3H), 1.85 (s, 6H) |
| 47 | N-(3-chloro-5-(3-chloro-5-fluorophenoxy)phenyl)-5-(2-(methylsulfonyl)propan-2-yl)benzo[b]thiophene-2-carboxamide | LC/MS ESI (+): 552 (M + 1)<br>$^1$H-NMR (400 MHz, DMSO-d$_6$): δ 10.76 (s, 1H), 8.35 (s, 1H), 8.22 (d, 1H, J = 1.6 Hz), 8.10 (d, 1H, J = 8.7 Hz), 7.81 (m, 1H), 7.75 (dd, 1H, J = 8.7, 1.8 Hz), 7.44 (m, 1H), 7.32 (dt, 1H, |

TABLE 4-continued

| Ex. | Compound | Analysis data |
|---|---|---|
| | | J = 8.6, 2.0 Hz), 7.08-7.12 (m, 2H), 7.03 (m, 1H), 2.73 (s, 3H), 1.85 (s, 6H) |
| 48 | N-(3-chloro-5-(3-(trifluoromethoxy)phenoxy)phenyl)-5-(2-(methylsulfonyl)propan-2-yl)benzo[b]thiophene-2-carboxamide | LC/MS ESI (+): 584 (M + 1)<br>$^1$H-NMR (400 MHz, DMSO-$d_6$): δ 10.78 (brs, 1H), 8.34 (s, 1H), 8.22 (s, 1H), 8.10 (d, 1H, J = 8.8 Hz), 7.80 (s, 1H), 7.75 (d, 1H, J = 8.8 Hz), 7.59 (t, 1H, J = 8.0 Hz), 7.44 (s, 1H) 7.15-7.26 (m, 3H), 6.98 (s, 1H), 2.74 (s, 3H), 1.86 (s, 6H) |
| 49 | N-(3-chloro-5-(4-chlorophenoxy)phenyl)-5-(2-(methylsulfonyl)propan-2-yl)benzo[b]thiophene-2-carboxamide | LC/MS ESI (+): 534 (M + 1)<br>$^1$H-NMR (400 MHz, DMSO-$d_6$): δ 10.70 (s, 1H), 8.32 (s, 1H), 8.20 (s, 1H), 8.09 (d, 1H, J = 8.7 Hz), 7.73-7.76 (m, 2H), 7.51 (d, 2H, J = 8.9 Hz), 7.36 (m, 1H), 7.18 (d, 2H, J = 8.9 Hz), 6.91 (m, 1H), 2.73 (s, 3H), 1.85 (s, 6H) |
| 50 | N-(3-chloro-5-(4-chlorophenoxy)phenyl)-5-(2-(methylsulfonyl)propan-2-yl)thieno[2,3-c]pyridine-2-carboxamide | LC/MS ESI (+): 535 (M + 1)<br>$^1$H-NMR (400 MHz, DMSO-$d_6$): δ 10.91 (brs, 1H), 9.38 (s, 1H), 8.36 (s, 1H), 8.27 (s, 1H), 7.76 (s, 1H), 7.52 (d, 2H, J = 8.8 Hz), 7.36 (s, 1H), 7.19 (d, 2H, J = 8.8 Hz), 6.96 (s, 1H), 2.87 (s, 3H), 1.87 (s, 6H) |
| 51 | N-(3-chloro-5-(3-chloro-4-fluorophenoxy)phenyl)-5-(2-(methylsulfonyl)propan-2-yl)benzo[b]thiophene-2-carboxamide | LC/MS ESI (+): 552 (M + 1)<br>$^1$H-NMR (400 MHz, DMSO-$d_6$): δ 10.71 (brs, 1H), 8.34 (s, 1H), 8.21 (d, 1H, J = 1.6 Hz), 8.10 (d, 1H, J = 8.7 Hz), 7.73-7.77 (m, 2H), 7.49-7.54 (m, 2H), 7.34 (m, 1H), 7.20 (m, 1H), 6.93 (m, 1H), 2.73 (s, 3H), 1.85 (s, 6H) |
| 52 | N-(3-chloro-5-(3,4-difluorophenoxy)phenyl)-5-(2-(methylsulfonyl)propan-2-yl)benzo[b]thiophene-2-carboxamide | LC/MS ESI (+): 536 (M + 1)<br>$^1$H-NMR (400 MHz, DMSO-$d_6$): δ 10.70 (s, 1H), 8.34 (s, 1H), 8.21 (s, 1H), 8.10 (d, 1H, J = 8.7 Hz), 7.73-7.77 (m, 2H), 7.55 (m, 1H), 7.42 (m, 1H), 7.36 (m, 1H), 7.04 (m, 1H), 6.93 (m, 1H), 2.73 (s, 3H), 1.85 (s, 6H) |
| 53 | N-(3-chloro-5-(3-fluoro-5-methoxyphenoxy)phenyl)-5-(2-(methylsulfonyl)propan-2-yl)benzo[b]thiophene-2-carboxamide | LC/MS ESI (+): 548 (M + 1)<br>$^1$H-NMR (400 MHz, DMSO-$d_6$): δ 10.75 (s, 1H), 8.35 (s, 1H), 8.21 (s, 1H), 8.10 (d, 1H, J = 8.7 Hz), 7.73-7.78 (m, 2H), 7.40 (s, 1H), 6.96 (s, 1H), 6.73 (m, 1H), 6.57-6.61 (m, 2H), 3.78 (s, 3H), 2.73 (s, 3H), 1.85 (s, 6H) |
| 54 | N-(3-chloro-5-(4-chloro-3-fluorophenoxy)phenyl)-5-(2-(methylsulfonyl)propan-2-yl)benzo[b]thiophene-2-carboxamide | LC/MS ESI (+): 552 (M + 1)<br>$^1$H-NMR (400 MHz, DMSO-$d_6$): δ 10.72 (s, 1H), 8.34 (s, 1H), 8.21 (d, 1H, J = 1.4 Hz), 8.10 (d, 1H, J = 8.7 Hz), 7.79 (m, 1H), 7.75 (dd, 1H, J = 8.8, 1.8 Hz), 7.66 (t, 1H, J = 8.7 Hz), 7.41 (m, 1H), 7.35 (dd, 1H, J = 10.4, 2.7 Hz), 6.99-7.04 (m, 2H), 2.73 (s, 3H), 1.85 (s, 6H) |
| 55 | N-(3-chloro-5-(2-(3-chloro-5-methoxyphenyl)propan-2-yl)phenyl)-5-(2-(methylsulfonyl)propan-2-yl)benzo[b]thiophene-2-carboxamide | LC/MS ESI (+): 564 (M + 1)<br>$^1$H-NMR (400 MHz, DMSO-$d_6$): δ 10.71 (s, 1H), 8.34 (s, 1H), 8.20 (d, 1H, J = 1.6 Hz), 8.09 (d, 1H, J = 8.7 Hz), 7.79 (t, 1H, J = 1.8Hz), 7.74 (dd, 1H, J = 8.7, 1.8 Hz), 7.39 (t, 1H, J = 1.9Hz), 6.96 (t, 1H, J = 1.9Hz), 6.91 (t, 1H, J = 1.9Hz), 6.77 (t, 1H, J = 1.9Hz), 6.70 (t, 1H, J = 2.1Hz), 3.79 (s, 3H), 2.72 (s, 3H) 1.84 (s, 6H) |
| 56 | N-(3-chloro-5-(4-chlorophenoxy)phenyl)-5-(4-(methylsulfonyl)tetrahydro-2H-pyran-4-yl)benzo[b]thiophene-2-carboxamide | LC/MS ESI (+): 576 (M + 1)<br>$^1$H-NMR (400 MHz, DMSO-$d_6$): δ 10.73 (s, 1H), 8.32 (s, 1H), 8.27 (s, 1H), 8.16 (d, 1H, J = 8.7 Hz), 7.76 (s, 1H), 7.73 (d, 1H, J = 9.1 Hz), 7.51 (d, 2H, J = 8.8 Hz), 7.36 (s, 1H), 7.18 (d, 2H, J = 8.8 Hz), 6.93 (s, 1H), 3.91 (d, 2H, J = 9.7 Hz), 3.20 (t, 2H, J = 11.7 Hz), 2.74 (d, 2H, J = 13.3 Hz), 2.65 (s, 3H), 2.33 (t, 2H, J = 12.3 Hz) |
| 57 | N-(3-chloro-5-(4-chlorophenoxy)phenyl)-5-(2-((2-methoxyethyl)sulfonyl)propan-2-yl)benzo[b]thiophene-2-carboxamide | LC/MS ESI (+): 578 (M + 1)<br>$^1$H-NMR (400 MHz, DMSO-$d_6$): δ 10.72 (s, 1H), 8.33 (s, 1H), 8.22 (s, 1H), 8.11 (d, 1H, J = 8.6 Hz), 7.74-7.77 (m, 2H), 7.52 (d, 2H, J = 8.9 Hz), 7.37 (s, 1H), 7.19 (d, 2H, J = 8.9 Hz), 6.93 (s, 1H), 3.49 (t, 2H, J = 6.3 Hz), 3.11-3.14 (m, 5H), 1.85 (s, 6H) |
| 58 | N-(3-chloro-5-(4-chlorophenoxy)phenyl)-6-(2-(methylsulfonyl)propan-2-yl)benzo[b]thiophene-2-carboxamide | LC/MS ESI (+): 534 (M + 1)<br>$^1$H-NMR (400 MHz, DMSO-$d_6$): δ 10.69 (s, 1H), 8.30-8.33 (s, 2H), 8.02 (d, 1H, J = 8.6 Hz), 7.76 (s, 1H), 7.74 (d, 1H, J = 8.6 Hz), 7.51 (d, 2H, J = 8.9 Hz), 7.37 (d, 1H, J = 8.9 Hz), 7.18 (d, 2H, J = 8.9 Hz), 6.92 (s, 1H), 2.73 (s, 3H), 1.84 (s, 6H) |
| 59 | N-(3-(azetidin-1-yl)-5-(4-chlorophenoxy)phenyl)-5-(2-(methylsulfonyl)propan-2-yl)benzo[b]thiophene-2-carboxamide | LC/MS ESI (+): 555 (M + 1)<br>$^1$H-NMR (400 MHz, DMSO-$d_6$): δ 10.41 (s, 1H), 8.34 (s, 1H), 8.18 (s, 1H), 8.09 (d, 1H, J = 8.8 Hz), 7.74 (d, 1H, J = 8.8 Hz), 7.45 (d, 2H, |

TABLE 4-continued

| Ex. | Compound | Analysis data |
|---|---|---|
| | | J = 8.8 Hz), 7.08 (d, 2H, J = 9.2 Hz), 6.76-6.78 (m, 2H), 5.89 (s, 1H), 3.82 (t, 4H, J = 6.4 Hz), 2.74 (s, 3H), 2.33-2.34 (m, 2H), 1.85 (s, 6H) |
| 60 | N-(3-chloro-5-((6-chloropyridin-3-yl)oxy)phenyl)-5-(2-(methylsulfonyl)propan-2-yl)benzo[b]thiophene-2-carboxamide | LC/MS ESI (+): 535 (M + 1)<br>$^1$H-NMR (400 MHz, DMSO-d$_6$): δ 10.73 (s, 1H), 8.33-8.37 (m, 2H), 8.22 (s, 1H), 8.10 (d, 1H, J = 8.6 Hz), 7.71-7.79 (m, 3H), 7.62 (d, 1H, J = 8.7 Hz), 7.39 (s, 1H), 7.03 (s, 1H), 2.73 (s, 3H), 1.85 (s, 6H) |
| 61 | N-(3-chloro-5-((5-chloropyridin-2-yl)oxy)phenyl)-5-(2-(methylsulfonyl)propan-2-yl)benzo[b]thiophene-2-carboxamide | LC/MS ESI (+): 535 (M + 1)<br>$^1$H-NMR (400 MHz, DMSO-d$_6$): δ 10.76 (s, 1H), 8.36 (s, 1H), 8.28 (d, 1H, J = 2.6 Hz), 8.22 (s, 1H), 8.10 (d, 1H, J = 8.7 Hz), 7.03 (dd, 1H, J = 8.7, 2.7 Hz), 7.74-7.80 (m, 2H), 7.55 (s, 1H), 7.21 (d, 1H, J = 8.7 Hz), 7.09 (s, 1H), 2.73 (s, 3H), 1.85 (s, 6H) |

Example 62) Synthesis of N-(2-chloro-6-(3,5-dichlorophenoxy)pyridin-4-yl)-5-(2-(methylsulfonyl)propan-2-yl)benzo[b]thiophene-2-carboxamide (a) Synthesis of 2-chloro-6-(3,5-dichlorophenoxy)pyridine-4-amine 2,6-Dichloropyridine-4-amine (200.0 mg, 1.22 mmol) and 3,5-dichlorophenol (400.0 mg, 2.45 mmol) were dissolved in sulfolane (6.1 mL) and K$_2$CO$_3$ (339.0 mg, 2.45 mmol) was added. The reaction mixture was stirred at 160° C. for 16 hours, cooled to room temperature, H$_2$O was added, and extracted with EtOAc. The organic extract was washed with 1N NaOH aqueous solution and brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain 2-chloro-6-(3,5-dichlorophenoxy)pyridine-4-amine (121.0 mg, 34%) as a white solid.

LC/MS ESI (+): 289 (M+1)

$^1$H-NMR (400 MHz, DMSO-d$_6$): δ 7.46 (s, 1H), 7.24 (d, 2H, J=1.8 Hz), 6.63 (brs, 2H), 6.35 (d, 1H, J=1.6 Hz), 6.00 (d, 1H, J=1.6 Hz)

(b) Synthesis of N-(2-chloro-6-(3,5-dichlorophenoxy)pyridin-4-yl)-5-(2-(methylsulfonyl)propan-2-yl)benzo[b]thiophene-2-carboxamide 5-(2-(Methylsulfonyl)propan-2-yl)benzo[b]thiophene-2-carboxylic acid (50.0 mg, 0.16 mmol) was dissolved in CH$_2$Cl$_2$ (1.6 mL), and DMF (1.2 μL, 0.01 mmol) and (COCl)$_2$ (16.1 μL, 0.18 mmol) were added. The reaction mixture was stirred at 25° C. for 2 hours and concentrated under reduced pressure to obtain 5-(2-(methylsulfonyl)propan-2-yl)benzo[b]thiophene-2-carbonyl chloride. To the residue, 2-chloro-6-(3,5-dichlorophenoxy)pyridine-4-amine (50.9 mg, 0.17 mmol) and pyridine (550.0 μL) were added, stirred at 30° C. for 16 hours, and concentrated under reduced pressure. The residue was purified by reversed-phase column chromatography (C18-silica gel, 0.1% formic acid in CH$_3$CN:0.1% formic acid in H$_2$O) to obtain N-(2-chloro-6-(3,5-dichlorophenoxy)pyridin-4-yl)-5-(2-(methylsulfonyl)propan-2-yl)benzo[b]thiophene-2-carboxamide (62.0 mg, 65%) as a white solid.

LC/MS ESI (+): 569 (M+1)

$^1$H-NMR (400 MHz, DMSO-d$_6$): δ 11.14 (brs, 1H), 8.42 (s, 1H), 8.26 (d, 1H, J=2.8 Hz), 8.13 (d, 1H, J=8.7 Hz), 7.77 (dd, 1H, J=8.7, 1.8 Hz), 7.71 (d, 1H, J=1.3 Hz), 7.56 (t, 1H, J=1.8 Hz), 7.44 (d, 2H, J=1.8 Hz), 7.39 (d, 1H, J=1.4 Hz), 2.74 (s, 3H), 1.86 (s, 6H)

Compounds from Example 63 to Example 86 were synthesized through the synthesis route of Example 62, and data of these compounds are listed as follows.

TABLE 5

| Ex. | Compound | Analysis data |
|---|---|---|
| 63 | N-(6-chloro-4-(4-chlorophenoxy)pyridin-2-yl)-5-(2-(methylsulfonyl)propan-2-yl)benzo[b]thiophene-2-carboxamide | LC/MS ESI (+): 535 (M + 1)<br>$^1$H-NMR (400 MHz, DMSO-d$_6$): δ 11.59 (s, 1H), 8.60 (s, 1H), 8.13 (s, 1H), 8.09 (d, 1H, J = 8.8 Hz), 7.74-7.77 (m, 2H), 7.59 (d, 2H, J = 8.8 Hz), 7.33 (d, 2H, J = 8.8 Hz), 6.94 (s, 1H), 2.75 (s, 3H), 1.86 (s, 6H) |
| 64 | N-(2-chloro-6-(4-chlorophenoxy)pyridin-4-yl)-5-(2-(methylsulfonyl)propan-2-yl)benzo[b]thiophene-2-carboxamide | LC/MS ESI (+): 535 (M + 1)<br>$^1$H-NMR (400 MHz, DMSO-d$_6$): δ 11.10 (s, 1H), 8.39 (s, 1H), 8.26 (s, 1H), 8.12 (d, 1H, J = 8.8 Hz), 7.79 (d, 1H, J = 8.8 Hz), 7.67 (s, 1H), 7.53 (d, 2H, J = 8.8 Hz), 7.33 (s, 1H), 7.27 (d, 2H, J = 8.8 Hz), 2.75 (s, 3H), 1.86 (s, 6H) |

TABLE 5-continued

| Ex. | Compound | Analysis data |
|---|---|---|
| 65 | N-(2-chloro-6-((6-chloropyridin-3-yl)oxy)pyridin-4-yl)-5-(2-(methylsulfonyl)propan-2-yl)benzo[b]thiophene-2-carboxamide | LC/MS ESI (+): 536 (M + 1)<br>$^1$H-NMR (400 MHz, DMSO-$d_6$): δ 11.18 (brs, 1H), 8.39-8.41 (m, 2H), 8.25 (s, 1H), 8.11 (d, 1H, J = 8.7 Hz), 7.83 (d, 1H, J = 8.6 Hz), 7.76 (d, 1H, J = 8.7 Hz), 7.63-7.67 (m, 2H), 7.44 (s, 1H), 2.74 (s, 3H), 1.86 (s, 6H) |
| 66 | N-(4-chloro-6-(4-chlorophenoxy)pyridin-2-yl)-5-(2-(methylsulfonyl)propan-2-yl)benzo[b]thiophene-2-carboxamide | LC/MS ESI (+): 535 (M + 1)<br>$^1$H-NMR (400 MHz, DMSO-$d_6$): δ 11.27 (s, 1H), 8.54 (s, 1H), 8.15 (s, 1H), 8.09 (d, 1H, J = 8.8 Hz), 8.04 (s, 1H), 7.75 (dd, 1H, J = 8.8, 1.6 Hz), 7.51 (d, 2H, J = 8.8 Hz), 7.28 (d, 2H, J = 8.8 Hz), 6.93 (s, 1H), 2.74 (s, 3H), 1.85 (s, 6H) |
| 67 | N-(2-chloro-6-(4-(trifluoromethyl)phenoxy)pyridin-4-yl)-5-(2-(methylsulfonyl)propan-2-yl)benzo[b]thiophene-2-carboxamide | LC/MS ESI (+): 569 (M + 1)<br>$^1$H-NMR (400 MHz, DMSO-$d_6$): δ 11.15 (s, 1H), 8.42 (s, 1H), 8.27 (s, 1H), 8.14 (d, 1H, J = 8.8 Hz), 7.86 (d, 2H, J = 8.8 Hz), 7.79 (dd, 1H, J = 8.4, 2.0 Hz), 7.73 (s, 1H), 7.43-7.46 (m, 3H), 2.75 (s, 3H), 1.87 (s, 6H) |
| 68 | N-(2-chloro-6-(4-fluorophenoxy)pyridin-4-yl)-5-(2-(methylsulfonyl)propan-2-yl)benzo[b]thiophene-2-carboxamide | LC/MS ESI (+): 519 (M + 1)<br>$^1$H-NMR (400 MHz, DMSO-$d_6$): δ 11.11 (s, 1H), 8.41 (s, 1H), 8.27 (d, 1H, J = 1.6 Hz), 8.14 (d, 1H, J = 8.8 Hz), 7.79 (dd, 1H, J = 8.7, 1.9 Hz), 7.68 (d, 1H, J = 1.2 Hz), 7.27-7.35 (m, 5H), 2.76 (s, 3H) 1.87 (s, 6H) |
| 69 | N-(2-bromo-6-(4-chlorophenoxy)pyridin-4-yl)-5-(2-(methylsulfonyl)propan-2-yl)benzo[b]thiophene-2-carboxamide | LC/MS ESI (−): 577 (M − 1)<br>$^1$H-NMR (400 MHz, DMSO-$d_6$): δ 11.06 (s, 1H), 8.41 (s, 1H), 8.26 (s, 1H), 8.13 (d, 1H, J = 8.8 Hz), 7.83 (d, 1H, J = 1.6 Hz), 7.77 (dd, 1H, J = 8.8, 2.0 Hz), 7.54 (d, 2H, J = 8.8 Hz), 7.37 (s, 1H), 7.27 (d, 2H, J = 8.8 Hz), 2.75 (s, 3H), 1.87 (s, 6H) |
| 70 | N-(2-chloro-6-(3-chloro-5-methoxyphenoxy)pyridin-4-yl)-5-(2-(methylsulfonyl)propan-2-yl)benzo[b]thiophene-2-carboxamide | LC/MS ESI (+): 565 (M + 1)<br>$^1$H-NMR (400 MHz, DMSO-$d_6$): δ 11.15 (brs, 1H), 8.40 (s, 1H), 8.23 (d, 1H, J = 1.6 Hz), 8.10 (d, 1H, J = 8.7 Hz), 7.75 (dd, 1H, J = 8.7, 1.9 Hz), 7.69 (d, 1H, J = 1.4 Hz), 7.30 (d, 1H, J = 1.4 Hz), 6.96 (s, 1H), 6.91 (s, 1H), 6.81 (s, 1H), 3.79 (s, 3H), 2.70 (s, 3H), 1.85 (s, 6H) |
| 71 | N-(2-chloro-6-(3-chloro-4-fluorophenoxy)pyridin-4-yl)-5-(2-(methylsulfonyl)propan-2-yl)benzo[b]thiophene-2-carboxamide | LC/MS ESI (+): 553 (M + 1)<br>$^1$H-NMR (400 MHz, DMSO-$d_6$): δ 11.08 (brs, 1H), 8.39 (s, 1H), 8.24 (d, 1H, J = 1.6 Hz), 8.10 (d, 1H, J = 8.7 Hz), 7.76 (dd, 1H, J = 8.7, 1.9 Hz), 7.66 (s, 1H), 7.58 (dd, 1H, J = 6.3, 2.9 Hz), 7.52 (t, 1H, J = 9.0 Hz), 7.33 (d, 1H, J = 1.4 Hz), 7.27 (m, 1H), 2.70 (s, 3H), 1.85 (s, 6H) |
| 72 | N-(2-chloro-6-(4-chloro-3-fluorophenoxy)pyridin-4-yl)-5-(2-(methylsulfonyl)propan-2-yl)benzo[b]thiophene-2-carboxamide | LC/MS ESI (+): 553 (M + 1)<br>$^1$H-NMR (400 MHz, DMSO-$d_6$): δ 11.18 (brs, 1H), 8.40 (s, 1H), 8.25 (s, 1H), 8.12 (d, 1H, J = 8.7 Hz), 7.77 (dd, 1H, J = 8.7, 1.8 Hz), 7.66-7.71 (m, 2H), 7.46 (dd, 1H, J = 10.2, 2.7 Hz), 7.37 (s, 1H), 7.15 (m, 1H), 2.74 (s, 3H), 1.85 (s, 6H) |
| 73 | N-(2-chloro-6-(4-chlorophenoxy)pyridin-4-yl)-5-(1,1-dioxidotetrahydrothiophen-2-yl)benzo[b]thiophene-2-carboxamide | C/MS ESI (+): 533 (M + 1)<br>$^1$H-NMR (400 MHz, DMSO-$d_6$): δ 11.07 (s, 1H), 8.38 (s, 1H), 8.11 (d, 1H, J = 8.5 Hz), 8.05 (s, 1H), 7.67 (s, 1H), 7.52-7.55 (m, 3H), 7.33 (s, 1H), 7.26 (d, 2H, J = 8.9 Hz), 4.55 (m, 1H), 3.20-3.26 (m, 2H), 2.38-2.44 (m, 2H), 2.12-2.28 (m, 2H) |
| 74 | N-(2-chloro-6-(4-chlorophenoxy)pyridin-4-yl)-5-(1,1-dioxidotetrahydro-2H-thiopyran-2-yl)benzo[b]thiophene-2-carboxamide | LC/MS ESI (+): 547 (M + 1)<br>$^1$H-NMR (400 MHz, DMSO-$d_6$): δ 11.07 (s, 1H), 8.39 (s, 1H), 8.09 (d, 1H, J = 8.5 Hz), 8.03 (s, 1H), 7.67 (s, 1H), 7.51-7.54 (m, 3H), 7.33 (s, 1H), 7.26 (d, 2H, J = 8.9 Hz), 4.60 (m, 1H), 3.25-3.33 (m, 2H), 1.67-2.41 (m, 6H) |
| 75 | N-(2-chloro-6-(4-chlorophenoxy)pyrimidin-4-yl)-5-(2-(methylsulfonyl)propan-2-yl)benzo[b]thiophene-2-carboxamide | LC/MS ESI (+): 536 (M + 1)<br>$^1$H-NMR (400 MHz, DMSO-$d_6$): δ 12.11 (brs, 1H), 8.59 (s, 1H), 8.15 (s, 1H), 8.09 (d, 1H, J = 8.7 Hz), 7.76 (d, 1H, J = 8.7 Hz), 7.66 (s, 1H), 7.56 (d, 2H, J = 8.8 Hz), 7.34 (d, 2H, J = 8.8 Hz), 2.75 (s, 3H), 1.85 (s, 6H) |
| 76 | N-(6-chloro-2-(4-chlorophenoxy)pyrimidin-4-yl)-5-(2-(methylsulfonyl)propan-2-yl)benzo[b]thiophene-2-carboxamide | LC/MS ESI (+): 536 (M + 1)<br>$^1$H-NMR (400 MHz, DMSO-$d_6$): δ 12.00 (brs, 1H), 8.56 (s, 1H), 8.17 (s, 1H), 8.09 (d, 1H, J = 8.7 Hz), 7.98 (s, 1H), 7.75 (d, 1H, J = 10.2 Hz), 7.52 (d, 2H, J = 8.8 Hz), 7.33 (d, 2H, J = 8.8 Hz), 2.74 (s, 3H), 1.85 (s, 6H) |

TABLE 5-continued

| Ex. | Compound | Analysis data |
|---|---|---|
| 77 | N-(2-(4-chlorophenoxy)-6-fluoropyridin-4-yl)-5-(2-(methylsulfonyl)propan-2-yl)benzo[b]thiophene-2-carboxamide | LC/MS ESI (+): 519 (M + 1)<br>$^1$H-NMR (400 MHz, DMSO-d6): δ 11.17 (s, 1H), 8.41 (s, 1H), 8.26 (s, 1H), 8.13 (d, 1H, J = 8.4 Hz), 7.78 (d, 1H, J = 8.4 Hz), 7.54 (d, 2H, J = 8.8 Hz), 7.32 (s, 1H), 7.28 (d, 2H, J = 8.8 Hz), 7.21 (s, 1H), 2.75 (s, 3H), 1.86 (s, 6H) |
| 78 | N-(2-(bicyclo[2.2.1]hept-5-en-2-yloxy)-6-chloropyridin-4-yl)-5-(2-(methylsulfonyl)propan-2-yl)benzo[b]thiophene-2-carboxamide | LC/MS ESI (+): 517 (M + 1)<br>$^1$H-NMR (400 MHz, DMSO-d6): δ 10.89 (s, 1H), 8.37 (s, 1H), 8.24 (s, 1H), 8.11 (d, 1H, J = 8.8 Hz), 7.77 (d, 1H, J = 8.7 Hz), 7.41 (s, 1H), 7.14 (s, 1H), 6.38 (m, 1H), 6.01 (m, 1H), 5.40 (m, 1H), 3.25 (s, 1H), 2.86 (s, 1H), 2.73 (s, 3H), 2.22 (m, 1H), 1.85 (s, 6H), 1.42 (m, 2H), 0.92 (d, 1H, J = 13.0 Hz) |
| 79 | N-(2-chloro-6-(3,4-difluorophenoxy)pyridin-4-yl)-5-(2-(methylsulfonyl)propan-2-yl)benzo[b]thiophene-2-carboxamide | LC/MS ESI (+): 537 (M + 1)<br>$^1$H-NMR (400 MHz, DMSO-$d_6$): δ 11.11 (s, 1H), 8.41 (s, 1H), 8.26 (s, 1H), 8.15 (d, 1H, J = 8.8 Hz), 7.80 (d, 1H, J = 8.8 Hz), 7.69 (s, 1H), 7.55-7.57 (m, 2H), 7.36 (s, 1H), 7.14-7.15 (m, 1H), 2.75 (s, 3H) 1.86 (s, 6H) |
| 80 | N-(2-chloro-6-(3-chlorophenoxy)pyridin-4-yl)-5-(2-(methylsulfonyl)propan-2-yl)benzo[b]thiophene-2-carboxamide | LC/MS ESI (+): 535 (M + 1)<br>$^1$H-NMR (400 MHz, DMSO-$d_6$): δ 11.08 (brs, 1H), 8.31 (s, 1H), 8.17 (s, 1H), 8.04 (d, 1H, J = 8.8 Hz), 7.69 (d, 1H, J = 8.8 Hz), 7.61 (s, 1H), 7.43 (t, 1H, J = 8.0 Hz), 7.26-7.31 (m, 3H), 7.13 (d, 1H, J = 8.6 Hz), 2.67 (s, 3H), 1.89 (s, 6H) |
| 81 | N-(2-chloro-6-(3-(trifluoromethoxy)phenoxy)pyridin-4-yl)-5-(2-(methylsulfonyl)propan-2-yl)benzo[b]thiophene-2-carboxamide | LC/MS ESI (+): 585 (M + 1)<br>$^1$H-NMR (400 MHz, DMSO-$d_6$): δ 11.05 (s, 1H), 8.33 (s, 1H), 8.19 (d, 1H, J = 1.6 Hz), 8.05 (d, 1H, J = 8.7 Hz), 7.70 (dd, 1H, J = 8.7, 1.6 Hz), 7.62 (d, 1H, J = 1.2 Hz), 7.53 (t, 1H, J = 7.2 Hz), 7.32 (s, 1H), 7.21-7.26 (m, 3H), 2.67 (s, 3H), 1.79 (s, 6H) |
| 82 | N-(2-chloro-6-(3,4-dichlorophenoxy)pyridin-4-yl)-5-(2-(methylsulfonyl)propan-2-yl)benzo[b]thiophene-2-carboxamide | LC/MS ESI (+): 569 (M + 1)<br>$^1$H-NMR (400 MHz, DMSO-$d_6$): δ 11.04 (s, 1H), 8.34 (s, 1H), 8.19 (d, 1H, J = 1.6 Hz), 8.06 (d, 1H, J = 8.7 Hz), 7.71 (dd, 1H, J = 8.7, 1.6 Hz), 7.67 (d, 1H, J = 8.8 Hz), 7.53 (d, 1H, J = 1.6 Hz), 7.32 (d, 1H, J = 2.4 Hz), 7.3 (d, 1H, J = 2.4 Hz), 7.21 (dd, 1H, J = 8.0, 2.4 Hz), 2.67 (s, 3H), 1.79 (s, 6H) |
| 83 | N-(2-chloro-6-(4-chloro-2-fluorophenoxy)pyridin-4-yl)-5-(2-(methylsulfonyl)propan-2-yl)benzo[b]thiophene-2-carboxamide | LC/MS ESI (+): 553 (M + 1)<br>$^1$H-NMR (400 MHz, DMSO-$d_6$): δ 11.04 (s, 1H), 8.33 (s, 1H), 8.18 (s, 1H), 8.06 (d, 1H, J = 8.7 Hz), 7.71 (dd, 1H, J = 8.7, 1.6 Hz), 7.61 (s, 1H), 7.41 (d, 2H, J = 8.8 Hz), 7.29 (d, 2H, J = 8.8 Hz), 2.67 (s, 3H), 1.78 (s, 6H) |
| 84 | N-(2-chloro-6-(4-(trifluoromethoxy)phenoxy)pyridin-4-yl)-5-(2-(methylsulfonyl)propan-2-yl)benzo[b]thiophene-2-carboxamide | LC/MS ESI (+): 585 (M + 1)<br>$^1$H-NMR (400 MHz, DMSO-$d_6$): δ 11.11 (s, 1H), 8.40 (s, 1H), 8.26 (s, 1H), 8.13 (d, 1H, J = 8.8 Hz), 7.77 (d, 1H, J = 8.8 Hz), 7.68 (s, 1H,) 7.50 (s, 1H), 7.48 (s, 1H), 7.35-7.37 (m, 3H), 2.74 (s, 3H), 1.85 (s, 6H) |
| 85 | N-(2-chloro-6-((5-chloropyridin-2-yl)oxy)pyridin-4-yl)-5-(2-(methylsulfonyl)propan-2-yl)benzo[b]thiophene-2-carboxamide | LC/MS ESI (+): 536 (M + 1)<br>$^1$H-NMR (400 MHz, DMSO-$d_6$): δ 11.09 (s, 1H), 8.34 (s, 1H), 8.31 (d, 1H, J = 2.4 Hz), 8.19 (s, 1H), 8.01-8.07 (m, 2H), 7.71 (d, 1H, J = 8.8 Hz), 7.68 (d, 1H, J = 1.2 Hz), 7.41 (s, 1H), 7.23 (d, 1H, J = 8.8 Hz), 2.62 (s, 3H), 1.79 (s, 6H) |
| 86 | N-(2-chloro-6-((4-chlorobenzyl)oxy)pyridin-4-yl)-5-(2-(methylsulfonyl)propan-2-yl)benzo[b]thiophene-2-carboxamide | LC/MS ESI (+): 549 (M + 1)<br>$^1$H-NMR (400 MHz, DMSO-$d_6$): δ 10.91 (s, 1H), 8.32 (s, 1H), 8.18 (s, 1H), 8.05 (d, 1H, J = 8.8 Hz), 7.70 (d, 1H, J = 8.8 Hz), 7.38-7.44 (m, 5H) 7.24 (s, 1H), 5.26 (s, 2H), 2.67 (s, 3H), 1.78 (s, 6H) |

Example 87) Synthesis of N-(3-chloro-5-(2-(3-(prop-1-yn-1-yl)-5-(trifluoromethoxy)phenyl)propan-2-yl)phenyl)-5-(2-(methylsulfonyl)propan-2-yl)benzo[b]thiophene-2-carboxamide (a) Synthesis of 3-(2-(3-chloro-5-nitrophenyl)propan-2-yl)-5-(trifluoromethoxy)phenyl trifluoromethanesulfonate 3-(2-(3-Chloro-5-nitrophenyl)propan-2-yl)-5-(trifluoromethoxy)phenol (100.0 mg, 0.27 mmol) was dissolved in $CH_2Cl_2$ (2.7 mL), and pyridine (109.0 pt, 1.35 mmol) and $Tf_2O$ (45.0 μL, 0.27 mmol) were slowly added dropwise at 0° C. The reaction mixture was stirred at 0° C. for 2 hours, $H_2O$ was added, and extracted with $CH_2Cl_2$. The organic extract was washed with brine, dried over anhydrous $Na_2SO_4$ and concentrated under reduced pressure. The residue was purified by flash column chromatography (silica gel, n-Hex:EtOAc=9:1) to obtain 3-(2-(3-chloro-5-nitrophenyl)propan-2-yl)-5-(trifluoromethoxy)phenyl trifluoromethanesulfonate (120.0 mg, 88%) as a colorless liquid.

$^1$H-NMR (400 MHz, $CDCl_3$): δ 8.13 (t, 1H, J=1.9 Hz), 7.99 (t, 1H, J=1.9 Hz), 7.45 (t, 1H, J=1.8 Hz), 7.08-7.10 (m, 2H), 7.04 (t, 1H, J=1.9 Hz), 1.75 (s, 6H)

(b) Synthesis of 1-chloro-3-nitro-5-(2-(3-(prop-1-yn-1-yl)-5-(trifluoromethoxy)phenyl)propan-2-yl)benzene 3-(2-(3-Chloro-5-nitrophenyl)propan-2-yl)-5-(trifluoromethoxy)phenyl trifluoromethanesulfonate (280.0 mg, 0.55 mmol) was dissolved in anhydrous DMF (5.5 mL), and 1-(trimethylsilyl)-1-propyne (123.0 μL, 0.83 mmol), $Pd(PPh_3)_4$ (64.0 mg, 0.06 mmol), CuI (21.0 mg, 0.11 mmol) and DIPEA (480.0 μL, 2.75 mmol) were added at room temperature. The reaction mixture was stirred at 90° C. for 15 hours, cooled to room temperature, $H_2O$ was added, and extracted with $CH_2Cl_2$. The organic extract was washed with brine, dried over anhydrous $Na_2SO_4$ and concentrated under reduced pressure. The residue was purified by flash column chromatography (silica gel, n-Hex:$CH_2Cl_2$=4:1) to obtain 1-chloro-3-nitro-5-(2-(3-(prop-1-yn-1-yl)-5-(trifluoromethoxy)phenyl)propan-2-yl)benzene (120.0 mg, 55%) as a colorless liquid.

$^1$H-NMR (400 MHz, $CDCl_3$): δ 8.08 (t, 1H, J=1.9 Hz), 7.99 (t, 1H, J=1.9 Hz), 7.46 (t, 1H, J=1.8 Hz), 7.11-7.13 (m, 2H), 6.94 (s, 1H), 2.04 (s, 3H), 1.70 (s, 6H)

(c) Synthesis of 3-chloro-5-(2-(3-(prop-1-yn-1-yl)-5-(trifluoromethoxy)phenyl)propan-2-yl)aniline The synthesis procedure of Example 1-g was repeated except for using 1-chloro-3-nitro-5-(2-(3-(prop-1-yn-1-yl)-5-(trifluoromethoxy)phenyl)propan-2-yl)benzene (120.0 mg, 0.32 mmol) as a starting material to obtain 3-chloro-5-(2-(3-(prop-1-yn-1-yl)-5-(trifluoromethoxy)phenyl)propan-2-yl)aniline (93.0 mg, 84%).

LC/MS ESI (+): 368 (M+1)

(d) Synthesis of N-(3-chloro-5-(2-(3-(prop-1-yn-1-yl)-5-(trifluoromethoxy)phenyl)propan-2-yl)phenyl)-5-(2-(methylsulfonyl)propan-2-yl)benzo[b]thiophene-2-carboxamide The synthesis procedure of Example 1-h was repeated except for using 3-chloro-5-(2-(3-(prop-1-yn-1-yl)-5-(trifluoromethoxy)phenyl)propan-2-yl)aniline (55.0 mg, 0.15 mmol) as a starting material to obtain N-(3-chloro-5-(2-(3-(prop-1-yn-1-yl)-5-(trifluoromethoxy)phenyl)propan-2-yl)phenyl)-5-(2-(methylsulfonyl)propan-2-yl)benzo[b]thiophene-2-carboxamide (23.5 mg, 33%).

LC/MS ESI (+): 648 (M+1)

$^1$H-NMR (400 MHz, DMSO-$d_6$): δ 10.65 (s, 1H), 8.34 (s, 1H), 8.20 (s, 1H), 8.10 (d, 1H, J=8.8 Hz), 7.90 (s, 1H), 7.74 (d, 1H, J=8.8 Hz), 7.50 (s, 1H), 7.19-7.22 (m, 3H), 7.07 (s, 1H), 2.73 (s, 3H), 2.03 (s, 3H), 1.85 (s, 6H), 1.65 (s, 6H)

Example 88) Synthesis of N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide (a) Synthesis of 4-(4-chlorophenyl)-4-methyl-3-oxopentanenitrile 2-(4-Chlorophenyl)-2-methylpropanic acid (500.0 mg, 2.52 mmol) was dissolved in THF (10.0 mL), carbonyldiimidazole (490.0 mg, 3.02 mmol) was added, and stirred for 2 hours. To the reaction mixture was added a solution prepared by dissolving $CH_3CN$ (0.2 mL, 8.31 mmol) in THF (10.0 mL), adding 1.6M solution of n-BuLi in THF (4.7 mL, 7.56 mmol) slowly dropwise at −78° C. and stirring for 1 hour. The resulting mixture was stirred at −78° C. for 2 hours, $H_2O$ was added, and extracted with EtOAc. The organic extract was washed with brine, dried over anhydrous $Na_2SO_4$ and concentrated under reduced pressure. The residue was purified by flash column chromatography (silica gel, n-Hex:$CH_2Cl_2$=1:2) to obtain 4-(4-chlorophenyl)-4-methyl-3-oxopentanenitrile (333.0 mg, 59%) as an off-white oil.

LC/MS ESI (−): 220 (M−1)

$^1$H-NMR (400 MHz, $CDCl_3$): δ 7.38 (d, 2H, J=8.4 Hz), 7.19 (d, 2H, J=8.8 Hz), 3.30 (s, 2H), 1.53 (s, 6H)

(b) Synthesis of 1-(tert-butyl)-3-(2-(4-chlorophenyl)propan-2-yl)-1H-pyrazole-5-amine tert-Butylhydrazine chloride (463.0 mg, 3.72 mmol) was dissolved in EtOH (1.9 mL), and NaOH (119.0 g, 2.97 mmol) was added. 4-(4-Chlorophenyl)-4-methyl-3-oxopentanenitrile (330.0 mg, 1.49 mmol) in EtOH (1.0 mL) was added to the reaction mixture dropwise. The reaction mixture was stirred at 80° C. for 12 hours, $H_2O$ was added, and extracted with EtOAc. The organic extract was dried over $Na_2SO_4$ and concentrated under reduced pressure. The residue was purified by flash column chromatography (amine silica gel, n-Hex:EtOAc=1:1) to obtain 1-(tert-butyl)-3-(2-(4-chlorophenyl)propan-2-yl)-1H-pyrazole-5-amine (130.0 mg, 30%) as a white solid.

LC/MS ESI (+): 292 (M+1)

$^1$H-NMR (400 MHz, $CDCl_3$): δ 7.25 (d, 2H, J=9.2 Hz), 7.19 (d, 2H, J=8.8 Hz), 5.24 (s, 1H), 3.41 (s, 2H), 1.62 (s, 9H), 1.59 (s, 6H)

(c) Synthesis of N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide The synthesis procedure of Example 1-h was repeated except for using 1-(tert-butyl)-3-(2-(4-chlorophenyl)propan-2-yl)-1H-pyrazole-5-amine (100.0 mg, 0.34 mmol) as a starting material to obtain N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide (78.0 mg, 40%).

LC/MS ESI (+): 572 (M+1)

$^1$H-NMR (400 MHz, DMSO-$d_6$): δ 10.35 (s, 1H), 8.27 (s, 1H), 8.26 (s, 1H), 8.10 (d, 1H, J=8.8 Hz), 7.76 (d, 1H, J=8.8 Hz), 7.30-7.35 (m, 4H), 6.08 (s, 1H), 2.74 (s, 3H), 1.85 (s, 6H), 1.63 (s, 6H), 1.57 (s, 9H).

Example 89) Synthesis of N-(3-(2-(4-chlorophenyl)propan-2-yl)-1H-pyrazol-5-yl)-5-(2-(methylsulfonyl)propan-2-yl)benzo[b]thiophene-2-carboxamide N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide (30.0 mg, 0.05 mmol) was dissolved in formic acid (4.0 mL). The reaction mixture was stirred at 80° C. for 12 hours and concentrated under reduced pressure, basified with sat. NaHCO$_3$ aqueous solution (pH=9) and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain N-(3-(2-(4-chlorophenyl)propan-2-yl)-1H-pyrazol-5-yl)-5-(2-(methylsulfonyl)propan-2-yl)benzo[b]thiophene-2-carboxamide (17.0 mg, 67%) as a white solid.

LC/MS ESI (+): 516 (M+1)

$^1$H-NMR (400 MHz, DMSO-$d_6$): δ 12.30 (s, 1H), 11.23 (s, 1H), 8.44 (s, 1H), 8.13 (s, 1H), 8.09 (d, 1H, J=8.8 Hz), 7.74 (d, 1H, J=8.8 Hz), 7.38 (d, 2H, J=8.4 Hz), 7.29 (d, 2H, J=8.4 Hz), 6.50 (s, 1H), 2.74 (s, 3H), 1.86 (s, 6H), 1.67 (s, 6H)

Example 90 and Example 91) Synthesis of N-(2-chloro-6-(2-(3-methoxy-5-(trifluoromethoxy)phenyl)propan-2-yl)pyridin-4-yl)-5-(2-(methylsulfonyl)propan-2-yl)benzo[b]thiophene-2-carboxamide and N-(4-chloro-6-(2-(3-methoxy-5-(trifluoromethoxy)phenyl)propan-2-yl)pyridin-2-yl)-5-(2-(methylsulfonyl)propan-2-yl)benzo[b]thiophene-2-carboxamide (a) Synthesis of 4,6-dichloro-N-methoxy-N-methylisonicotinamide 4,6-Dichloroisonicotinic acid (3.0 g, 15.6 mmol) was dissolved in anhydrous CH$_2$Cl$_2$ (100.0 mL), and (COCl)$_2$ (2.1 mL, 23.40 mmol) and anhydrous DMF were added dropwise in a catalytic amount, followed by stirring at 0° C. for 1 hour. The reaction mixture was dried under reduced pressure for 1 hour, the residue was dissolved in anhydrous CH$_2$Cl$_2$ (100.0 mL), and N,O-dimethylhydroxyamine (4.6 g, 46.80 mmol) and pyridine (7.5 mL, 93.60 mmol) were added at 0° C. The reaction mixture was stirred at 0° C. for 1 hour, H$_2$O was added, and extracted with CH$_2$Cl$_2$. The organic extract was washed with brine, dried over anhydrous Na$_2$SO$_4$ and concentrated under reduced pressure. The residue was purified by flash column chromatography (amine silica gel, n-Hex:EtOAc=1:4) to obtain 4,6-dichloro-N-methoxy-N-methylisonicotinamide (3.5 g, 83%) as a white solid.

LC/MS ESI (+): 235 (M+1)

$^1$H-NMR (400 MHz, CDCl$_3$): δ 7.56 (brs, 1H), 7.44 (s, 1H), 3.80 (s, 3H), 3.36 (s, 3H)

(b) Synthesis of (4,6-di chloropyridin-2-yl)(3-methoxy-5-(trifluoromethoxy)phenyl)methanone 1-Bromo-3-methoxy-5-(trifluoromethoxy)benzene (5.0 g, 18.45 mmol) was dissolved in THF (90.0 mL), 1.7M solution of tert-BuLi in pentane (11.4 mL, 19.30 mmol) was added dropwise at −78° C., and stirred for 1 hour. 4,6-Dichloro-N-methoxy-N-methylisonicotinamide (3.5 g, 14.88 mmol) in THF (10.0 mL) was slowly added, and the reaction mixture was stirred at 0° C. for 2 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex: CH$_2$Cl$_2$=1:10) to obtain (4,6-dichloropyridin-2-yl)(3-methoxy-5-(trifluoromethoxy)phenyl)methanone (2.4 g, 44%) as a yellow solid.

LC/MS ESI (+): 366 (M+1)

$^1$H-NMR (400 MHz, CDCl$_3$): δ 8.00 (s, 1H), 7.63 (s, 1H), 7.61 (s, 1H), 7.59 (s, 1H), 7.01 (s, 1H), 3.89 (s, 3H)

(c) Synthesis of 2,4-dichloro-6-(dichloro(3-methoxy-5-(trifluoromethoxy)phenyl)methyl)pyridine The synthesis procedure of Example 1-c was repeated except for using (4,6-dichloropyridin-2-yl)(3-methoxy-5-(trifluoromethoxy)phenyl)methanone (2.4 g, 6.55 mmol) as a starting material to obtain 2,4-dichloro-6-(dichloro(3-methoxy-5-(trifluoromethoxy)phenyl)methyl)pyridine (2.1 g, 76%).

LC/MS ESI (+): 420 (M+1)

$^1$H-NMR (400 MHz, CDCl$_3$): 7.76 (s, 1H), 7.37 (s, 1H), 7.13 (s, 1H), 7.06 (s, 1H), 6.77 (s, 1H), 3.84 (s, 3H)

(d) Synthesis of 2,4-di chloro-6-(2-(3-methoxy-5-(trifluoromethoxy)phenyl)propan-2-yl)pyridine The synthesis procedure of Example 1-d was repeated except for using 2,4-dichloro-6-(dichloro(3-methoxy-5-(trifluoromethoxy)phenyl)methyl)pyridine (2.1 g, 4.98 mmol) as a starting material to obtain 2,4-dichloro-6-(2-(3-methoxy-5-(trifluoromethoxy)phenyl)propan-2-yl)pyridine (1.3 g, 69%) as an off-white oil.

LC/MS ESI (+): 380 (M+1)

$^1$H-NMR (400 MHz, CDCl$_3$): δ 7.19 (s, 1H), 6.94 (s, 1H), 6.73 (s, 1H), 6.70 (s, 1H), 6.62 (s, 1H), 3.79 (s, 3H), 1.69 (s, 6H)

(e) Synthesis of 2-chloro-6-(2-(3-methoxy-5-(trifluoromethoxy)phenyl)propan-2-yl)pyridine-4-amine and (f) synthesis of 4-chloro-6-(2-(3-methoxy-5-(trifluoromethoxy)phenyl)propan-2-yl)pyridine-2-amine 2,4-Dichloro-6-(2-(3-methoxy-5-(tri fluoromethoxy)phenyl)propan-2-yl)pyridine (50.0 mg, 0.13 mmol), NaN$_3$ (17.0 mg, 0.26 mmol), Cu$_2$O (18.7 mg, 0.131 mmol) and L-proline (19.5 mg, 0.17 mmol) were dissolved in anhydrous DMSO (1.0 mL). The reaction mixture was stirred at 100° C. for 12 hours, cooled to room temperature, H$_2$O was added, and extracted with EtOAc. The organic extract was dried over anhydrous Na$_2$SO$_4$ and concentrated under reduced pressure. The residue was purified by flash column chromatography (amine silica gel, n-Hex:EtOAc=9:1) to obtain 2-chloro-6-(2-(3-methoxy-5-(trifluoromethoxy)phenyl)propan-2-yl)pyridine-4-amine (14.0 mg, 30%) and 4-chloro-6-(2-(3-methoxy-5-(trifluoromethoxy)phenyl)propan-2-yl)pyri dine-2-amine (4.0 mg, 8%) as an off-white oil.

(e) LC/MS ESI (+): 361 (M+1)
$^1$H-NMR (400 MHz, CDCl$_3$): δ 6.74 (s, 1H), 6.72 (s, 1H), 6.96 (s, 1H), 6.37 (d, 1H, J=1.2 Hz), 6.14 (d, 1H, J=1.2 Hz), 4.13 (brs, 2H), 3.76 (s, 3H), 1.64 (s, 6H)

(f) LC/MS ESI (+): 361 (M+1)
$^1$H-NMR (400 MHz, CDCl$_3$): δ 6.72 (s, 1H), 6.71 (s, 1H), 6.59 (s, 1H), 6.48 (s, 1H), 6.32 (s, 1H), 4.43 (brs, 2H), 3.77 (s, 3H), 1.62 (s, 6H)

(g) Synthesis of N-(2-chloro-6-(2-(3-methoxy-5-(trifluoromethoxy)phenyl)propan-2-yl)pyridin-4-yl)-5-(2-(methylsulfonyl)propan-2-yl)benzo[b]thiophene-2-carboxamide The synthesis procedure of Example 1-h was repeated except for using 2-chloro-6-(2-(3-methoxy-5-(trifluoromethoxy)phenyl)propan-2-yl)pyridine-4-amine (38.0 mg, 0.11 mmol) as a starting material to obtain N-(2-chloro-6-(2-(3-methoxy-5-(trifluoromethoxy)phenyl)propan-2-yl)pyridin-4-yl)-5-(2-(methylsulfonyl)propan-2-yl)benzo[b]thiophene-2-carboxamide (20.0 mg, 30%) as a white solid.
LC/MS ESI (+): 641 (M+1)
$^1$H-NMR (400 MHz, DMSO-d$_6$): δ 10.99 (s, 1H), 8.39 (s, 1H), 8.24 (s, 1H), 8.13 (d, 1H, J=8.8 Hz), 7.89 (s, 1H), 7.77 (d, 1H, J=8.8 Hz), 7.56 (s, 1H), 6.84 (s, 1H), 6.83 (s, 1H), 6.77 (s, 1H), 3.79 (s, 3H), 2.75 (s, 3H), 1.86 (s, 6H), 1.68 (s, 6H)

(h) Synthesis of N-(4-chloro-6-(2-(3-methoxy-5-(trifluoromethoxy)phenyl)propan-2-yl)pyridin-2-yl)-5-(2-(methylsulfonyl)propan-2-yl)benzo[b]thiophene-2-carboxamide The synthesis procedure of Example 1-h was repeated except for using 4-chloro-6-(2-(3-methoxy-5-(trifluoromethoxy)phenyl)propan-2-yl)pyridine-2-amine (20.0 mg, 0.06 mmol) as a starting material to obtain N-(4-chloro-6-(2-(3-methoxy-5-(trifluoromethoxy)phenyl)propan-2-yl)pyridin-2-yl)-5-(2-(methylsulfonyl)propan-2-yl)benzo[b]thiophene-2-carboxamide (12.0 mg, 34%) as a white solid.
LC/MS ESI (+): 641 (M+1)
$^1$H-NMR (400 MHz, DMSO-d$_6$): δ 11.16 (s, 1H), 8.64 (s, 1H), 8.19 (s, 1H), 8.11 (d, 1H, J=8.8 Hz), 8.09 (d, 1H, J=2.0 Hz), 7.77 (dd, 1H, J=8.8, 2.0 Hz), 7.20 (s, 1H), 6.86 (s, 1H), 6.79-6.81 (m, 2H), 3.78 (s, 3H), 2.76 (s, 3H), 1.86 (s, 6H), 1.74 (s, 6H)

Example 92) Synthesis of N-(3-chloro-5-((2,2,6,6-tetramethylpiperidin-4-yl)oxy)phenyl)-5-(2-(methylsulfonyl)propan-2-yl)benzo[b]thiophene-2-carboxamide (a) Synthesis of 4-(3-bromo-5-chlorophenoxy)-2,2,6,6-tetramethylpiperidine 1-Bromo-3-chloro-5-nitrobenzene (200.0 mg, 0.42 mmol) was dissolved in anhydrous DMF (2.1 mL), and 2,2,6,6-tetramethylpiperidin-4-ol (66.0 mg, 0.42 mmol) and 60 wt % NaH (50.4 mg, 1.26 mmol) were added. The reaction mixture was stirred at room temperature for 2 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex: EtOAc=9:1) to obtain 4-(3-bromo-5-chlorophenoxy)-2,2,6,6-tetramethylpiperidine (160.0 mg, 54%) as an off-white oil.

LC/MS ESI (+): 346 (M+1)
$^1$H-NMR (400 MHz, CDCl$_3$): δ 7.09 (s, 1H), 6.93 (s, 1H), 6.81 (s, 1H), 4.60 (m, 1H), 2.02-2.06 (m, 2H), 1.20-1.30 (m, 14H)

(b) Synthesis of 3-chloro-5-((2,2,6,6-tetramethylpiperidin-4-yl)oxy)aniline

The synthesis procedure of Example 91-e was repeated except for using 4-(3-bromo-5-chlorophenoxy)-2,2,6,6-tetramethylpiperidine (34.0 mg, 0.10 mmol) as a starting material to obtain 3-chloro-5-((2,2,6,6-tetramethylpiperidin-4-yl)oxy)aniline (16.0 mg, 58%).
LC/MS ESI (+): 283 (M+1)
$^1$H-NMR (400 MHz, CDCl$_3$): δ 6.31 (s, 1H), 6.29 (s, 1H), 6.10 (s, 1H), 4.58 (m, 1H), 3.70 (brs, 2H), 2.03-2.05 (m, 2H), 1.18-1.23 (m, 14H)

(c) Synthesis of N-(3-chloro-5-(2,2,6,6-tetramethyl-piperidin-4-yl)oxy)phenyl)-5-(2-(methylsulfonyl)propan-2-yl)benzo[b]thiophene-2-carboxamide The synthesis procedure of Example 1-h was repeated except for using 3-chloro-5-((2,2,6,6-tetramethylpiperidin-4-yl)oxy)aniline (16.0 mg, 0.06 mmol) as a starting material to obtain N-(3-chloro-5-((2,2,6,6-tetramethylpiperidin-4-yl)oxy)phenyl)-5-(2-(methylsulfonyl)propan-2-yl)benzo[b]thiophene-2-carboxamide (9.0 mg, 28%) as a white solid.
LC/MS ESI (+): 563 (M+1)
$^1$H-NMR (400 MHz, DMSO-d$_6$): δ 10.53 (s, 1H), 8.28 (s, 1H), 8.16 (s, 1H), 8.03 (d, 1H, J=8.8 Hz), 7.68 (dd, 1H, J=8.8, 2.0 Hz), 7.41 (s, 1H), 7.33 (s, 1H), 6.73 (s, 1H), 4.66-4.71 (m, 1H), 1.88 (dd, 2H, J=12.4, 4.0 Hz), 1.79 (s, 6H), 1.14 (s, 6H), 1.07-1.10 (m, 2H), 1.02 (s, 6H)

Example 93) Synthesis tert-butyl (2-(3-(4-chlorophenoxy)-5-(5-(2-(methylsulfonyl)propan-2-yl)benzo[b]thiophene-2-carboxamido)phenoxy)ethyl)carbamate (a) Synthesis of 1-(4-chlorophenoxy)-3-methoxy-5-nitrobenzene The synthesis procedure of Example 40-a was repeated except for using 1-bromo-3-methoxy-5-nitrobenzene (500.0 mg 1.71 mmol) as a starting material to obtain 1-(4-chlorophenoxy)-3-methoxy-5-nitrobenzene (400.0 mg, 66%).
LC/MS ESI (+): 280 (M+1)
$^1$H-NMR (400 MHz, CDCl$_3$): δ 7.48 (t, 1H, J=2.2 Hz), 7.37 (t, 1H, J=2.1 Hz), 7.36 (d, 2H, J=8.8 Hz), 7.00 (d, 2H, J=8.9 Hz), 6.83 (t, 1H, J=2.1 Hz), 3.87 (s, 3H)

(b) Synthesis of 3-(4-chlorophenoxy)-5-nitrophenol

The synthesis procedure of Example 1-e was repeated except for using 1-(4-chlorophenoxy)-3-methoxy-5-nitrobenzene (396.0 mg, 1.42 mmol) as a starting material to obtain 3-(4-chlorophenoxy)-5-nitrophenol (307.0 mg, 82%).
LC/MS ESI (+): 266 (M+1)
$^1$H-NMR (400 MHz, CDCl$_3$): δ 7.39 (t, 1H, J=2.2 Hz), 7.35 (d, 2H, J=8.9 Hz), 7.33 (t, 1H, J=2.1 Hz), 6.98 (d, 2H, J=8.9 Hz), 6.74 (t, 1H, J=2.2 Hz)

(c) Synthesis of tert-butyl (2-(3-(4-chlorophenoxy)-5-nitrophenoxy)ethyl)carbamate 3-(4-Chlorophenoxy)-5-nitrophenol (297.0 mg, 1.11 mmol) was dissolved in anhydrous DMF (10.0 mL), K$_2$CO$_3$ (231.0 mg, 1.68 mmol) was added, stirred at room temperature for 10 minutes, and tert-butyl (2-bromoethyl)carbamate (300.0 mg, 1.34 mmol) was added. The reaction mixture was stirred at room temperature for 16 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=6:1) to obtain tert-butyl (2-(3-(4-chlorophenoxy)-5-nitrophenoxy)ethyl)carbamate (435.0 mg, 95%).

LC/MS ESI (+): 409 (M+1)

$^1$H-NMR (400 MHz, CDCl$_3$): δ 7.44 (t, 1H, J=2.1 Hz), 7.37 (t, 1H, J=2.1 Hz), 7.36 (d, 2H, J=8.9 Hz), 6.98 (d, 2H, J=8.9 Hz), 6.79 (t, 1H, J=2.2 Hz), 4.90 (brs, 1H), 4.04 (t, 2H, J=5.1 Hz), 3.51-3.55 (m, 2H), 1.43 (s, 9H)

(d) Synthesis of tert-butyl (2-(3-amino-5-(4-chlorophenoxy)phenoxy)ethyl)carbamate The synthesis procedure of Example 1-g was repeated except for using tert-butyl (2-(3-(4-chlorophenoxy)-5-nitrophenoxy)ethyl)carbamate (425.0 mg, 1.04 mmol) as a starting material to obtain tert-butyl (2-(3-amino-5-(4-chlorophenoxy)phenoxy)ethyl)carbamate (360.0 mg, 92%).

LC/MS ESI (+): 379 (M+1)

$^1$H-NMR (400 MHz, CDCl$_3$): δ 7.28 (d, 2H, J=8.9 Hz), 6.96 (d, 2H, J=8.9 Hz), 5.98 (t, 1H, J=2.0 Hz), 5.91-5.94 (m, 2H), 3.92 (t, 2H, J=5.0 Hz), 3.73 (brs, 2H), 3.46-3.50 (m, 2H), 1.44 (s, 9H)

(e) Synthesis of tert-butyl(2-(3-(4-chlorophenoxy)-5-(5-(2-(methylsulfonyl)propan-2-yl)benzo[b]thiophene-2-carboxamido)phenoxy)ethyl)carbamate The synthesis procedure of Example 1-h was repeated except for using tert-butyl (2-(3-amino-5-(4-chlorophenoxy)phenoxy)ethyl)carbamate (211.0 mg, 0.56 mmol) as a starting material to obtain tert-butyl (2-(3-(4-chlorophenoxy)-5-(5-(2-(methylsulfonyl)propan-2-yl)benzo[b]thiophene-2-carboxamido)phenoxy)ethyl)carbamate (360.0 mg, 98%) as a white solid.

LC/MS ESI (+): 682 (M+Na)

$^1$H-NMR (400 MHz, DMSO-d$_6$): δ 10.53 (brs, 1H), 8.33 (s, 1H), 8.19 (s, 1H), 8.08 (d, 1H, J=8.7 Hz), 7.73 (d, 1H, J=8.7 Hz), 7.47 (d, 2H, J=8.7 Hz), 7.29 (s, 1H), 7.12 (d, 2H, J=8.9 Hz), 7.02-7.04 (m, 2H), 6.44 (s, 1H), 3.94-3.97 (m, 2H), 3.28-3.32 (m, 2H), 2.73 (s, 3H), 1.85 (s, 6H), 1.38 (s, 9H)

Example 94) Synthesis of N-(3-(2-aminoethoxy)-5-(4-chlorophenoxy)phenyl)-5-(2-(methylsulfonyl)propan-2-yl)benzo[b]thiophene-2-carboxamide tert-Butyl (2-(3-(4-chlorophenoxy)-5-(5-(2-(methylsulfonyl)propan-2-yl)benzo[b]thiophene-2-carboxamido)phenoxy)ethyl)carbamate (187.0 mg, 0.28 mmol) were dissolved in anhydrous CH$_2$Cl$_2$ (3.0 mL) and TFA (220.0 μL, 2.84 mmol) was added at 0° C. The reaction mixture was stirred at room temperature for 5 hours, sat. NaHCO$_3$ was added, and extracted with CH$_2$Cl$_2$. The organic extract was washed with brine, dried over anhydrous Na$_2$SO$_4$ and concentrated under reduced pressure. The residue was purified by flash column chromatography (amine silica gel, CH$_2$Cl$_2$:MeOH=20:1) to obtain N-(3-(2-aminoethoxy)-5-(4-chlorophenoxy)phenyl)-5-(2-(methylsulfonyl)propan-2-yl)benzo[b]thiophene-2-carboxamide (81.0 mg, 51%) as a white solid.

LC/MS ESI (+): 559 (M+1)

$^1$H-NMR (400 MHz, DMSO-d$_6$): δ 10.54 (brs, 1H), 8.35 (s, 1H), 8.20 (s, 1H), 8.09 (d, 1H, J=8.7 Hz), 7.74 (d, 1H, J=8.7 Hz), 7.50 (d, 2H, J=8.7 Hz), 7.32 (s, 1H), 7.12 (d, 2H, J=8.9 Hz), 7.04 (s, 1H), 6.42 (s, 1H), 3.90-3.94 (t, 2H, J=5.6 Hz), 2.87-2.90 (t, 2H, J=5.6 Hz), 2.51 (s, 3H), 2.00 (brs, 2H), 1.85 (s, 6H)

Example 95) Synthesis of N-(5-chloro-2',4'-difluoro-[1,1'-biphenyl]-3-yl)-5-((methylsulfonyl)methyl)benzo[b]thiophene-2-carboxamide (a) Synthesis of 3'-chloro-2,4-difluoro-5'-nitro-1,1'-biphenyl 1-Bromo-3-chloro-5-nitrobenzene (1.0 g, 4.23 mmol), (2,4-difluorophenyl)boronic acid (0.7 g, 4.23 mmol), Pd(PPh$_3$)$_4$ (490.0 mg, 0.42 mmol) and Na$_2$CO$_3$ (1.4 g, 12.70 mmol) were added to a mixture of DME/H$_2$O (42.0 mL, 4/1 v/v). The reaction mixture was stirred at 90° C. for 3 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain 3'-chloro-2,4-difluoro-5'-nitro-1,1'-biphenyl (1.1 g, 96%) as a white solid.

$^1$H-NMR (400 MHz, CDCl$_3$): δ 8.27 (s, 1H), 8.23 (s, 1H), 7.83 (s, 1H), 7.26-7.46 (m, 1H), 6.98-7.03 (m, 2H)

(b) Synthesis of 5-chloro-2',4'-difluoro-[1,1'-biphenyl]-3-amine

The synthesis procedure of Example 1-g was repeated except for using 3'-chloro-2,4-difluoro-5'-nitro-1,1'-biphenyl (1.1 g, 4.08 mmol) as a starting material to obtain 5-chloro-2',4'-difluoro-[1,1'-biphenyl]-3-amine (830.0 mg, 85%).

$^1$H-NMR (400 MHz, CDCl$_3$): δ 7.33-7.37 (m, 1H), 6.85-6.93 (m, 3H), 6.68 (m, 2H), 3.81 (brs, 2H)

(c) Synthesis of N-(5-chloro-2',4'-difluoro-[1,1'-biphenyl]-3-yl)-5-((methylsulfonyl)methyl)benzo[b]thiophene-2-carboxamide The synthesis procedure of Example 1-h was repeated except for using 5-chloro-2',4'-difluoro-[1,1'-biphenyl]-3-amine (40.0 mg, 0.17 mmol) as a starting material to obtain N-(5-chloro-2',4'-difluoro-[1,1'-biphenyl]-3-yl)-5-((methylsulfonyl)methyl)benzo[b]thiophene-2-carboxamide (30.8 mg, 41%).

LC/MS ESI (+): 492 (M+1)

$^1$H-NMR (400 MHz, DMSO-d$_6$): δ 10.76 (s, 1H), 8.40 (s, 1H), 8.11 (d, 1H, J=8.4 Hz), 8.06 (s, 1H), 8.00 (m, 1H), 7.91 (m, 1H), 7.66 (m, 1H), 7.54 (d, 1H, J=8.4 Hz), 7.43 (m, 1H), 7.37 (m, 1H), 7.25 (m, 1H), 4.65 (s, 2H), 2.94 (s, 3H)

Example 96) Synthesis of (8-chloro-6-(4-chlorophenoxy)-2,3-dihydro-4H-benzo[b][1,4]oxazin-4-yl)(5-(2-(methylsulfonyl)propan-2-yl)benzo[b]thiophen-2-yl)methanone (a) Synthesis of 6-bromo-8-chloro-3,4-dihydro-2H-benzo[b][1,4]oxazine 2-Amino-4-bromo-6-chlorophenol (100.0 mg, 0.45 mmol), dibromoethane (0.1 mL, 1.12 mmol) and K$_2$CO$_3$ (186.0 mg, 1.35 mmol) were dissolved in anhydrous DMF (1.5 mL). The reaction mixture was stirred at 125° C. for 15 hours, H₂O was added, and extracted with EtOAc. The organic extract was washed with brine, dried over anhydrous Na₂SO₄ and concentrated under reduced pressure. The residue was purified by flash column chromatography (silica gel, n-Hex:EtOAc=3:1) to obtain 6-bromo-8-chloro-3,4-dihydro-2H-benzo[b][1,4]oxazine (70.0 mg, 63%) as a white solid.

LC/MS ESI (+): 248 (M+1)
¹H-NMR (400 MHz, DMSO-d₆): δ 6.84 (s, 1H), 6.61 (s, 1H), 4.31-4.33 (m, 2H), 3.42-3.45 (m, 2H), 3.97 (brs, 1H)

(b) Synthesis of 8-chloro-6-(4-chlorophenoxy)-3,4-dihydro-2H-benzo[b][1,4]oxazine 6-Bromo-8-chloro-3,4-dihydro-2H-benzo[b][1,4]oxazine (60.0 mg, 0.24 mmol), 4-chlorophenol (62 mg, 0.48 mmol), CuI (23.0 mg, 0.12 mmol), N,N-dimethylglycine (24.9 mg, 0.24 mmol) and Cs₂CO₃ (236.0 mg, 0.72 mmol) were added to anhydrous 1,4-dioxane (2.4 mL). The reaction mixture was stirred at 120° C. for 15 hours, H₂O was added, and extracted with EtOAc. The organic extract was washed with brine, dried over anhydrous Na₂SO₄ and concentrated under reduced pressure. The residue was purified by flash column chromatography (amine silica gel, n-Hex:EtOAc=9:1) to obtain 8-chloro-6-(4-chlorophenoxy)-3,4-dihydro-2H-benzo[b][1,4]oxazine (42.0 mg, 42%).

LC/MS ESI (+): 296 (M+1)

(c) Synthesis of (8-chloro-6-(4-chlorophenoxy)-2,3-dihydro-4H-benzo[b][1,4]oxazin-4-yl)(5-(2-(methylsulfonyl)propan-2-yl)benzo[b]thiophen-2-yl)methanone The synthesis procedure of Example 1-h was repeated except for using 8-chloro-6-(4-chlorophenoxy)-3,4-dihydro-2H-benzo[b][1,4]oxazine (20.0 mg, 0.07 mmol) as a starting material to obtain (8-chloro-6-(4-chlorophenoxy)-2,3-dihydro-4H-benzo[b][1,4]oxazin-4-yl)(5-(2-(methylsulfonyl)propan-2-yl)benzo[b]thiophen-2-yl)methanone (13.0 mg, 33%) as a white solid.

LC/MS ESI (+): 576 (M+1)
¹H-NMR (400 MHz, DMSO-d₆): δ 8.20 (s, 1H), 8.07 (d, 1H, J=8.6 Hz), 7.88 (s, 1H), 7.75 (d, 1H, J=8.7 Hz), 7.02-7.09 (m, 4H), 6.79 (d, 2H, J=8.3 Hz), 4.46-4.51 (m, 2H), 4.10-4.16 (m, 2H), 2.74 (s, 3H), 1.84 (s, 6H)

Example 97) Synthesis of N-(3-chloro-5-(1-(4-chlorophenyl)cyclopropyl)phenyl)-5-(2-(methylsulfonyl)propan-2-yl)benzo[b]thiophene-2-carboxamide (a) Synthesis of (3-chloro-5-nitrophenyl)(4-chlorophenyl)methanone 3-Chloro-5-nitrobenzoic acid (2.0 g, 9.92 mmol) and DMF (0.1 mL, 0.99 mmol) was dissolved in SOCl₂ (3.6 mL, 49.60 mmol). The reaction mixture was stirred at 80° C. for 3 hours and concentrated under reduced pressure to obtain 3-chloro-5-nitrobenzoyl chloride. The residue was dissolved in chlorobenzene (20.0 mL), AlCl₃ (4.0 g, 29.80 mmol) was added at 0° C., and stirred at 50° C. for 5 hours. H₂O was added at 0° C., and the reaction mixture was extracted with EtOAc. The organic extract was washed with sat. NaHCO₃ aqueous solution and brine, dried over anhydrous Na₂SO₄ and concentrated under reduced pressure. The residue was purified by flash column chromatography (silica gel, n-Hex: DCM=4:1) to obtain (3-chloro-5-nitrophenyl)(4-chlorophenyl)methanone (2.8 g, 96%) as a yellow solid.

¹H-NMR (400 MHz, CDCl₃): δ 8.46 (m, 1H), 8.44 (m, 1H), 8.08 (m, 1H), 7.75 (d, 2H, J=8.5 Hz), 7.54 (d, 2H, J=8.5 Hz)

(b) Synthesis of 1-chloro-3-(1-(4-chlorophenyl)vinyl)-5-nitrobenzene

Bromo(methyl)triphenylphosphorane (5.3 g, 19.10 mmol) was dissolved in THF (25.0 mL), 1.6M solution of n-BuLi in n-Hex (12.0 mL, 19.10 mmol) was added dropwise at 0° C., and stirred for 30 minutes. The reaction mixture was slowly added to a solution of (3-chloro-5-nitrophenyl)(4-chlorophenyl)methanone (2.8 g, 9.56 mmol) in THF (8.0 mL) at 0° C. The reaction mixture was stirred at room temperature for 12 hours, H₂O was added, and extracted with EtOAc. The organic extract was washed with brine, dried over anhydrous Na₂SO₄ and concentrated under reduced pressure. The residue was purified by flash column chromatography (silica gel, n-Hex:DCM=4:1) to obtain 1-chloro-3-(1-(4-chlorophenyl)vinyl)-5-nitrobenzene (1.8 g, 65%) as a color solid.

¹H-NMR (400 MHz, CDCl₃): δ 8.18 (m, 1H), 8.07 (m, 1H), 7.61 (m, 1H), 7.36 (d, 2H, J=8.4 Hz), 7.22 (d, 2H, J=8.4 Hz), 5.63 (s, 1H), 5.60 (s, 1H)

(c) Synthesis of 1-chloro-3-(2,2-dibromo-1-(4-chlorophenyl)cyclopropyl)-5-nitrobenzene 1-Chloro-3-(1-(4-chlorophenyl)vinyl)-5-nitrobenzene (1.8 g, 6.19 mmol), CHBr₃ (735.0 μL, 8.42 mmol) and benzyl triethylammonium chloride (254.0 mg, 1.11 mmol) were dissolved in 1,2-dichloroethane (6.2 mL), and NaOH (9.4 g, 235.0 mmol) in H₂O (9.4 mL) was added. The reaction mixture was stirred at 40° C. for 16 hours, H₂O was added, and extracted with EtOAc. The organic extract was washed with brine, dried over anhydrous Na₂SO₄ and concentrated under reduced pressure. The residue was purified by flash column chromatography (silica gel, n-Hex:DCM=4:1) to obtain 1-chloro-3-(2,2-dibromo-1-(4-chlorophenyl)cyclopropyl)-5-nitrobenzene (2.2 g, 75%) as a yellow oil.

¹H-NMR (400 MHz, CDCl₃): δ 8.22 (s, 1H), 8.11 (s, 1H), 7.79 (s, 1H), 7.44 (d, 2H, J=8.4 Hz), 7.35 (d, 2H, J=8.4 Hz), 2.50-2.55 (m, 2H)

(d) Synthesis of 3-chloro-5-(1-(4-chlorophenyl)cyclopropyl)aniline

The synthesis procedure of Example 1-g was repeated except for using 1-chloro-3-(2,2-dibromo-1-(4-chlorophenyl)cyclopropyl)-5-nitrobenzene (2.2 g, 4.61 mmol) as a starting material to obtain 3-chloro-5-(1-(4-chlorophenyl)cyclopropyl)aniline (1.2 g, 95%) as a yellow oil.

LC/MS ESI (+): 278 (M+1)
¹H-NMR (400 MHz, CDCl₃): δ 7.24 (d, 2H, J=8.4 Hz), 7.15 (d, 2H, J=8.4 Hz), 6.56 (s, 1H), 6.50 (s, 1H), 6.35 (s, 1H), 3.66 (brs, 2H), 1.20-1.28 (m, 4H)

(e) Synthesis of N-(3-chloro-5-(1-(4-chlorophenyl)cyclopropyl)phenyl)-5-(2-(methyl sulfonyl)propan-2-yl)benzo[b]thiophene-2-carboxamide The synthesis procedure of Example 1-h was repeated except for using 3-chloro-5-(1-(4-chlorophenyl)cyclopropyl)aniline (46.7 mg, 0.17 mmol) as a starting material to obtain N-(3-chloro-5-(1-(4-chlorophenyl)cyclopropyl)phenyl)-5-(2-(methylsulfonyl)propan-2-yl)benzo[b]thiophene-2-carboxamide (44.1 mg, 47%).

LC/MS ESI (+): 558 (M+1)

$^1$H-NMR (400 MHz, DMSO-$d_6$): δ 10.64 (s, 1H), 8.34 (s, 1H), 8.20 (s, 1H), 8.10 (d, 1H, J=8.7 Hz), 7.84 (m, 1H), 7.74 (dd, 1H, J=8.7, 1.8 Hz), 7.54 (m, 1H), 7.38 (d, 2H, J=8.6 Hz), 7.29 (d, 2H, J=8.6 Hz), 7.02 (m, 1H), 2.73 (s, 3H), 1.85 (s, 6H), 1.30-1.32 (m, 4H)

Example 98) Synthesis of N-(3-chloro-5-((2,4-difluorophenyl)(methyl)amino)phenyl)-5-(2-(methylsulfonyl)propan-2-yl)benzo[b]thiophene-2-carboxamide (a) Synthesis of N-(3-chloro-5-nitrophenyl)-2,4-difluoroaniline 1-Bromo-3-chloro-5-nitrobenzene (100.0 mg, 0.42 mmol), 2,4-difluoroaniline (35.6 pt, 0.35 mmol), Pd$_2$(dba)$_3$.CHCl$_3$ (18.3 mg, 0.02 mmol), BINAP (21.9 mg, 0.04 mmol) and NaOt-Bu (47.5 mg, 0.49 mmol) were added to anhydrous toluene (3.5 mL). The reaction mixture was allowed to react at 110° C. for 30 minutes in a microwave at 150 W. The reaction mixture was cooled to room temperature, H$_2$O was added, and extracted with EtOAc. The organic extract was washed with brine, dried over anhydrous Na$_2$SO$_4$, and concentrated under reduced pressure. The residue was purified by flash column chromatography (silica gel, n-Hex:EtOAc=9:1) to obtain N-(3-chloro-5-nitrophenyl)-2,4-difluoroaniline (76.6 mg, 76%) as a yellow solid.

LC/MS ESI (+): 285 (M+1)

$^1$H-NMR (400 MHz, CDCl$_3$): δ 7.68 (s, 1H), 7.58 (s, 1H), 7.31 (m, 1H), 7.11 (s, 1H), 6.91-7.00 (m, 2H), 5.79 (s, 1H)

(b) Synthesis of N-(3-chloro-5-nitrophenyl)-2,4-difluoro-N-methylaniline

N-(3-chloro-5-nitrophenyl)-2,4-difluoroaniline (167.1 mg, 0.59 mmol) was dissolved in DMF (6.0 mL), and 60 wt % NaH (35.2 mg, 0.88 mmol) and CH$_3$I (73.1 μL, 1.17 mmol) were added at 0° C. The reaction mixture was stirred at room temperature for 1 hour, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain N-(3-chloro-5-nitrophenyl)-2,4-difluoro-N-methylaniline (172.4 mg, 98%) as a yellow solid.

$^1$H-NMR (400 MHz, CDCl$_3$): δ 7.58 (s, 1H), 7.34 (s, 1H), 7.27 (m, 1H), 6.97-7.02 (m, 2H), 6.82 (s, 1H), 3.31 (s, 3H)

(c) Synthesis of 5-chloro-N$^1$-(2,4-difluorophenyl)-N$^1$-methylbenzene-1,3-diamine The synthesis procedure of Example 1-g was repeated except for using N-(3-chloro-5-nitrophenyl)-2,4-difluoro-N-methylaniline (172.4 mg, 0.58 mmol) as a starting material to obtain 5-chloro-N$^1$ (2,4-difluorophenyl)-N$^1$-methylbenzene-1,3-diamine (148.4 mg, 96%) as a red oil.

$^1$H-NMR (400 MHz, CDCl$_3$): δ 7.22 (m, 1H), 6.87-6.94 (m, 2H), 6.14 (s, 1H), 6.06 (s, 1H), 5.79 (s, 1H), 3.60 (brs, 2H), 3.18 (s, 3H)

(d) Synthesis of N-(3-chloro-5-((2,4-difluorophenyl)(methyl)amino)phenyl)-5-(2-(methylsulfonyl)propan-2-yl)benzo[b]thiophene-2-carboxamide The synthesis procedure of Example 1-h was repeated except for using 5-chloro-N$^1$-(2,4-difluorophenyl)-N$^1$-methylbenzene-1,3-diamine (35.6 mg, 0.13 mmol) as a starting material to obtain N-(3-chloro-5-(2,4-difluorophenyl)(methyl)amino)phenyl)-5-(2-(methylsulfonyl)propan-2-yl)benzo[b]thiophene-2-carboxamide (57.2 mg, 79%) as a white solid.

LC/MS ESI (+): 549 (M+1)

$^1$H-NMR (400 MHz, DMSO-$d_6$): δ 10.45 (s, 1H), 8.31 (s, 1H), 8.19 (s, 1H), 8.08 (d, 1H, J=8.7 Hz), 7.73 (m, 1H), 7.41-7.53 (m, 3H), 7.21 (m, 1H), 6.93 (s, 1H), 6.48 (s, 1H), 3.23 (s, 3H), 2.72 (s, 3H), 1.84 (s, 6H)

Compounds from Example 99 and Example 100 were synthesized through the synthesis route of Example 98, data of these compounds are listed as follows.

TABLE 6

| Ex. | Compound | Analysis data |
|---|---|---|
| 99 | N-(3-chloro-5-((4-chlorophenyl)(methyl)amino)phenyl)-5-(2-(methylsulfonyl)propan-2-yl)benzo[b]thiophene-2-carboxamide | LC/MS ESI (+): 547 (M + 1)<br>$^1$H-NMR (400 MHz, DMSO-$d_6$):<br>δ 10.51 (s, 1H), 8.32 (s, 1H), 8.20 (s, 1H),<br>8.09 (d, 1H, J = 8.7 Hz), 7.74 (dd, 1H, J = 8.7, 1.4 Hz),<br>7.52 (s, 1H), 7.42 (d, 2H, J = 8.7 Hz), 7.25 (s, 1H), 7.19 (d, 2H, J = 8.7 Hz), 6.73 (s, 1H),<br>3.27 (s, 3H), 2.73 (s, 3H), 1.85 (s, 6H) |
| 100 | N-(2-chloro-6-((4-chlorophenyl)(methyl)amino)pyridin-4-yl)-5-(2-(methylsulfonyl)propan-2-yl)benzo[b]thiophene-2-carboxamide | LC/MS ESI (+): 548 (M + 1)<br>$^1$H-NMR (400 MHz, DMSO-$d_6$): δ 10.68 (s, 1H),<br>8.33 (s, 1H), 8.20 (d, 1H, J = 1.6 Hz), 8.09 (d, 1H, J = 8.7 Hz), 7.74 (dd, 1H, J = 8.7, 1.9 Hz),<br>7.55 (d, 2H, J = 8.7 Hz), 7.40 (d, 2H, J = 8.7 Hz),<br>7.33 (d, 1H, J = 1.3 Hz), 6.88 (d, 1H, J = 1.3 Hz),<br>3.36 (s, 3H), 2.73 (s, 3H), 1.84 (s, 6H) |

Example 101) Synthesis of N-(2-chloro-6-((4-chlorocyclohex-3-en-1-yl)oxy)pyridin-4-yl)-5-(2-(methylsulfonyl)propan-2-yl)benzo[b]thiophene-2-carboxamide (a) Synthesis of 4-amino-6-chloropyridin-2-ol 2,6-Dichloropyridine-4-amine (1.0 g, 6.13 mmol) was dissolved in tert-BuOH (30.7 mL) and KOH (516.0 mg, 9.20 mmol) was added. The reaction mixture was stirred at 150° C. for 15 hours, H$_2$O was added, and extracted with EtOAc. The aqueous layer was acidified with 1N HCl aqueous solution and then extracted with EtOAc. The organic extract was dried over anhydrous Na$_2$SO$_4$ and concentrated under reduced pressure. The residue was purified by flash column chromatography (silica gel, MeOH:EtOAc=1:10) to obtain 4-amino-6-chloropyridin-2-ol (120.0 mg, 14%) as an off-white solid.

LC/MS ESI (+): 145 (M+1)

(b) Synthesis of 4-chlorocyclohex-3-en-1-yl benzoate

4-Oxocyclohexyl benzoate (1.1 g, 4.76 mmol) was dissolved in toluene (55.0 mL) and $PCl_5$ (1.3 g, 6.05 mmol) was added at −40° C. The reaction mixture was stirred at room temperature for 2 hours, $H_2O$ was added, and extracted with EtOAc. The organic extract was dried over anhydrous $Na_2SO_4$ and concentrated under reduced pressure. The residue was purified by flash column chromatography (silica gel, n-Hex:EtOAc=1:4) to obtain 4-chlorocyclohex-3-en-1-yl benzoate (850.0 mg, 65%) as an off-white oil.

$^1$H-NMR (400 MHz, $CDCl_3$): δ 8.03 (d, 2H, J=8.0 Hz), 7.57 (t, 1H, J=7.6 Hz), 7.44 (t, 2H, J=7.6 Hz), 5.76 (m, 1H), 5.31 (m, 1H), 2.34-2.61 (m, 4H), 2.05-2.10 (m, 2H)

(c) Synthesis of 4-chlorocyclohex-3-en-1-ol

4-Chlorocyclohex-3-en-1-yl benzoate (400.0 mg, 1.69 mmol) was dissolved in MeOH (8.4 mL) and 0.5M solution of NaOMe in MeOH (3.8 mL, 1.86 mmol) was added at 0° C. The reaction mixture was stirred for 2 hours, $NaHSO_4$ and $NaH_2PO_4$ buffer solution were added, and extracted with $CH_2Cl_2$. The organic extract was dried over anhydrous $Na_2SO_4$ and concentrated under reduced pressure. The residue was purified by flash column chromatography (silica gel, n-Hex:EtOAc=1:1) to obtain 4-chlorocyclohex-3-en-1-ol (90.0 mg, 40%) as an off-white oil.

$^1$H-NMR (400 MHz, $CDCl_3$): δ 5.69 (m, 1H), 4.01 (m, 1H), 2.41-2.45 (m, 3H), 2.14 (m, 1H), 1.82-1.92 (m, 2H)

(d) Synthesis of 2-chloro-6-((4-chlorocyclohex-3-en-1-yl)oxy)pyridine-4-amine 4-Amino-6-chloropyridin-2-ol (80.0 mg, 0.55 mmol) was dissolved in THF (2.0 mL), and 2-4-chlorocyclohex-3-en-1-ol (81.0 mg, 0.61 mmol), 2.2M solution of DEAD in toluene (377.0 μL, 0.83 mmol) and $PPh_3$ (189.0 mg, 0.72 mmol) were added. The reaction mixture was stirred at room temperature for 15 hours and concentrated under reduced pressure. The residue was purified by flash column chromatography (silica gel, n-Hex:EtOAc=1:2) to obtain 2-chloro-6-((4-chlorocyclohex-3-en-1-yl)oxy)pyridine-4-amine (51.0 mg, 36%) as a yellow oil.

LC/MS ESI (+): 259 (M+1)

$^1$H-NMR (400 MHz, $CDCl_3$): δ 6.21 (s, 1H), 5.82 (s, 1H), 5.72 (m, 1H), 5.27 (m, 1H), 4.14 (s, 2H), 2.43-2.51 (m, 4H), 1.98-2.02 (m, 2H)

(e) Synthesis of N-(2-chloro-6-((4-chlorocyclohex-3-en-1-yl)oxy)pyridin-4-yl)-5-(2-(methylsulfonyl)propan-2-yl)benzo[b]thiophene-2-carboxamide The synthesis procedure of Example 67-b was repeated except for using 2-chloro-6-((4-chlorocyclohex-3-en-1-yl)oxy)pyridine-4-amine (40.0 mg, 0.15 mmol) as a starting material to obtain N-(2-chloro-6-((4-chlorocyclohex-3-en-1-yl)oxy)pyridin-4-yl)-5-(2-(methylsulfonyl)propan-2-yl)benzo[b]thiophene-2-carboxamide (35.0 mg, 42%).

LC/MS ESI (+): 539 (M+1)

$^1$H-NMR (400 MHz, DMSO-$d_6$): δ 10.96 (s, 1H), 8.40 (s, 1H), 8.26 (s, 1H), 8.13 (d, 1H, J=8.8 Hz), 7.78 (d, 1H, J=8.8 Hz), 7.46 (s, 1H), 7.24 (s, 1H), 5.81 (m, 1H), 5.21 (m, 1H), 2.75 (s, 3H), 2.43-2.68 (m, 4H), 2.01-2.03 (m, 2H)

Example 102) Synthesis of N-(2-chloro-6-((octahydroindolizin-7-yl)oxy)pyridin-4-yl)-5-(2-(methylsulfonyl)propan-2-yl)benzo[b]thiophene-2-carboxamide

(a) Synthesis of octahydroindolizin-7-ol

Hexahydroindolizin-7(1H)-one (220.0 mg, 1.58 mmol) was dissolved in THF (12.5 ml) and 1.0M $LiAlH_4$ in THF (3.95 ml, 3.95 mmol) was added thereto at room temperature. The mixture was stirred at 80° C. for 30 min. and water was added at 0° C. The resulting reaction mixture was filtered through Celite and extracted with $CH_2Cl_2$. The organic extract was washed with brine, dried over anhydrous $Na_2SO_4$, filtered and evaporated to obtain octahydroindolizin-7-ol (220.0 mg, 99%) as a colorless liquid.

LC/MS ESI (+): 142 (M+1)

$^1$H-NMR (400 MHz, DMSO-$d_6$): δ 4.63-4.64 (m, 1H), 2.86-2.93 (m, 2H), 1.86-1.97 (m, 3H), 1.56-1.79 (m, 5H), 1.25-1.40 (m, 2H), 0.98-1.07 (m, 1H)

(b) Synthesis of 2-chloro-6-((octahydroindolizin-7-yl)oxy)pyridin-4-amine

Octahydroindolizin-7-ol (200.0 mg, 1.42 mmol) and 2,6-dichloropyridin-4-amine (462.0 mg, 2.83 mmol) were dissolved in sulfolane (7.0 ml) and 60 wt % NaH (113.0 mg, 2.83 mmol) was added thereto at room temperature. The mixture was stirred at 160° C. for 1 hour and extracted with EtOAc. The organic extract was washed with brine, dried over anhydrous $Na_2SO_4$, filtered and concentrated under a reduced pressure. The residue was purified by reversed-phase column chromatography (C18-silica gel, 0.1% formic acid in $CH_3CN$:0.1% formic acid in $H_2O$) to obtain 2-chloro-6-((octahydroindolizin-7-yl)oxy)pyridin-4-amine (200.0 mg, 52%) as a colorless liquid.

LC/MS ESI (+): 268 (M+1)

$^1$H-NMR (400 MHz, DMSO-$d_6$): δ 6.28 (s, 2H), 6.18 (d, 1H, J=1.6 Hz), 5.74-5.76 (m, 1H), 4.72-4.80 (m, 1H), 2.89-3.01 (m, 2H), 2.12-2.16 (m, 1H), 1.86-2.06 (m, 4H), 1.62-1.83 (m, 3H), 1.47-1.56 (m, 1H), 1.27-1.37 (m, 1H), 1.15-1.27 (m, 1H)

(c) Synthesis of N-(2-chloro-6-((octahydroindolizin-7-yl)oxy)pyridin-4-yl)-5-(2-(methylsulfonyl)propan-2-yl)benzo[b]thiophene-2-carboxamide The synthesis procedure of Example 62-b was repeated except for using 2-chloro-6-((octahydroindolizin-7-yl)oxy)pyridin-4-amine (50.0 mg, 0.19 mmol) as a starting material to obtain N-(2-chloro-6-((octahydroindolizin-7-yl)oxy)pyridin-4-yl)-5-(2-(methylsulfonyl)propan-2-yl)benzo[b]thiophene-2-carboxamide (11.1 mg, 10%)

LC/MS ESI (+): 548 (M+1)

$^1$H-NMR (400 MHz, DMSO-$d_6$): δ 10.95 (s, 1H), 8.40 (s, 1H), 8.26 (d, 1H, J=1.6 Hz), 8.12-8.16 (m, 1H), 7.78 (dd, 1H, J=8.8, 1.6 Hz), 7.45 (d, 1H, J=1.6 Hz), 7.20 (d, 1H, J=1.2 Hz), 4.88-4.94 (m, 1H), 2.94-3.08 (m, 2H), 2.75 (s, 3H), 2.22-2.26 (m, 1H), 1.95-1.96 (m, 4H), 1.79-1.90 (m, 6H), 1.60-1.76 (m, 3H), 1.23-1.42 (m, 3H)

Example 103) Synthesis of N-(3-chloro-5-(4-chlorophenoxy)phenyl)-5-(2-(methylsulfonyl)propan-2-yl)benzo[b]thiophene-2-carboximidamide 2,2,2-trifluoroacetate

(a) Synthesis of 5-(2-(methylsulfonyl)propan-2-yl)benzo[b]thiophene-2-carboxamide 5-(2-(Methylsulfonyl)propan-2-yl)benzo[b]thiophene-2-carboxylic acid (111.0 mg, 0.37 mmol) was dissolved in CH₂Cl₂ (3.6 mL), and (COCl)₂ (50.8 mg, 0.40 mmol) and DMF (cat.) were added dropwise. The reaction mixture was stirred at room temperature for 1 hour and concentrated under reduced pressure to obtain 5-(2-(methylsulfonyl)propan-2-yl)benzo[b]thiophene-2-carbonyl chloride. The residue was dissolved in 1,4-dioxane (3.7 mL), and 2N solution of NH₃ in MeOH (1.8 mL) was added dropwise. The reaction mixture was stirred at room temperature for 40 minutes, concentrated under reduced pressure. The residue was purified by reversed-phase chromatography (C18-silica gel, CH₃CN:H₂O) to obtain 5-(2-(methylsulfonyl)propan-2-yl)benzo[b]thiophene-2-carboxamide (110.0 mg, quant).

LC/MS ESI (+): 298 (M+1)

¹H-NMR (400 MHz, DMSO-d₆): δ 8.26 (brs, 1H), 8.11 (d, 1H, J=1.7 Hz), 8.08 (s, 1H), 8.04 (d, 1H, J=8.7 Hz), 7.70 (dd, 1H, J=8.7, 2.0 Hz), 7.66 (brs, 1H), 2.71 (s, 3H), 1.83 (s, 6H)

(b) Synthesis of ethyl 5-(2-(methylsulfonyl)propan-2-yl)benzo[b]thiophene-2-carbimidate 5-(2-(Methylsulfonyl)propan-2-yl)benzo[b]thiophene-2-carboxamide (85.0 mg, 0.29 mmol) was dissolved in CH₂Cl₂ (6.0 mL) and 1.0M solution of triethyloxonium tetrafluoroborate in CH₂Cl₂ (109.0 mL, 0.57 mmol) was added dropwise. The reaction mixture was stirred at room temperature for 16 hours, and extracted with CH₂Cl₂. The organic extract was washed with brine, dried over anhydrous Na₂SO₄ and concentrated under reduced pressure. The residue was purified by flash column chromatography (amine silica gel, CH₂Cl₂: MeOH=9:1) to obtain ethyl 5-(2-(methylsulfonyl)propan-2-yl)benzo[b]thiophene-2-carbimidate (63.9 mg, 69%).

LC/MS ESI (+): 326 (M+1)

¹H-NMR (400 MHz, DMSO-d₆): δ 9.15 (s, 1H), 8.17 (s, 1H), 8.12 (d, 1H, J=1.5 Hz), 8.03 (d, 1H, J=8.7 Hz), 7.70 (dd, 1H, J=8.9, 1.8 Hz), 4.27 (q, 2H, J=7.1 Hz), 2.72 (s, 3H), 1.83 (s, 6H), 1.33 (t, 3H, J=7.1 Hz)

(c) Synthesis of N-(3-chloro-5-(4-chlorophenoxy)phenyl)-5-(2-(methylsulfonyl)propan-2-yl)benzo[b]thiophene-2-carboximidamide 2,2,2-trifluoroacetate Ethyl 5-(2-(methylsulfonyl)propan-2-yl)benzo[b]thiophene-2-carbimidate (63.9 mg, 0.20 mmol) and 3-chloro-5-(4-chlorophenoxy)aniline (59.9 mg, 0.24 mmol) were dissolved in DMF (0.4 mL) and triethylamine (19.9 mg, 0.20 mmol) was added dropwise. The reaction mixture was stirred at 60° C. for 16 hours and then at 100° C. for 16 hours. The reaction mixture was purified by reversed-phase column chromatography (C18-silica gel, 0.1% formic acid in CH₃CN:0.1% formic acid in H₂O) to obtain N-(3-chloro-5-(4-chlorophenoxy)phenyl)-5-(2-(methylsulfonyl)propan-2-yl)benzo[b]thiophene-2-carboximidamide 2,2,2-trifluoroacetate (2.4 mg, 2%) as white solid.

LC/MS ESI (+): 533 (M+1), Free form

¹H-NMR (400 MHz, DMSO-d₆): δ 11.79 (brs, 2H), 8.31 (s, 1H), 8.26 (s, 1H), 8.18 (d, 1H, J=7.3 Hz), 7.80 (d, 1H, J=8.6 Hz), 7.49 (d, 2H, J=7.7 Hz), 7.26 (brs, 1H), 7.18 (d, 2H, J=8.4 Hz), 7.14 (brs, 1H), 6.96 (brs, 1H), 2.75 (s, 3H), 1.86 (s, 6H)

Example 104) Synthesis of N-(2-chloro-6-(hexahydropyrrolo[1,2-a]pyrazin-2(1H)-yl)pyridin-4-yl)-5-(2-(methylsulfonyl)propan-2-yl)benzo[b]thiophene-2-carboxamide (a) Synthesis of 2-chloro-6-(hexahydropyrrolo[1,2-a]pyrazin-2(1H)-yl)pyridin-4-amine 2,6-dichloropyridin-4-amine (50.0 mg, 0.31 mmol) and octahydropyrrolo[1,2-a]pyrazine (77.6 mg, 0.61 mmol) were dissolved in sulfolane (0.5 mL), followed by heating at 150° C. for overnight. Octahydropyrrolo[1,2-c]pyrazine (100.0 mg, 0.80 mmol) was more added. The reaction mixture was stirred at 150° C. for 1 day additionally and then cooled to room temperature and extracted with EtOAc. The organic extract was washed with brine, dried over anhydrous Na₂SO₄, concentrated under reduced pressure. The residue was purified by flash column chromatography (silica gel, CH₂Cl₂:MeOH=7:1) to obtain 2-chloro-6-(hexahydropyrrolo[1,2-c]pyrazin-2(1H)-yl)pyridin-4-amine (66.0 mg, 85%) as a light-yellow amorphous.

¹H-NMR (400 MHz, CDCl₃): δ 6.00 (s, 1H), 5.71 (s, 1H) 4.31 (d, 1H, J=11.9 Hz), 4.07 (d, 1H, J=12.2 Hz), 4.02 (s, 2H), 3.11-3.15 (m, 2H), 2.94-3.01 (m, 1H), 2.57-2.63 (m, 1H), 2.28-2.31 (m, 1H), 2.15-2.19 (m, 1H), 2.03-2.08 (m, 2H), 1.77-1.83 (m, 2H), 1.47-1.50 (m, 1H)

(b) Synthesis of N-(2-chloro-6-(hexahydropyrrolo[1,2-a]pyrazin-2(1H)-yl)pyridin-4-yl)-5-(2-(methylsulfonyl)propan-2-yl)benzo[b]thiophene-2-carboxamide The synthesis procedure of Example 62-b was repeated except for using 2-chloro-6-(hexahydropyrrolo[1,2-a]pyrazin-2(1H)-yl)pyridin-4-amine (62.0 mg, 0.25 mmol) to obtain N-(2-chloro-6-(hexahydropyrrolo[1,2-c]pyrazin-2(1H)-yl)pyridin-4-yl)-5-(2-(methylsulfonyl)propan-2-yl)benzo[b]thiophene-2-carboxamide (28.4 mg, 22%).

LC/MS ESI (+): 533 (M+1)

¹H-NMR (400 MHz, DMSO-d₆): δ 10.73 (s, 1H), 8.39 (s, 1H), 8.22 (m, 1H), 8.12 (d, 1H, J=8.7 Hz), 7.76 (dd, 1H, J=8.7, 1.8 Hz), 7.22 (s, 1H), 7.13 (s, 1H), 4.23 (d, 1H, J=11.1 Hz), 4.08 (d, 1H, J=12.4 Hz), 3.00-3.09 (m, 2H), 2.87-2.94 (m, 1H), 2.74 (s, 3H), 2.55-2.60 (m, 1H), 2.03-2.16 (m, 2H), 1.86-1.97 (m, 8H), 1.66-1.76 (m, 2H), 1.33-1.43 (m, 1H)

Compounds from Example 105 and Example 108 were synthesized through the synthesis route of Example 104, data of these compounds are listed as follows.

TABLE 7

| Ex. | Compound | Analysis data |
|---|---|---|
| 105 | N-(2-(4-(tert-butyl)piperidin-1-yl)-6-chloropyridin-4-yl)-5-(2-(methylsulfonyl)propan-2-yl)benzo[b]thiophene-2-carboxamide | LC/MS ESI (+): 548 (M + 1)<br>¹H-NMR (400 MHz, DMSO-d₆):<br>10.71 (s, 1H), 8.38 (s, 1H), 8.22 (m, 1H),<br>8.11 (d, 1H, J = 8.8 Hz), 7.76 (dd, 1H,<br>J = 8.8, 2.0 Hz), 7.17 (s, 1H), 7.09 (s, 1H),<br>4.24 (d, 2H, J = 12.8 Hz), 2.74-2.79 (m,<br>5H), 1.85 (s, 6H), 1.74 (d, 2H, J = 11.2 Hz),<br>1.14-1.26 (m, 3H), 0.85 (s, 9H) |
| 106 | N-(2-chloro-6-(octahydro-2H-pyrido[1,2-a]pyrazin-2-yl)pyridin-4-yl)-5-(2-(methylsulfonyl)propan- | LC/MS ESI (+): 547 (M + 1)<br>¹H-NMR (400 MHz, DMSO-d₆):<br>10.74 (s, 1H), 8.39 (s, 1H), 8.22 (s, 1H), |

TABLE 7-continued

| Ex. | Compound | Analysis data |
|---|---|---|
| | 2-yl)benzo[b]thiophene-2-carboxamide | 8.12 (d, 1H, J = 8.8 Hz), 7.76 (dd, 1H, J = 8.8, 1.6 Hz), 7.16 (d, 1H, J = 8.8 Hz), 4.04 (d, 1H, J = 12.4 Hz), 3.92 (d, 1H, J = 11.6 Hz), 2.88-2.94 (m, 1H), 2.81 (dd, 2H, J = 5.6, 0.8 Hz), 2.74 (s, 3H), 2.54-2.57 (m, 1H), 2.12-2.13 (m, 1H), 1.85-1.89 (m, 8H), 1.71-1.77 (m, 1H), 1.59-1.62 (m, 2H), 1.45-1.55 (m, 1H), 1.25-1.30 (m, 3H) |
| 107 | N-(2-chloro-6-(7-ethyl-2,7-diazaspiro[4.4]nonan-2-yl)pyridin-4-yl)-5-(2-(methylsulfonyl)propan-2-yl)benzo[b]thiophene-2-carboxamide | LC/MS ESI (+): 561 (M + 1)<br>$^1$H-NMR (400 MHz, DMSO-$d_6$): 10.70 (s, 1H), 8.39 (s, 1H), 8.22 (m, 1H), 8.12 (d, 1H, J = 8.7 Hz), 7.76 (dd, 1H, J = 8.7, 1.9 Hz), 7.02 (m, 1H), 6.90 (m, 1H), 3.36-3.41 (m, 4H), 3.26-3.31 (m, 2H), 2.74 (s, 3H), 2.60-2.67 (m, 1H), 2.39-2.45 (m, 3H), 1.90-2.02 (m, 2H), 1.86 (s, 6H), 1.74-1.79 (m, 2H), 1.02 (t, 3H, J = 7.2 Hz) |
| 108 | N-(2-chloro-6-(octahydroisoquinolin-2(1H)-yl)pyridin-4-yl)-5-(2-(methylsulfonyl)propan-2-yl)benzo[b]thiophene-2-carboxamide | LC/MS ESI (+): 546 (M + 1)<br>$^1$H-NMR (400 MHz, DMSO-$d_6$): 10.70 (s, 1H), 8.40 (s, 1H), 8.23 (m, 1H), 8.13 (d, 1H, J = 8.7 Hz), 7.78 (dd, 1H, J = 8.7, 1.9 Hz), 7.16 (s, 1H), 7.13 (s, 1H), 4.24 (d, 1H, J = 12.4 Hz), 4.04 (d, 1H, J = 12.4 Hz), 2.81-2.87 (m, 1H), 2.75 (s, 3H), 1.87 (s, 6H), 1.70-1.75 (m, 2H), 1.62-1.66 (m, 2H), 1.22-1.31 (m, 3H), 1.10-1.21 (m, 3H), 0.97-1.04 (m, 3H) |

Example 109) Synthesis of N-(2-chloro-6-((5-methylthiazol-2-yl)oxy)pyridin-4-yl)-5-(2-(methylsulfonyl)propan-2-yl)benzo[b]thiophene-2-carboxamide (a) Synthesis of 4-bromo-2,6-dichloropyridine 1-oxide 4-Bromo-2,6-dichloropyridine (5.0 g, 22.04 mmol) was dissolved in TFA (23.8 ml, 309.00 mmol) and $H_2O_2$ (4.8 ml, 55.10 mmol) was added at room temperature. The mixture was refluxed with stirring at 100° C. for 14 hours, followed by cooling to room temperature and filtered. Filtrate was extracted with EtOAc. The organic extract was washed with 1N NaOH, dried with anhydrous $Na_2SO_4$, filtered and evaporated to obtain 4-bromo-2,6-dichloropyridine 1-oxide (2.7 g, 49%) as a yellow solid.

LC/MS ESI (+): 244 (M+1)
$^1$H-NMR (400 MHz, CDCl$_3$): δ 7.61 (s, 2H)

(b) Synthesis of 4-bromo-2-chloro-6-((5-methylthiazol-2-yl)oxy)pyridine 1-oxide

4-Bromo-2,6-dichloropyridine 1-oxide (112.0 mg, 0.46 mmol) was dissolved in DMF (4.0 ml) and 5-methylthiazol-2-ol (53.0 mg, 0.46 mmol), $Cs_2CO_3$ (300.0 mg, 0.92 mmol) were added at room temperature. The mixture was stirred at 40° C. for 2 hours. The reaction mixture was purified by reversed-phase column chromatography (C18-silica gel, 0.1% formic acid in $CH_3CN$:0.1% formic acid in $H_2O$) to obtain 4-bromo-2-chloro-6-((5-methylthiazol-2-yl)oxy)pyridine 1-oxide (50.0 mg, 33%) as a yellow solid.

LC/MS ESI (+): 321 (M+1)
$^1$H-NMR (400 MHz, CDCl$_3$): δ 7.72 (d, 1H, J=2.8 Hz), 7.67 (d, 1H, J=2.8 Hz), 6.77-6.78 (m, 1H), 2.02 (d, 3H, J=1.6 Hz)

(c) Synthesis of 2-((4-bromo-6-chloropyridin-2-yl)oxy)-5-methylthiazole

4-Bromo-2-chloro-6-((5-methylthiazol-2-yl)oxy)pyridine 1-oxide (40.0 mg, 0.12 mmol) was dissolved in CHCl$_3$ (1.2 ml) and PCl$_3$ (33.0 μl, 0.37 mmol) was added thereto at 0° C. The mixture was stirred at room temperature for 6 hours and extracted with EtOAc. The organic extract was washed with 1N NaOH and brine, dried over anhydrous $Na_2SO_4$, filtered and evaporated to obtain 2-((4-bromo-6-chloropyridin-2-yl)oxy)-5-methylthiazole (35.0 mg, 92%) as an ivory solid.

LC/MS ESI (+): 305 (M+1)
$^1$H-NMR (400 MHz, CDCl$_3$): δ 8.48 (s, 1H), 7.40 (s, 1H), 7.37 (s, 1H), 2.21 (s, 3H)

(d) Synthesis of 2-chloro-6-((5-methylthiazol-2-yl)oxy)pyridin-4-amine 2-((4-Bromo-6-chloropyridin-2-yl)oxy)-5-methylthiazole (30.0 mg, 0.10 mmol) was dissolved in DMSO (1.0 ml) and Cu$_2$O (16.9 mg, 0.12 mmol), sodium azide (12.8 mg, 0.20 mmol) were added at room temperature. The mixture was stirred at 100° C. for 1 hour and extracted with EtOAc. The organic extract was washed with brine, dried over anhydrous $Na_2SO_4$, filtered and concentrated under a reduced pressure. The residue was purified by reversed-phase column chromatography (C18-silica gel, 0.1% formic acid in $CH_3CN$: 0.1% formic acid in $H_2O$) to obtain 2-chloro-6-((5-methylthiazol-2-yl)oxy)pyridin-4-amine (4.0 mg, 16%) as an off-white solid.

LC/MS ESI (+): 242 (M+1)
$^1$H-NMR (400 MHz, CDCl$_3$): δ 7.48 (d, 1H, J=1.6 Hz), 7.38 (d, 1H, J=1.2 Hz), 6.42 (d, 1H, J=1.6 Hz), 6.44 (brs, 2H), 2.18 (d, 3H, J=1.2 Hz)

(e) Synthesis of N-(2-chloro-6-((5-methylthiazol-2-yl)oxy)pyridin-4-yl)-5-(2-(methylsulfonyl)propan-2-yl)benzo[b]thiophene-2-carboxamide The synthesis procedure of Example 62-b was repeated except for using 2-chloro-6-((5-methylthiazol-2-yl)oxy)pyridin-4-amine (4.0 mg, 0.02 mmol) to obtain N-(2-chloro- 6-((5-methylthiazol-2-yl)oxy)pyridin-4-yl)-5-(2-(methylsulfonyl)propan-2-yl)benzo[b]thiophene-2-carboxamide (1.1 mg, 13%) as a white solid.

LC/MS ESI (+): 522 (M+1)

$^1$H-NMR (400 MHz, DMSO-d$_6$): δ 11.33 (brs, 1H), 8.49 (s, 2H), 8.24 (s, 1H), 8.12 (d, 1H, J=8.8 Hz), 8.00 (d, 1H, J=1.2 Hz), 7.77 (dd, 1H, J=8.8, 1.6 Hz), 7.48 (d, 1H, J=1.2 Hz), 2.74 (s, 3H), 2.22 (d, 3H, J=0.8 Hz), 1.86 (s, 6H)

Compounds from Example 110 and Example 121 were synthesized through the synthesis route of Example 109, data of these compounds are listed as follows.

TABLE 8

| Ex. | Compound | Analysis data |
| --- | --- | --- |
| 110 | N-(2-chloro-6-((1-methyl-1H-pyrazol-5-yl)oxy)pyridin-4-yl)-5-(2-(methylsulfonyl)propan-2-yl)benzo[b]thiophene-2-carboxamide | LC/MS ESI (+): 505 (M + 1)<br>$^1$H-NMR (400 MHz, DMSO-d$_6$):<br>δ 11.18 (brs, 1H), 8.42 (s, 1H), 8.26 (s, 1H), 8.13 (d, 1H, J = 8.7 Hz), 7.78 (dd, 1H, J = 8.7, 1.9 Hz), 7.72 (d, 1H, J = 1.4 Hz), 7.49 (d, 1H, J = 1.4 Hz), 7.45 (d, 1H, J = 2.0 Hz), 6.09 (d, 1H, J = 2.0 Hz), 3.65 (s, 3H), 2.74 (s, 3H), 1.86 (s, 6H) |
| 111 | N-(2-chloro-6-((1,3,5-trimethyl-1H-pyrazol-4-yl)oxy)pyridin-4-yl)-5-(2-(methylsulfonyl)propan-2-yl)benzo[b]thiophene-2-carboxamide | LC/MS ESI (+): 533 (M + 1)<br>$^1$H-NMR (400 MHz, DMSO-d$_6$):<br>δ 11.05 (brs, 1H), 8.40 (s, 1H), 8.25 (s, 1H), 8.13 (d, 1H, J = 8.6 Hz), 7.78 (d, 1H, J = 8.6 Hz), 7.67 (s, 1H), 7.22 (s, 1H), 3.69 (s, 3H), 2.74 (s, 3H), 2.09 (s, 3H), 1.96 (s, 3H), 1.86 (s, 6H) |
| 112 | N-(2-chloro-6-((1-methyl-1H-pyrazol-4-yl)oxy)pyridin-4-yl)-5-(2-(methylsulfonyl)propan-2-yl)benzo[b]thiophene-2-carboxamide | LC/MS ESI (+): 505 (M + 1)<br>$^1$H-NMR (400 MHz, DMSO-d$_6$):<br>δ 11.08 (brs, 1H), 8.41 (s, 1H), 8.25 (d, 1H, J = 1.6 Hz), 8.13 (d, 1H, J = 8.8 Hz), 7.89 (s, 1H), 7.78 (dd, 1H, J = 8.8, 2.0 Hz), 7.66 (d, 1H, J = 1.2 Hz), 7.49 (s, 1H), 7.33 (d, 1H, J = 0.8 Hz) 3.86 (s, 3H), 2.75 (s, 3H), 1.86 (s, 6H) |
| 113 | N-(2-chloro-6-((3,5-dimethylisoxazol-4-yl)oxy)pyridin-4-yl)-5-(2-(methylsulfonyl)propan-2-yl)benzo[b]thiophene-2-carboxamide | LC/MS ESI (+): 520 (M + 1)<br>$^1$H-NMR (400 MHz, DMSO-d$_6$):<br>δ 11.15 (brs, 1H), 8.42 (s, 1H), 8.27 (s, 1H), 8.15 (d, 1H, J = 8.7 Hz), 7.80 (d, 1H, J = 8.7 Hz), 7.68 (s, 1H), 7.47 (s, 1H), 2.75 (s, 3H), 2.32 (s, 3H), 2.10 (s, 3H), 1.87 (s, 6H) |
| 114 | N-(2-chloro-6-((5-methylthiophen-3-yl)oxy)pyridin-4-yl)-5-(2-(methylsulfonyl)propan-2-yl)benzo[b]thiophene-2-carboxamide | LC/MS ESI (+): 521 (M + 1)<br>$^1$H-NMR (400 MHz, DMSO-d$_6$):<br>δ 11.10 (brs, 1H), 8.42 (s, 1H), 8.26 (s, 1H), 8.13 (d, 1H, J = 8.7 Hz), 7.78 (d, 1H, J = 8.7 Hz), 7.69 (s, 1H), 7.31 (s, 1H), 7.06 (s, 1H), 6.78 (s, 1H), 2.75 (s, 3H), 2.46 (s, 3H), 1.86 (s, 6H) |
| 115 | N-(2-chloro-6-((2-methylthiophen-3-yl)oxy)pyridin-4-yl)-5-(2-(methylsulfonyl)propan-2-yl)benzo[b]thiophene-2-carboxamide | LC/MS ESI (+): 521 (M + 1)<br>$^1$H-NMR (400 MHz, DMSO-d$_6$):<br>δ 11.08 (brs, 1H), 8.41 (s, 1H), 8.26 (s, 1H), 8.14 (d, 1H, J = 8.7 Hz), 7.79 (d, 1H, J = 8.7 Hz), 7.65 (s, 1H), 7.40 (d, 1H, J = 5.4 Hz), 7.27 (s, 1H), 6.93 (d, 1H, J = 5.4 Hz), 2.75 (s, 3H), 2.24 (s, 3H), 1.86 (s, 6H) |
| 116 | N-(2-chloro-6-((4,5-dimethylisoxazol-3-yl)oxy)pyridin-4-yl)-5-(2-(methylsulfonyl)propan-2-yl)benzo[b]thiophene-2-carboxamide | LC/MS ESI (+): 520 (M + 1)<br>$^1$H-NMR (400 MHz, DMSO-d$_6$):<br>δ 11.21 (brs, 1H), 8.43 (s, 1H), 8.27 (s, 1H), 8.14 (d, 1H, J = 8.7 Hz), 7.80 (d, 1H, J = 8.7 Hz), 7.75 (s, 1H), 7.59 (s, 1H), 2.75 (s, 3H), 2.39 (s, 3H), 1.87 (s, 6H), 1.76 (s, 3H) |
| 117 | N-(2-chloro-6-((5-(trifluoromethyl)thiophen-3-yl)oxy)pyridin-4-yl)-5-(2-(methylsulfonyl)propan-2-yl)benzo[b]thiophene-2-carboxamide | LC/MS ESI (+): 575 (M + 1)<br>$^1$H-NMR (400 MHz, DMSO-d$_6$):<br>δ 11.14 (brs, 1H), 8.41 (s, 1H), 8.27 (s, 1H), 8.14 (d, 1H, J = 8.7 Hz), 7.81 (m, 2H), 7.77 (s, 1H), 7.70 (s, 1H), 7.40 (s, 1H), 2.75 (s, 3H), 1.87 (s, 6H) |
| 118 | methyl 3-((6-chloro-4-(5-(2-(methylsulfonyl)propan-2-yl)benzo[b]thiophene-2-carboxamido)pyridin-2-yl)oxy)isoxazole-5-carboxylate | LC/MS ESI (+): 550 (M + 1)<br>$^1$H-NMR (400 MHz, DMSO-d$_6$):<br>δ 11.20 (brs, 1H), 8.36 (s, 1H), 8.20 (s, 1H), 8.07 (d, 1H, J = 9.2 Hz), 7.71 (brs, 2H), 7.55 (s, 1H), 7.42 (s, 1H), 3.85 (s, 3H), 2.68 (s, 3H), 1.79 (s, 6H) |
| 119 | N-(2-chloro-6-((4-methylthiazol-2-yl)oxy)pyridin-4-yl)-5-(2-(methylsulfonyl)propan-2-yl)benzo[b]thiophene-2-carboxamide | LC/MS ESI (+): 522 (M + 1)<br>$^1$H-NMR (400 MHz, DMSO-d$_6$):<br>δ 11.63 (brs, 1H), 11.08 (brs, 1H), 8.43 (s, 1H), 8.27 (d, 1H, J = 1.6 Hz), 8.14 (d, 1H, J = 8.8 Hz), 7.85 (s, 1H), 7.77-7.80 (m, 2H), 2.76 (s, 3H), 2.44 (s, 3H), 1.87 (s, 6H) |

TABLE 8-continued

| Ex. | Compound | Analysis data |
|---|---|---|
| 120 | N-(2-chloro-6-((5-methylthiophen-2-yl)oxy)pyridin-4-yl)-5-(2-(methylsulfonyl)propan-2-yl)benzo[b]thiophene-2-carboxamide | LC/MS ESI (+): 304 (M + 1), 521 (M+3) $^1$H-NMR (400 MHz, CDCl$_3$): δ 11.16 (s, 1H), 8.41 (s, 1H), 8.25 (s, 1H), 8.12 (d, 1H, J = 9.7 Hz), 7.77 (d, 1H, J = 8.2 Hz), 7.71 (s, 1H), 7.42 (s, 1H), 6.64 (s, 2H), 2.74 (s, 3H), 2.41 (s, 3H), 1.85 (s, 6H) |
| 121 | N-(2-chloro-6-((2-chlorothiophen-3-yl)oxy)pyridin-4-yl)-5-(2-(methylsulfonyl)propan-2-yl)benzo[b]thiophene-2-carboxamide | LC/MS ESI (+): 540 (M + 1) $^1$H-NMR (400 MHz, DMSO-d$_6$): δ 11.20 (brs, 1H), 8.42 (s, 1H), 8.27 (s, 1H), 8.13 (d, 1H, J = 8.4 Hz), 7.80 (d, 1H, J = 9.6 Hz), 7.69 (s, 1H), 7.59 (d, 1H, J = 5.2 Hz), 7.39 (s, 1H), 7.09 (d, 1H, J = 6.0 Hz), 2.74 (s, 3H), 1.86 (s, 6H) |

EXPERIMENTAL EXAMPLES

Experiments were performed as shown below for the compounds prepared in Examples above.

Experimental Example 1) Experiment on the Inhibition of Stat3 and Stat1 activities via reporter gene assay 1-1) Experiment on the Inhibition of STAT3 Activity A human prostate cancer cell line (LNCaP stable cell line; plasmid pSTAT3-TA-luc), which contains a stably operating STAT3 promoter, was cultured in RPMI1640 medium (Cat No. 11875, Life Technologies) containing 10% fetal bovine serum (FBS) (Cat No. SH30396, Thermo Scientific) and 150 μg/mL G-418 solution (Cat No. 04 727 894 001, Roche). The reporter gene assay using LNCaP stable cell line was performed in RPMI1640 medium containing 3% DCC-FBS without G-418 solution. LNCaP stable cells were plated in two (2) white 96-well plates with 30,000 cells/50 μL in each well. The cells were cultured at 37° C., under 5% CO$_2$ for 24 hours, and then treated with the compounds listed in Examples which were diluted in various concentrations. Subsequently, IL-6 was added to each well with a final concentration of 10 ng/mL. Upon completion of the treatment with the compounds and IL-6, the cells were cultured at 37° C., under 5% CO$_2$ for 24 hours. The plates were observed under microscope and drug precipitation and particular findings were investigated and recorded.

The luciferase assay and the cell viability assay were performed respectively with one of the two plates. For the luciferase assay, the liquid media in the 96-well plate was removed, and then, 20 μL, of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 μL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

1-2) Experiment on the Inhibition of STAT1 Activity

A human osteosarcoma cell line (U2OS stable cell line; pGL4-STAT1-TA-luc), which contains a stably operating STAT1 promoter, was cultured in McCoy 5'A medium (Cat No. 16600, Life Technologies) containing 10% FBS (Cat No. SH30396, Thermo Scientific) and 1000 μg/mL G418 solution (Cat No. 04 727 894 001, Roche). The reporter gene assay using U2OS stable cell line was performed in McCoy 5'A medium containing 10% FBS without G-418 solution. U2OS stable cells were plated in two (2) white 96-well plates with 25,000 cells/50 pt in each well. The cells were cultured at 37° C., under 5% CO$_2$ for 24 hours, and then treated with the compounds listed in Examples which were diluted in various concentrations. Subsequently, IFN-γ was added to each well with a final concentration of 50 ng/mL. Upon completion of the treatment with the compounds and IFN-γ, the cells were cultured at 37° C., under 5% CO$_2$ for 8 hours. The plates were observed under microscope and drug precipitation and particular findings were investigated and recorded.

The luciferase assay and the cell viability assay were performed respectively with one of two plates. For the luciferase assay, the liquid media in the 96-well plate was removed, and then, 20 μL of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 μL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

The results of evaluation on the inhibitory effect of the compounds listed in the Examples on the dimerization of STAT3 and STAT1 obtained via the STAT3 and STAT1 reporter gene assays are shown in Table 9 below.

TABLE 9

| Ex. | IC$_{50}$ (μM) pSTAT3 | IC$_{50}$ (μM) pSTAT1 | Ex. | IC$_{50}$ (μM) pSTAT3 | IC$_{50}$ (μM) pSTAT1 |
|---|---|---|---|---|---|
| 1 | 0.0076 | >50 | 2 | 0.008 | >50 |
| 3 | 0.0098 | >50 | 4 | 0.0091 | >50 |
| 5 | 0.028 | >50 | 6 | 0.019 | >50 |
| 7 | 0.0088 | >50 | 8 | 0.061 | >50 |
| 9 | 0.00065 | >50 | 10 | 0.018 | >50 |
| 11 | 0.0021 | >50 | 12 | 0.0020 | >50 |
| 13 | 0.01 | >50 | 14 | 0.0083 | >50 |
| 15 | 0.0057 | >50 | 16 | 0.0057 | >50 |
| 17 | 0.045 | >50 | 18 | 0.031 | >50 |

TABLE 9-continued

| Ex. | IC$_{50}$ (μM) pSTAT3 | IC$_{50}$ (μM) pSTAT1 | Ex. | IC$_{50}$ (μM) pSTAT3 | IC$_{50}$ (μM) pSTAT1 |
|---|---|---|---|---|---|
| 19 | 0.029 | >50 | 20 | 0.067 | >50 |
| 21 | 0.11 | >50 | 22 | 0.015 | >50 |
| 23 | 0.084 | >50 | 24 | 0.90 | >50 |
| 25 | 0.034 | >50 | 26 | 0.065 | >50 |
| 27 | 0.075 | >50 | 28 | 0.0085 | >50 |
| 29 | 0.0041 | >50 | 30 | 0.0013 | >50 |
| 31 | 0.0025 | >50 | 32 | 0.010 | >50 |
| 33 | 0.054 | >50 | 34 | 8.7 | >50 |
| 35 | 0.1 | >50 | 36 | 0.064 | 42.1 |
| 37 | 0.015 | >50 | 38 | 0.018 | >50 |
| 39 | 0.0089 | >50 | 40 | 0.21 | >50 |
| 41 | 0.16 | >50 | 42 | 1.25 | >50 |
| 43 | 0.023 | >50 | 44 | 0.019 | >50 |
| 45 | 0.078 | >50 | 46 | 0.054 | >50 |
| 47 | 0.022 | >50 | 48 | 0.014 | >50 |
| 49 | 0.019 | >50 | 50 | 0.078 | >50 |
| 51 | 0.022 | >50 | 52 | 0.025 | >50 |
| 53 | 0.033 | >50 | 54 | 0.014 | >50 |
| 55 | 0.0022 | >50 | 56 | 3.3 | >50 |
| 57 | 0.027 | >50 | 58 | 0.86 | >50 |
| 59 | 0.31 | >50 | 60 | 0.12 | >50 |
| 61 | 0.08 | >50 | 62 | 0.020 | >50 |
| 63 | 0.034 | >50 | 64 | 0.021 | >50 |
| 65 | 0.079 | >50 | 66 | 0.18 | >50 |
| 67 | 0.0084 | >50 | 68 | 0.011 | >50 |
| 69 | 0.010 | >50 | 70 | 0.024 | >50 |
| 71 | 0.011 | >50 | 72 | 0.01 | >50 |
| 73 | 0.13 | >50 | 74 | 0.12 | >50 |
| 75 | 0.24 | >50 | 76 | 0.39 | 3.1 |
| 77 | 0.10 | >50 | 78 | 0.050 | >50 |
| 79 | 0.041 | >50 | 80 | 0.04 | >50 |
| 81 | 0.0050 | >50 | 82 | 0.0058 | >50 |
| 83 | 0.0082 | >50 | 84 | 0.0065 | >50 |
| 85 | 0.11 | >50 | 86 | 0.089 | >50 |
| 87 | 0.0097 | >50 | 88 | >10 | >50 |
| 89 | 0.14 | >50 | 90 | 0.011 | >50 |
| 91 | 0.0051 | >50 | 92 | 5.5 | 9.6 |
| 93 | 0.072 | >50 | 94 | 5.2 | 13.3 |
| 95 | 0.028 | 35.7 | 96 | 0.19 | >50 |
| 97 | 0.025 | >50 | 98 | 0.031 | >50 |
| 99 | 0.11 | >50 | 100 | 0.07 | >50 |
| 101 | 0.0093 | >50 | 102 | 2.1 | 14.5 |
| 103 | 0.18 | >50 | 104 | 1.4 | 8.7 |
| 105 | 0.049 | >50 | 106 | 0.43 | 8.5 |
| 107 | >10 | 33.5 | 108 | 0.085 | >50 |
| 109 | 0.46 | >50 | 110 | 0.53 | 44.8 |
| 111 | 1.3 | >50 | 112 | 0.32 | 18.9 |
| 113 | 0.18 | >50 | 114 | 0.063 | >50 |
| 115 | 0.019 | >50 | 116 | 0.20 | >50 |
| 117 | 0.028 | >50 | 118 | 6.0 | 8.6 |
| 119 | 2.8 | 12.8 | 120 | 0.078 | 39.6 |
| 121 | 0.027 | >50 | | | |

As shown in Table 9, the compounds according to the present invention exhibited excellent inhibitory effects against the activity of STAT3 protein but showed almost no inhibitory effect against the activity of STAT1 protein.

Experimental Example 2) Cell Growth Inhibition Assay

The inhibitory effects of the compounds of the present invention against the growth of cancer cells were evaluated as shown below. The cancer cell lines including prostate cancer cell lines (LNCaP, DU-145), stomach cancer cell line (NCI-N87), and breast cancer cell lines (MDA-MB-468) were cultured under the protocol provided by each supplier. A medium supplemented with 10 ng/mL of IL-6 was used for LNCaP, a prostate cancer cell line, when treated with a drug. Each type of cells to be used in experiments was sub-cultured in a 96-well plate by counting the exact number of cells using Tali™ Image-based Cytometer (Life Technologies). In a 96-well plate, DU-145 was employed with 3,000 cells/well; NCI-N87 was employed with 5,000 cells/well; and LNCaP and MDA-MB-468 were employed with 10,000 cells/well. The cells were treated with the compounds listed in Examples which were diluted in various concentrations. Upon completion of the compounds treatment, LNCaP, DU-145, NCI-N87 cells were cultured at 37° C. under 5% $CO_2$ for 96 hours, and MDA-MB-468 cells were cultured at 37° C. in air for 96 hours. Subsequently, the cells were observed under microscope and drug precipitation and particular findings were investigated and recorded. And then, the 96-well plate was placed at room temperature for 30 minutes, added with 20 pt/well of CellTiter-Glo solution (Cat No. G7573, Promega) and shaken for 10 minutes, followed by being subjected to the measurement using PHERAstar™ microplate reader (BMG LABTECH) according to the supplier's general luminometer protocol. Wells where only culture liquid added without cell plating were used as a negative control, whereas wells where culture liquid containing 0.1% DMSO instead of the compounds listed in Examples were used as a positive control.

The results of the inhibitory effects of the compounds prepared in Examples against the growth of cancer cells are shown in Tables 10 to 13 below.

TABLE 10

| Ex. | IC$_{50}$ (μM) LNCap | Ex. | IC$_{50}$ (μM) LNCap | Ex. | IC$_{50}$ (μM) LNCap | Ex. | IC$_{50}$ (μM) LNCap |
|---|---|---|---|---|---|---|---|
| 16 | 0.0022 | 17 | 0.080 | 18 | 0.056 | 19 | 0.043 |
| 21 | 0.040 | 22 | 0.024 | 23 | 0.80 | 24 | >1.1 |
| 25 | 0.072 | 27 | 0.029 | 33 | 0.030 | 34 | >1.1 |
| 37 | 0.01 | 38 | 0.0083 | 41 | 0.12 | 42 | >1.1 |
| 43 | 0.032 | 44 | 0.039 | 45 | 0.53 | 46 | 0.11 |
| 47 | 0.02 | 48 | 0.01 | 49 | 0.019 | 51 | 0.031 |
| 52 | 0.022 | 53 | 0.037 | 54 | 0.029 | 56 | >1.1 |
| 58 | 0.24 | 63 | 0.046 | 64 | 0.013 | 66 | 0.26 |
| 67 | 0.047 | 88 | >1.1 | 89 | 0.24 | 92 | >1.1 |
| 93 | 0.26 | 94 | >1.1 | 95 | 0.023 | 97 | 0.028 |
| 98 | 0.031 | 99 | 0.14 | 100 | 0.14 | | |

TABLE 11

| Ex. | IC$_{50}$ (μM) DU-145 | Ex. | IC$_{50}$ (μM) DU-145 | Ex. | IC$_{50}$ (μM) DU-145 | Ex. | IC$_{50}$ (μM) DU-145 |
|---|---|---|---|---|---|---|---|
| 16 | 0.0018 | 17 | 0.039 | 18 | 0.023 | 19 | 0.022 |
| 21 | 0.017 | 22 | 0.014 | 23 | 0.04 | 24 | >1.1 |
| 25 | 0.066 | 27 | 0.024 | 33 | 0.023 | 34 | >1.1 |
| 37 | 0.0071 | 38 | 0.0053 | 41 | 0.063 | 42 | >1.1 |
| 43 | 0.011 | 44 | 0.019 | 45 | 0.037 | 46 | 0.07 |
| 47 | 0.016 | 48 | 0.008 | 49 | 0.013 | 51 | 0.0082 |
| 52 | 0.015 | 53 | 0.02 | 54 | 0.0059 | 56 | >1.1 |
| 58 | 0.11 | 63 | 0.032 | 64 | 0.0057 | 66 | 0.17 |
| 67 | 0.0053 | 88 | >1.1 | 89 | 0.11 | 92 | >1.1 |
| 93 | 0.1 | 94 | >1.1 | 95 | 0.013 | 97 | 0.016 |
| 98 | 0.0066 | 99 | 0.046 | 100 | 0.026 | | |

TABLE 12

| Ex. | IC$_{50}$ (μM) NCI-N87 | Ex. | IC$_{50}$ (μM) NCI-N87 | Ex. | IC$_{50}$ (μM) NCI-N87 | Ex. | IC$_{50}$ (μM) NCI-N87 |
|---|---|---|---|---|---|---|---|
| 9 | 0.02 | 10 | 0.01 | 11 | 0.011 | 12 | 0.025 |
| 13 | 0.028 | 14 | 0.010 | 15 | 0.0093 | 31 | 0.24 |
| 32 | 0.076 | 36 | 0.25 | 39 | 0.031 | 57 | 0.2 |
| 62 | 0.034 | 64 | 0.034 | 67 | 0.021 | 68 | 0.03 |
| 69 | 0.015 | 70 | 0.057 | 71 | 0.020 | 72 | 0.021 |
| 73 | 0.45 | 74 | 0.61 | 77 | 0.052 | 78 | 0.2 |
| 79 | 0.043 | 80 | 0.069 | 81 | 0.033 | 82 | 0.035 |
| 83 | 0.020 | 84 | 0.020 | 86 | 0.15 | 96 | 1.5 |
| 101 | 0.068 | 103 | 1.3 | 104 | 1.7 | 105 | 0.087 |
| 106 | 1.8 | 107 | 5.5 | 108 | 0.13 | 109 | 1.7 |
| 110 | 1.2 | 111 | 2.4 | 112 | 1 | 113 | 0.27 |
| 114 | 0.13 | 115 | 0.14 | 116 | 0.91 | 117 | 0.037 |
| 119 | 7.8 | 120 | 0.12 | 121 | 0.15 | | |

TABLE 13

| Ex. | IC$_{50}$ (μM) MDA-MB-468 | Ex. | IC$_{50}$ (μM) MDA-MB-468 | Ex. | IC$_{50}$ (μM) MDA-MB-468 | Ex. | IC$_{50}$ (μM) MDA-MB-468 |
|---|---|---|---|---|---|---|---|
| 64 | 0.0065 | 71 | 0.0056 | 72 | 0.0040 | 79 | 0.0074 |
| 80 | 0.0084 | 81 | 0.0038 | 82 | 0.0041 | 83 | 0.0052 |
| 84 | 0.0026 | 86 | 0.024 | 109 | 0.068 | 115 | 0.021 |
| 116 | 0.062 | 117 | 0.0053 | 119 | >0.1 | 120 | 0.026 |
| 121 | 0.027 | | | | | | |

As shown in Tables 10 to 13, the compounds according to the present invention exhibited excellent inhibitory effects against the growth of various kinds of cancer cells.

What is claimed is:

1. A compound selected from the group consisting of a heterocyclic compound of formula (I), and a pharmaceutically acceptable salt and a stereoisomer thereof:

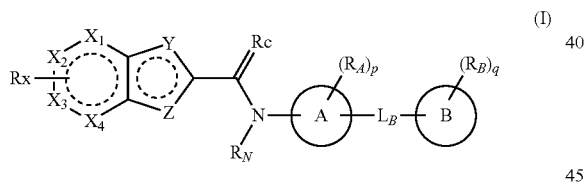

(I)

wherein
one of $X_1$, $X_2$, $X_3$ and $X_4$ is —C(-Rx)=, and the others are each independently —C(-Rx')= or —N=;
one of Y and Z is —S— or —NH—, and the other is —CH= or —N=;
Rx is

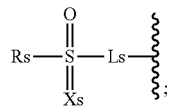

Xs is =O or =NH;
Ls is —C(-Rs')(-Rs")-;
Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, amino$C_{1-6}$alkyl or 5- to 10-membered heterocyclyl, or Rs is linked to Rs' to form a chain;
Rs' and Rs" are each independently hydrogen, halogen, $C_{1-6}$alkyl, carbamoyl-$C_{1-6}$alkyl, $C_{1-6}$alkylamino-$C_{1-6}$alkyl or di$C_{1-6}$alkylamino-$C_{1-6}$alkyl, or Rs' and Rs" are linked together to form a chain, or Rs' is linked to Rs to form a chain;
Rx' is each independently hydrogen, halogen, nitro, amino, $C_{1-6}$alkoxy, halo$C_{1-6}$alkoxy, or $C_{1-6}$alkylsulfonyl;
A and B are each independently a monocyclic- or bicyclic-saturated or unsaturated $C_{3-10}$carbocycle or 5- to 12-membered heterocycle;
Rc is =O, =NH, =N(—$C_{1-6}$alkyl), or =N(—OH);
$R_N$ is hydrogen or $C_{1-6}$alkyl, or $R_N$ is linked to $R_A$ to form a chain;
$L_B$ is —[C(—$R_L$)(—$R_L$')]$_m$—, —[C(—$R_L$)(—$R_L$')]$_n$—O—, —O—, —NH—, —N($C_{1-6}$alkyl)-, —S(=O)$_2$—, —C(=O)—, or —C(=CH$_2$)—, wherein m is an integer of 0 to 3, n is an integer of 1 to 3, $R_L$ and $R_L$' are each independently hydrogen, hydroxy, halogen or $C_{1-6}$alkyl, or $R_L$ and $R_L$' are linked together to form a chain;
$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$alkoxy, cyano$C_{1-6}$alkoxy, $C_{1-6}$alkylamino, di$C_{1-6}$alkylamino, $C_{1-6}$alkylthio, $C_{1-6}$alkylaminocarbonyl, di$C_{1-6}$alkylaminocarbonyl, $C_{2-8}$alkynyl, $C_{1-6}$alkoxycarbonylamino-$C_{1-6}$alkoxy, amino $C_{1-6}$alkoxy or 3- to 6-membered heterocyclyl, or $R_A$ is linked to $R_N$ to form a chain;
$R_B$ is hydrogen, halogen, hydroxy, cyano, nitro, amino, oxo, aminosulfonyl, sulfonylamido, $C_{1-6}$alkylamino, $C_{1-6}$alkyl, halo$C_{1-6}$alkyl, cyano$C_{1-6}$alkyl, $C_{1-6}$alkoxy, halo$C_{1-6}$alkoxy, cyano$C_{1-6}$alkoxy, $C_{3-8}$cyclcoalkyloxy, $C_{2-8}$alkenyl, $C_{2-8}$alkenyloxy, $C_{2-8}$alkynyl, $C_{2-8}$alkynyloxy, $C_{1-6}$alkylamino-$C_{1-6}$alkoxy, di$C_{1-6}$alkylamino-$C_{1-6}$alkoxy, $C_{1-6}$alkoxycarbonyl, carbamoyl, carbamoyl-$C_{1-6}$alkoxy, $C_{1-6}$alkylthio, $C_{1-6}$alkylsulfinyl, $C_{1-6}$alkylsulfonyl, 5- to 10-membered heterocyclyl, 5- to 10-membered heterocyclyl-$C_{1-6}$alkyl, 5- to 10-membered heterocyclyl-$C_{1-6}$alkoxy, or 5- to 10-membered heterocyclyl-oxy;

p is an integer of 0 to 4, and, when p is 2 or higher, $R_A$ moieties are the same as or different from each other;

q is an integer of 0 to 4, and, when q is 2 or higher, $R_B$ moieties are the same as or different from each other; and each of said chains is independently a saturated or unsaturated $C_{2-10}$ hydrocarbon chain not containing or containing at least one heterogroup selected from the group consisting of —O—, —NH—, —N═, —S—, —S(═O)— and —S(═O)$_2$— in the chain, and unsubstituted or substituted with at least one selected from the group consisting of halogen, $C_{1-6}$alkyl and $C_{1-6}$alkoxy; and each of said heterocycle and heterocyclyl moieties independently contains at least one heterogroup selected from the group consisting of —O—, —NH—, —N═, —S—, —S(═O)— and —S(═O)$_2$—.

2. The compound according to claim 1, wherein
one of $X_2$ and $X_3$ is —C(-Rx)═, and the other is —C(-Rx')═ or —N═;
$X_1$ and $X_4$ are each independently —C(-Rx')═ or —N═;
one of Y and Z is —S— or —NH—, and the other is —CH═; and
Rx and Rx' are the same as defined in claim 1.

3. The compound according to claim 2, wherein
Rx is

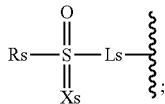

Xs is ═O or ═NH;
Ls is —C(-Rs')(-Rs")-;
Rs is $C_{1-6}$alkyl, halo$C_{1-6}$alkyl, $C_{1-6}$alkoxy-$C_{1-6}$alkyl or 5- to 6-membered heterocyclyl, or Rs is linked to Rs' to form a chain;
Rs' and Rs" are each independently hydrogen, halogen or $C_{1-6}$alkyl, or Rs' and Rs" are linked together to form a chain, or Rs' is linked to Rs to form a chain;
Rx' is each independently hydrogen or halogen; and
each of said chains is independently a saturated or unsaturated $C_{2-7}$ hydrocarbon chain not containing or containing at least one heteroatom selected from the group consisting of O, N and S.

4. The compound according to claim 3, wherein
A is benzene or a 5- to 10-membered heteroaryl containing 1 to 3 nitrogen atoms;
B is a monocyclic- or bicyclic-saturated or unsaturated $C_{6-10}$carbocycle or 5- to 10-membered heterocycle;
$L_B$ is —[C(—$R_L$)(—$R_L$')]$_m$—, —O—, —NH—, or —N($C_{1-6}$alkyl)-, wherein m is 0 or 1, $R_L$ and $R_L$' are each independently hydrogen, hydroxy, halogen or $C_{1-6}$alkyl, or $R_L$ and $R_L$' are linked together to form $C_{2-5}$alkylene;
$R_A$ is halogen, $C_{1-6}$alkoxycarbonylamino-$C_{1-6}$alkoxy, amino$C_{1-6}$alkoxy, or 3- to 6-membered heterocyclyl;
$R_B$ is halogen, $C_{1-6}$alkyl, $C_{1-6}$alkoxy, halo$C_{1-6}$alkyloxy, $C_{2-6}$alkenyloxy, $C_{2-6}$alkynyloxy, $C_{1-6}$alkoxycarbonyl, $C_{3-10}$carbocyclyl-oxy, or 3- to 10-membered heterocyclyl-$C_{1-3}$alkoxy; and
each of said heteroaryl, heterocycle and heterocyclyl moieties independently contains 1 to 3 heteroatoms selected from the group consisting of O, N and S.

5. The compound according to claim 1, wherein
$X_1$ and $X_4$ are —CH═;
$X_2$ is —C(-Rx)═;
$X_3$ is —N═ or —C(-Rx')-;
Y is —C═;
Z is —S—;
Rx is

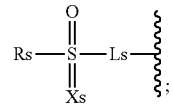

Ls is —C(—CH$_3$)(—CH$_3$)—;
Rs is $C_{1-6}$alkyl, halo$C_{1-6}$alkyl, $C_{1-6}$alkoxy$C_{1-6}$alkyl, $C_{1-6}$alkylcarbonyl$C_{1-6}$alkyl, $C_{2-7}$alkenyl, amino, amino$C_{1-6}$alkyl, or a 5- to 10-membered heterocyclyl containing 1 to 3 heteroatoms selected from the group consisting of O, N and S;
Rx' is hydrogen, halogen, nitro, amino, $C_{1-6}$alkoxy, halo$C_{1-6}$alkoxy, or $C_{1-6}$alkylsulfonyl;
Rc is ═O; and
$R_N$ is hydrogen.

6. The compound according to claim 1, wherein
$X_1$, $X_3$ and $X_4$ are —CH═;
$X_2$ is —C(-Rx)═;
Y is —C═;
Z is —S—;
Rx is

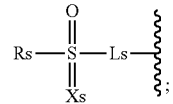

Ls is —C(-Rs')(-Rs")-;
Xs is ═O or ═NH;
Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, amino$C_{1-6}$alkyl, or a 5- to 10-membered heterocyclyl containing 1 to 3 heteroatoms selected from the group consisting of O, N and S;
Rs' and Rs" are each independently hydrogen, halogen, $C_{1-6}$alkyl, carbamoyl$C_{1-6}$alkyl, $C_{1-6}$alkylamino-$C_{1-6}$alkyl or di$C_{1-6}$alkylamino-$C_{1-6}$alkyl, or Rs' and Rs" are linked together to form a chain, wherein the chain is a saturated or unsaturated $C_{2-10}$ hydrocarbon chain not containing or containing at least one heterogroup selected from the group consisting of —O—, —NH—, —N═, —S—, —S(═O)— and —S(═O)$_2$— in the chain, and unsubstituted or substituted with at least one selected from the group consisting of halogen, $C_{1-6}$alkyl and $C_{1-6}$alkoxy;
Rc is ═O; and
$R_N$ is hydrogen.

7. The compound according to claim 1, wherein
$X_1$, $X_3$ and $X_4$ are —CH═;
$X_2$ is —C(-Rx)═;
Y is —C═;
Z is —S—;
Rx is the same as defined in claim 1;
Rc is ═O; and
$R_N$ is hydrogen.

8. The compound according to claim 1, wherein
$X_1$, $X_2$ and $X_4$ are —CH=;
$X_3$ is —C(-Rx)=;
Y is —C=;
Z is —S— or —NH—;
Rx is

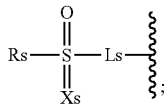

Xs is =O;
Ls is —C(—CH$_3$)(—CH$_3$)—;
Rs is methyl;
Rc is =O; and
$R_N$ is hydrogen.

9. The compound according to claim 1, which is selected from the group consisting of:
1) N-(3-chloro-5-(2-(3-ethoxy-5-(trifluoromethoxy)phenyl)propan-2-yl)phenyl)-5-(2-(methylsulfonyl)propan-2-yl)benzo[b]thiophene-2-carboxamide;
2) N-(3-chloro-5-(2-(3-propoxy-5-(trifluoromethoxy)phenyl)propan-2-yl)phenyl)-5-(2-(methylsulfonyl)propan-2-yl)benzo[b]thiophene-2-carboxamide;
3) N-(3-(2-(3-methoxy-5-(trifluoromethoxy)phenyl)propan-2-yl)phenyl)-5-(2-(methylsulfonyl)propan-2-yl)benzo[b]thiophene-2-carboxamide;
4) N-(3-bromo-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide;
5) N-(3-chloro-5-(2-(3-(1,1,2,2-tetrafluoroethoxy)-5-(trifluoromethoxy)phenyl)propan-2-yl)phenyl)-5-(2-(methylsulfonyl)propan-2-yl)benzo[b]thiophene-2-carboxamide;
6) N-(3-methoxy-5-(2-(3-methoxy-5-(trifluoromethoxy)phenyl)propan-2-yl)phenyl)-5-(2-(methylsulfonyl)propan-2-yl)benzo[b]thiophene-2-carboxamide;
7) N-(3-chloro-5-(2-(3-methoxy-5-(trifluoromethoxy)phenyl)propan-2-yl)phenyl)-5-(2-(methylsulfonyl)propan-2-yl)benzo[b]thiophene-2-carboxamide;
8) N-(3-chloro-5-(2-(3-(2-morpholinoethoxy)-5-(trifluoromethoxy)phenyl)propan-2-yl)phenyl)-5-(2-(methylsulfonyl)propan-2-yl)benzo[b]thiophene-2-carboxamide;
9) N-(3-bromo-5-(2-(3-isopropoxy-5-(trifluoromethoxy)phenyl)propan-2-yl)phenyl)-5-(2-(methylsulfonyl)propan-2-yl)benzo[b]thiophene-2-carboxamide;
10) N-(3-(2-(3-(but-2-yn-1-yloxy)-5-(trifluoromethoxy)phenyl)propan-2-yl)-5-chlorophenyl)-5-(2-(methylsulfonyl)propan-2-yl)benzo[b]thiophene-2-carboxamide;
11) N-(3-chloro-5-(2-(3-isobutoxy-5-(trifluoromethoxy)phenyl)propan-2-yl)phenyl)-5-(2-(methylsulfonyl)propan-2-yl)benzo[b]thiophene-2-carboxamide;
12) N-(3-chloro-5-(2-(3-(2,2,2-trifluoroethoxy)-5-(trifluoromethoxy)phenyl)propan-2-yl)phenyl)-5-(2-(methylsulfonyl)propan-2-yl)benzo[b]thiophene-2-carboxamide;
13) N-(3-chloro-5-(2-(3-(2,2-difluoroethoxy)-5-(trifluoromethoxy)phenyl)propan-2-yl)phenyl)-5-(2-(methylsulfonyl)propan-2-yl)benzo[b]thiophene-2-carboxamide;
14) N-(3-(2-(3-(allyloxy)-5-(trifluoromethoxy)phenyl)propan-2-yl)-5-chlorophenyl)-5-(2-(methylsulfonyl)propan-2-yl)benzo[b]thiophene-2-carboxamide;
15) N-(3-chloro-5-(2-(3-cyclopropoxy-5-(trifluoromethoxy)phenyl)propan-2-yl)phenyl)-5-(2-(methylsulfonyl)propan-2-yl)benzo[b]thiophene-2-carboxamide;
16) N-(3-chloro-5-(2-(3-isopropoxy-5-(trifluoromethoxy)phenyl)propan-2-yl)phenyl)-5-((methylsulfonyl)methyl)benzo[b]thiophene-2-carboxamide;
17) N-(3-chloro-5-(2-(4-methoxyphenyl)propan-2-yl)phenyl)-5-(2-(methylsulfonyl)propan-2-yl)benzo[b]thiophene-2-carboxamide;
18) N-(3-chloro-5-(2-(4-fluorophenyl)propan-2-yl)phenyl)-5-(2-(methylsulfonyl)propan-2-yl)benzo[b]thiophene-2-carboxamide;
19) N-(3-chloro-5-(2-(4-fluorophenyl)propan-2-yl)phenyl)-6-fluoro-5-(2-(methylsulfonyl)propan-2-yl)benzo[b]thiophene-2-carboxamide;
20) N-(3-bromo-5-(2-(4-fluorophenyl)propan-2-yl)phenyl)-5-(2-(methylsulfonyl)propan-2-yl)benzo[b]thiophene-2-carboxamide;
21) N-(3-chloro-5-(2-(4-chlorophenyl)propan-2-yl)phenyl)-5-((methylsulfonyl)methyl)benzo[b]thiophene-2-carboxamide;
22) N-(3-chloro-5-(2-(4-chlorophenyl)propan-2-yl)phenyl)-5-(2-(methylsulfonyl)propan-2-yl)benzo[b]thiophene-2-carboxamide;
23) 6-chloro-N-(3-chloro-5-(2-(4-chlorophenyl)propan-2-yl)phenyl)-5-(2-(methylsulfonyl)propan-2-yl)benzo[b]thiophene-2-carboxamide;
24) N-(3-chloro-5-(2-(4-chlorophenyl)propan-2-yl)phenyl)-5-(((trifluoromethyl)sulfonyl)methyl)benzo[b]thiophene-2-carboxamide;
25) N-(3-chloro-5-(2-(4-chlorophenyl)propan-2-yl)phenyl)-5-(fluoro(methylsulfonyl)methyl)benzo[b]thiophene-2-carboxamide;
26) N-(3-chloro-5-(2-(4-chlorophenyl)propan-2-yl)phenyl)-5-(2-(methylsulfonyl)propan-2-yl)thieno[2,3-c]pyridine-2-carboxamide;
27) N-(3-chloro-5-(2-(5-chlorothiophen-2-yl)propan-2-yl)phenyl)-5-(2-(methylsulfonyl)propan-2-yl)benzo[b]thiophene-2-carboxamide;
28) N-(3-chloro-5-(2-(5-isopropylthiophen-2-yl)propan-2-yl)phenyl)-5-(2-(methylsulfonyl)propan-2-yl)benzo[b]thiophene-2-carboxamide;
29) N-(3-chloro-5-(2-(5-methoxythiophen-2-yl)propan-2-yl)phenyl)-5-(2-(methylsulfonyl)propan-2-yl)benzo[b]thiophene-2-carboxamide;
30) N-(3-chloro-5-(2-(2-methoxythiophen-3-yl)propan-2-yl)phenyl)-5-(2-(methylsulfonyl)propan-2-yl)benzo[b]thiophene-2-carboxamide;
31) N-(3-chloro-5-(2-(1-methyl-1H-pyrrol-2-yl)propan-2-yl)phenyl)-5-(2-(methylsulfonyl)propan-2-yl)benzo[b]thiophene-2-carboxamide;
32) N-(3-chloro-5-(2-(4-methylthiophen-2-yl)propan-2-yl)phenyl)-5-(2-(methylsulfonyl)propan-2-yl)benzo[b]thiophene-2-carboxamide;
33) N-(3-chloro-5-(2-(4-chlorophenyl)propan-2-yl)phenyl)-5-(1-(methylsulfonyl)cyclopropyl)benzo[b]thiophene-2-carboxamide;
34) N-(3-chloro-5-(2-(4-chlorophenyl)propan-2-yl)phenyl)-5-(4-(methylsulfonyl)tetrahydro-2H-pyran-4-yl)benzo[b]thiophene-2-carboxamide;
35) N-(3-chloro-5-(2-(4-chlorophenyl)propan-2-yl)phenyl)-6-(2-(methylsulfonyl)propan-2-yl)-1H-indole-2-carboxamide;

36) N-(3-chloro-5-(2-(4-chlorophenyl)propan-2-yl)phenyl)-5-((S-methylsulfonimidoyl)methyl)benzo[b]thiophene-2-carboxamide;
37) N-(3-chloro-5-(4-(trifluoromethoxy)phenoxy)phenyl)-5-(2-(methylsulfonyl)propan-2-yl)benzo[b]thiophene-2-carboxamide;
38) N-(3-chloro-5-(4-(trifluoromethyl)phenoxy)phenyl)-5-(2-(methylsulfonyl)propan-2-yl)benzo[b]thiophene-2-carboxamide;
39) N-(3-bromo-5-(4-chlorophenoxy)phenyl)-5-(2-(methylsulfonyl)propan-2-yl)benzo[b]thiophene-2-carboxamide;
40) N-(3-chloro-5-(4-chlorophenoxy)phenyl)-6-(2-(methylsulfonyl)propan-2-yl)-1H-indole-2-carboxamide;
41) N-(3-chloro-5-(4-chlorophenoxy)phenyl)-5-((methylsulfonyl)methyl)benzo[b]thiophene-2-carboxamide;
42) N-(3-chloro-5-(4-chlorophenoxy)phenyl)-5-(((trifluoromethyl)sulfonyl)methyl)benzo[b]thiophene-2-carboxamide;
43) N-(3-chloro-5-(4-fluorophenoxy)phenyl)-5-(2-(methylsulfonyl)propan-2-yl)benzo[b]thiophene-2-carboxamide;
44) N-(3-chloro-5-(4-chlorophenoxy)phenyl)-6-fluoro-5-(2-(methylsulfonyl)propan-2-yl)benzo[b]thiophene-2-carboxamide;
45) 6-chloro-N-(3-chloro-5-(4-chlorophenoxy)phenyl)-5-(2-(methylsulfonyl)propan-2-yl)benzo[b]thiophene-2-carboxamide;
46) N-(3-(4-chlorophenoxy)-5-methoxyphenyl)-5-(2-(methylsulfonyl)propan-2-yl)benzo[b]thiophene-2-carboxamide;
47) N-(3-chloro-5-(3-chloro-5-fluorophenoxy)phenyl)-5-(2-(methylsulfonyl)propan-2-yl)benzo[b]thiophene-2-carboxamide;
48) N-(3-chloro-5-(3-(trifluoromethoxy)phenoxy)phenyl)-5-(2-(methylsulfonyl)propan-2-yl)benzo[b]thiophene-2-carboxamide;
49) N-(3-chloro-5-(4-chlorophenoxy)phenyl)-5-(2-(methylsulfonyl)propan-2-yl)benzo[b]thiophene-2-carboxamide;
50) N-(3-chloro-5-(4-chlorophenoxy)phenyl)-5-(2-(methylsulfonyl)propan-2-yl)thieno[2,3-c]pyridine-2-carboxamide;
51) N-(3-chloro-5-(3-chloro-4-fluorophenoxy)phenyl)-5-(2-(methylsulfonyl)propan-2-yl)benzo[b]thiophene-2-carboxamide;
52) N-(3-chloro-5-(3,4-difluorophenoxy)phenyl)-5-(2-(methylsulfonyl)propan-2-yl)benzo[b]thiophene-2-carboxamide;
53) N-(3-chloro-5-(3-fluoro-5-methoxyphenoxy)phenyl)-5-(2-(methylsulfonyl)propan-2-yl)benzo[b]thiophene-2-carboxamide;
54) N-(3-chloro-5-(4-chloro-3-fluorophenoxy)phenyl)-5-(2-(methylsulfonyl)propan-2-yl)benzo[b]thiophene-2-carboxamide;
55) N-(3-chloro-5-(2-(3-chloro-5-methoxyphenyl)propan-2-yl)phenyl)-5-(2-(methylsulfonyl)propan-2-yl)benzo[b]thiophene-2-carboxamide;
56) N-(3-chloro-5-(4-chlorophenoxy)phenyl)-5-(4-(methylsulfonyl)tetrahydro-2H-pyran-4-yl)benzo[b]thiophene-2-carboxamide;
57) N-(3-chloro-5-(4-chlorophenoxy)phenyl)-5-(2-((2-methoxyethyl)sulfonyl)propan-2-yl)benzo[b]thiophene-2-carboxamide;
58) N-(3-chloro-5-(4-chlorophenoxy)phenyl)-6-(2-(methylsulfonyl)propan-2-yl)benzo[b]thiophene-2-carboxamide;
59) N-(3-(azetidin-1-yl)-5-(4-chlorophenoxy)phenyl)-5-(2-(methylsulfonyl)propan-2-yl)benzo[b]thiophene-2-carboxamide;
60) N-(3-chloro-5-((6-chloropyridin-3-yl)oxy)phenyl)-5-(2-(methylsulfonyl)propan-2-yl)benzo[b]thiophene-2-carboxamide;
61) N-(3-chloro-5-((5-chloropyridin-2-yl)oxy)phenyl)-5-(2-(methylsulfonyl)propan-2-yl)benzo[b]thiophene-2-carboxamide;
62) N-(2-chloro-6-(3,5-dichlorophenoxy)pyridin-4-yl)-5-(2-(methylsulfonyl)propan-2-yl)benzo[b]thiophene-2-carboxamide;
63) N-(6-chloro-4-(4-chlorophenoxy)pyridin-2-yl)-5-(2-(methylsulfonyl)propan-2-yl)benzo[b]thiophene-2-carboxamide;
64) N-(2-chloro-6-(4-chlorophenoxy)pyridin-4-yl)-5-(2-(methylsulfonyl)propan-2-yl)benzo[b]thiophene-2-carboxamide;
65) N-(2-chloro-6-((6-chloropyridin-3-yl)oxy)pyridin-4-yl)-5-(2-(methylsulfonyl)propan-2-yl)benzo[b]thiophene-2-carboxamide;
66) N-(4-chloro-6-(4-chlorophenoxy)pyridin-2-yl)-5-(2-(methylsulfonyl)propan-2-yl)benzo[b]thiophene-2-carboxamide;
67) N-(2-chloro-6-(4-(trifluoromethyl)phenoxy)pyridin-4-yl)-5-(2-(methylsulfonyl)propan-2-yl)benzo[b]thiophene-2-carboxamide;
68) N-(2-chloro-6-(4-fluorophenoxy)pyridin-4-yl)-5-(2-(methylsulfonyl)propan-2-yl)benzo[b]thiophene-2-carboxamide;
69) N-(2-bromo-6-(4-chlorophenoxy)pyridin-4-yl)-5-(2-(methylsulfonyl)propan-2-yl)benzo[b]thiophene-2-carboxamide;
70) N-(2-chloro-6-(3-chloro-5-methoxyphenoxy)pyridin-4-yl)-5-(2-(methylsulfonyl)propan-2-yl)benzo[b]thiophene-2-carboxamide;
71) N-(2-chloro-6-(3-chloro-4-fluorophenoxy)pyridin-4-yl)-5-(2-(methylsulfonyl)propan-2-yl)benzo[b]thiophene-2-carboxamide;
72) N-(2-chloro-6-(4-chloro-3-fluorophenoxy)pyridin-4-yl)-5-(2-(methylsulfonyl)propan-2-yl)benzo[b]thiophene-2-carboxamide;
73) N-(2-chloro-6-(4-chlorophenoxy)pyridin-4-yl)-5-(1,1-dioxidotetrahydrothiophen-2-yl)benzo[b]thiophene-2-carboxamide;
74) N-(2-chloro-6-(4-chlorophenoxy)pyridin-4-yl)-5-(1,1-dioxidotetrahydro-2H-thiopyran-2-yl)benzo[b]thiophene-2-carboxamide;
75) N-(2-chloro-6-(4-chlorophenoxy)pyrimidin-4-yl)-5-(2-(methylsulfonyl)propan-2-yl)benzo[b]thiophene-2-carboxamide;
76) N-(6-chloro-2-(4-chlorophenoxy)pyrimidin-4-yl)-5-(2-(methylsulfonyl)propan-2-yl)benzo[b]thiophene-2-carboxamide;
77) N-(2-(4-chlorophenoxy)-6-fluoropyridin-4-yl)-5-(2-(methylsulfonyl)propan-2-yl)benzo[b]thiophene-2-carboxamide;
78) N-(2-(bicyclo[2.2.1]hept-5-en-2-yloxy)-6-chloropyridin-4-yl)-5-(2-(methylsulfonyl)propan-2-yl)benzo[b]thiophene-2-carboxamide;
79) N-(2-chloro-6-(3,4-difluorophenoxy)pyridin-4-yl)-5-(2-(methylsulfonyl)propan-2-yl)benzo[b]thiophene-2-carboxamide;

80) N-(2-chloro-6-(3-chlorophenoxy)pyridin-4-yl)-5-(2-(methylsulfonyl)propan-2-yl)benzo[b]thiophene-2-carboxamide;
81) N-(2-chloro-6-(3-(trifluoromethoxy)phenoxy)pyridin-4-yl)-5-(2-(methylsulfonyl)propan-2-yl)benzo[b]thiophene-2-carboxamide;
82) N-(2-chloro-6-(3,4-dichlorophenoxy)pyridin-4-yl)-5-(2-(methylsulfonyl)propan-2-yl)benzo[b]thiophene-2-carboxamide;
83) N-(2-chloro-6-(4-chloro-2-fluorophenoxy)pyridin-4-yl)-5-(2-(methylsulfonyl)propan-2-yl)benzo[b]thiophene-2-carboxamide;
84) N-(2-chloro-6-(4-(trifluoromethoxy)phenoxy)pyridin-4-yl)-5-(2-(methylsulfonyl)propan-2-yl)benzo[b]thiophene-2-carboxamide;
85) N-(2-chloro-6-((5-chloropyridin-2-yl)oxy)pyridin-4-yl)-5-(2-(methylsulfonyl)propan-2-yl)benzo[b]thiophene-2-carboxamide;
86) N-(2-chloro-6-((4-chlorobenzyl)oxy)pyridin-4-yl)-5-(2-(methylsulfonyl)propan-2-yl)benzo[b]thiophene-2-carboxamide;
87) N-(3-chloro-5-(2-(3-(prop-1-yn-1-yl)-5-(trifluoromethoxy)phenyl)propan-2-yl)phenyl)-5-(2-(methylsulfonyl)propan-2-yl)benzo[b]thiophene-2-carboxamide;
88) N-(1-(tert-butyl)-3-(2-(4-chlorophenyl)propan-2-yl)-1H-pyrazol-5-yl)-5-(2-(methylsulfonyl)propan-2-yl)benzo[b]thiophene-2-carboxamide;
89) N-(3-(2-(4-chlorophenyl)propan-2-yl)-1H-pyrazol-5-yl)-5-(2-(methylsulfonyl)propan-2-yl)benzo[b]thiophene-2-carboxamide;
90) N-(2-chloro-6-(2-(3-methoxy-5-(trifluoromethoxy)phenyl)propan-2-yl)pyridin-4-yl)-5-(2-(methylsulfonyl)propan-2-yl)benzo[b]thiophene-2-carboxamide;
91) N-(4-chloro-6-(2-(3-methoxy-5-(trifluoromethoxy)phenyl)propan-2-yl)pyridin-2-yl)-5-(2-(methylsulfonyl)propan-2-yl)benzo[b]thiophene-2-carboxamide;
92) N-(3-chloro-5-((2,2,6,6-tetramethylpiperidin-4-yl)oxy)phenyl)-5-(2-(methylsulfonyl)propan-2-yl)benzo[b]thiophene-2-carboxamide;
93) tert-butyl (2-(3-(4-chlorophenoxy)-5-(5-(2-(methylsulfonyl)propan-2-yl)benzo[b]thiophene-2-carboxamido)phenoxy)ethyl)carbamate;
94) N-(3-(2-aminoethoxy)-5-(4-chlorophenoxy)phenyl)-5-(2-(methylsulfonyl)propan-2-yl)benzo[b]thiophene-2-carboxamide;
95) N-(5-chloro-2',4'-difluoro-[1,1'-biphenyl]-3-yl)-5-((methylsulfonyl)methyl)benzo[b]thiophene-2-carboxamide;
96) (8-chloro-6-(4-chlorophenoxy)-2,3-dihydro-4H-benzo[b][1,4]oxazin-4-yl)(5-(2-(methylsulfonyl)propan-2-yl)benzo[b]thiophen-2-yl)methanone;
97) N-(3-chloro-5-(1-(4-chlorophenyl)cyclopropyl)phenyl)-5-(2-(methylsulfonyl)propan-2-yl)benzo[b]thiophene-2-carboxamide;
98) N-(3-chloro-5-((2,4-difluorophenyl)(methyl)amino)phenyl)-5-(2-(methylsulfonyl)propan-2-yl)benzo[b]thiophene-2-carboxamide;
99) N-(3-chloro-5-((4-chlorophenyl)(methyl)amino)phenyl)-5-(2-(methylsulfonyl)propan-2-yl)benzo[b]thiophene-2-carboxamide;
100) N-(2-chloro-6-((4-chlorophenyl)(methyl)amino)pyridin-4-yl)-5-(2-(methylsulfonyl)propan-2-yl)benzo[b]thiophene-2-carboxamide;
101) N-(2-chloro-6-((4-chlorocyclohex-3-en-1-yl)oxy)pyridin-4-yl)-5-(2-(methylsulfonyl)propan-2-yl)benzo[b]thiophene-2-carboxamide;
102) N-(2-chloro-6-((octahydroindolizin-7-yl)oxy)pyridin-4-yl)-5-(2-(methylsulfonyl)propan-2-yl)benzo[b]thiophene-2-carboxamide;
103) N-(3-chloro-5-(4-chlorophenoxy)phenyl)-5-(2-(methylsulfonyl)propan-2-yl)benzo[b]thiophene-2-carboximidamide 2,2,2-trifluoroacetate;
104) N-(2-chloro-6-(hexahydropyrrolo[1,2-a]pyrazin-2(1H)-yl)pyridin-4-yl)-5-(2-(methylsulfonyl)propan-2-yl)benzo[b]thiophene-2-carboxamide;
105) N-(2-(4-(tert-butyl)piperidin-1-yl)-6-chloropyridin-4-yl)-5-(2-(methylsulfonyl)propan-2-yl)benzo[b]thiophene-2-carboxamide;
106) N-(2-chloro-6-(octahydro-2H-pyrido[1,2-a]pyrazin-2-yl)pyridin-4-yl)-5-(2-(methylsulfonyl)propan-2-yl)benzo[b]thiophene-2-carboxamide;
107) N-(2-chloro-6-(7-ethyl-2,7-diazaspiro[4.4]nonan-2-yl)pyridin-4-yl)-5-(2-(methylsulfonyl)propan-2-yl)benzo[b]thiophene-2-carboxamide;
108) N-(2-chloro-6-(octahydroisoquinolin-2(1H)-yl)pyridin-4-yl)-5-(2-(methylsulfonyl)propan-2-yl)benzo[b]thiophene-2-carboxamide;
109) N-(2-chloro-6-((5-methylthiazol-2-yl)oxy)pyridin-4-yl)-5-(2-(methylsulfonyl)propan-2-yl)benzo[b]thiophene-2-carboxamide;
110) N-(2-chloro-6-((1-methyl-1H-pyrazol-5-yl)oxy)pyridin-4-yl)-5-(2-(methylsulfonyl)propan-2-yl)benzo[b]thiophene-2-carboxamide;
111) N-(2-chloro-6-((1,3,5-trimethyl-1H-pyrazol-4-yl)oxy)pyridin-4-yl)-5-(2-(methylsulfonyl)propan-2-yl)benzo[b]thiophene-2-carboxamide;
112) N-(2-chloro-6-((1-methyl-1H-pyrazol-4-yl)oxy)pyridin-4-yl)-5-(2-(methylsulfonyl)propan-2-yl)benzo[b]thiophene-2-carboxamide;
113) N-(2-chloro-6-((3,5-dimethylisoxazol-4-yl)oxy)pyridin-4-yl)-5-(2-(methylsulfonyl)propan-2-yl)benzo[b]thiophene-2-carboxamide;
114) N-(2-chloro-6-((5-methylthiophen-3-yl)oxy)pyridin-4-yl)-5-(2-(methylsulfonyl)propan-2-yl)benzo[b]thiophene-2-carboxamide;
115) N-(2-chloro-6-((2-methylthiophen-3-yl)oxy)pyridin-4-yl)-5-(2-(methylsulfonyl)propan-2-yl)benzo[b]thiophene-2-carboxamide;
116) N-(2-chloro-6-((4,5-dimethylisoxazol-3-yl)oxy)pyridin-4-yl)-5-(2-(methylsulfonyl)propan-2-yl)benzo[b]thiophene-2-carboxamide;
117) N-(2-chloro-6-((5-(trifluoromethyl)thiophen-3-yl)oxy)pyridin-4-yl)-5-(2-(methylsulfonyl)propan-2-yl)benzo[b]thiophene-2-carboxamide;
118) methyl 3-((6-chloro-4-(5-(2-(methylsulfonyl)propan-2-yl)benzo[b]thiophene-2-carboxamido)pyridin-2-yl)oxy)isoxazole-5-carboxylate;
119) N-(2-chloro-6-((4-methylthiazol-2-yl)oxy)pyridin-4-yl)-5-(2-(methylsulfonyl)propan-2-yl)benzo[b]thiophene-2-carboxamide;
120) N-(2-chloro-6-((5-methylthiophen-2-yl)oxy)pyridin-4-yl)-5-(2-(methylsulfonyl)propan-2-yl)benzo[b]thiophene-2-carboxamide; and
121) N-(2-chloro-6-((2-chlorothiophen-3-yl)oxy)pyridin-4-yl)-5-(2-(methylsulfonyl)propan-2-yl)benzo[b]thiophene-2-carboxamide.

10. A pharmaceutical composition comprising the compound as defined in claim 1 as an active ingredient and a pharmaceutically acceptable carrier.

11. A method for manufacturing a medicament comprising the compound of claim 1, comprising mixing the compound of claim 1 with a pharmaceutically acceptable additive.

12. A method for inhibiting or treating a disease associated with the activation of STAT3 protein in a mammal, which comprises administering the compound as defined in claim 1 to the mammal, wherein the disease is selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, rheumatoid arthritis, psoriasis, hepatitis, inflammatory bowel disease, Crohn's disease, diabetes, macular degeneration, human papillomavirus infection, and tuberculosis.

\* \* \* \* \*